US012727833B2

(12) United States Patent
Budiman

(10) Patent No.: US 12,727,833 B2
(45) Date of Patent: Sep. 8, 2026

(54) MODEL BASED VARIABLE RISK FALSE GLUCOSE THRESHOLD ALARM PREVENTION MECHANISM

(71) Applicant: ABBOTT DIABETES CARE INC., Alameda, CA (US)

(72) Inventor: Erwin Satrya Budiman, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 777 days.

(21) Appl. No.: 17/882,860

(22) Filed: Aug. 8, 2022

(65) Prior Publication Data

US 2022/0370021 A1 Nov. 24, 2022

Related U.S. Application Data

(63) Continuation of application No. 15/916,258, filed on Mar. 8, 2018, now Pat. No. 11,406,331, which is a (Continued)

(51) Int. Cl.
*A61B 5/00* (2006.01)
*A61B 5/145* (2006.01)
(Continued)

(52) U.S. Cl.
CPC .............. *A61B 5/746* (2013.01); *A61B 5/002* (2013.01); *A61B 5/0031* (2013.01); *A61B 5/14503* (2013.01); *A61B 5/1451* (2013.01); *A61B 5/14532* (2013.01); *A61B 5/14546* (2013.01); *A61B 5/6849* (2013.01); *A61B 5/7275* (2013.01); *A61B 5/7282* (2013.01); *G16H 20/17* (2018.01); *G16H 40/67* (2018.01)

(58) Field of Classification Search
CPC . A61B 5/746; A61B 5/14503; A61B 5/14546; A61B 5/6849; A61B 5/7282; A61B 5/002; A61B 5/0031; A61B 5/7275; A61B 5/14532; G06F 19/3468; G16H 20/17; G16H 40/67
See application file for complete search history.

(56) References Cited

U.S. PATENT DOCUMENTS 3,581,062 A 5/1971 Aston
3,926,760 A 12/1975 Allen et al.
(Continued)

FOREIGN PATENT DOCUMENTS

EP 0098592 1/1984
EP 0127958 12/1984
(Continued)

OTHER PUBLICATIONS

U.S. Appl. No. 15/916,258 (U.S. Pat. No. 11,406,331), filed Mar. 8, 2018 (Jul. 20, 2022).
(Continued)

*Primary Examiner* — Christian Jang
(74) *Attorney, Agent, or Firm* — Workman Nydegger

(57) ABSTRACT

Methods of determining when to activate an analyte, e.g. glucose, related alarm, such as a hypoglycemia alarm, of a continuous analyte monitor is provided. Also provided are systems, devices and kits.

20 Claims, 6 Drawing Sheets

Related U.S. Application Data continuation of application No. 15/487,365, filed on Apr. 13, 2017, now Pat. No. 9,913,619, which is a continuation of application No. 14/128,583, filed as application No. PCT/US2012/062541 on Oct. 30, 2012, now Pat. No. 9,622,691.

(60) Provisional application No. 61/553,931, filed on Oct. 31, 2011.

(51) Int. Cl.
*G16H 20/17* (2018.01)
*G16H 40/67* (2018.01)

(56) References Cited

U.S. PATENT DOCUMENTS 3,949,388 A 4/1976 Fuller
3,960,497 A 6/1976 Acord et al.
3,978,856 A 9/1976 Michel
4,036,749 A 7/1977 Anderson
4,055,175 A 10/1977 Clemens et al.
4,129,128 A 12/1978 McFarlane
4,245,634 A 1/1981 Albisser et al.
4,327,725 A 5/1982 Cortese et al.
4,344,438 A 8/1982 Schultz
4,349,728 A 9/1982 Phillips et al.
4,373,527 A 2/1983 Fischell
4,392,849 A 7/1983 Petre et al.
4,425,920 A 1/1984 Bourland et al.
4,431,004 A 2/1984 Bessman et al.
4,441,968 A 4/1984 Emmer et al.
4,462,048 A 7/1984 Ross
4,478,976 A 10/1984 Goertz et al.
4,494,950 A 1/1985 Fischell
4,509,531 A 4/1985 Ward
4,527,240 A 7/1985 Kvitash
4,538,616 A 9/1985 Rogoff
4,545,382 A 10/1985 Higgins et al.
4,619,793 A 10/1986 Lee
4,650,547 A 3/1987 Gough
4,671,288 A 6/1987 Gough
4,703,756 A 11/1987 Gough et al.
4,711,245 A 12/1987 Higgins et al.
4,731,051 A 3/1988 Fischell
4,731,726 A 3/1988 Allen, III
4,749,985 A 6/1988 Corsberg
4,750,496 A 6/1988 Reinhart et al.
4,757,022 A 7/1988 Shults et al.
4,759,366 A 7/1988 Callaghan
4,777,953 A 10/1988 Ash et al.
4,779,618 A 10/1988 Mund et al.
4,854,322 A 8/1989 Ash et al.
4,871,351 A 10/1989 Feingold
4,890,620 A 1/1990 Gough
4,925,268 A 5/1990 Iyer et al.
4,947,845 A 8/1990 Davis
4,953,552 A 9/1990 DeMarzo
4,986,271 A 1/1991 Wilkins
4,995,402 A 2/1991 Smith et al.
5,000,180 A 3/1991 Kuypers et al.
5,002,054 A 3/1991 Ash et al.
5,019,974 A 5/1991 Beckers
5,034,112 A 7/1991 Murase et al.
5,050,612 A 9/1991 Matsumura
5,055,171 A 10/1991 Peck
5,068,536 A 11/1991 Rosenthal
5,077,476 A 12/1991 Rosenthal
5,082,550 A 1/1992 Rishpon et al.
5,089,112 A 2/1992 Skotheim et al.
5,106,365 A 4/1992 Hernandez
5,113,869 A 5/1992 Nappholz et al.
5,122,925 A 6/1992 Inpyn
5,135,004 A 8/1992 Adams et al.
5,145,381 A 9/1992 Volz
5,148,812 A 9/1992 Verrier et al.
5,165,407 A 11/1992 Wilson et al.
5,199,428 A 4/1993 Obel et al.
5,202,261 A 4/1993 Musho et al.
5,203,326 A 4/1993 Collins
5,204,264 A 4/1993 Kaminer et al.
5,210,778 A 5/1993 Massart
5,231,988 A 8/1993 Wernicke et al.
5,246,867 A 9/1993 Lakowicz et al.
5,262,035 A 11/1993 Gregg et al.
5,262,305 A 11/1993 Heller et al.
5,264,103 A 11/1993 Yoshioka et al.
5,264,104 A 11/1993 Gregg et al.
5,264,105 A 11/1993 Gregg et al.
5,279,294 A 1/1994 Anderson et al.
5,285,792 A 2/1994 Sjoquist et al.
5,293,877 A 3/1994 O'Hara et al.
5,299,571 A 4/1994 Mastrototaro
5,313,953 A 5/1994 Yomtov et al.
5,320,715 A 6/1994 Berg
5,320,725 A 6/1994 Gregg et al.
5,322,063 A 6/1994 Allen et al.
5,328,460 A 7/1994 Lord et al.
5,330,634 A 7/1994 Wong et al.
5,340,722 A 8/1994 Wolfbeis et al.
5,342,789 A 8/1994 Chick et al.
5,352,351 A 10/1994 White et al.
5,356,786 A 10/1994 Heller et al.
5,360,404 A 11/1994 Novacek et al.
5,365,426 A 11/1994 Siegel et al.
5,372,427 A 12/1994 Padovani et al.
5,376,070 A 12/1994 Purvis et al.
5,379,238 A 1/1995 Stark
5,384,547 A 1/1995 Lynk et al.
5,390,671 A 2/1995 Lord et al.
5,391,250 A 2/1995 Cheney, II et al.
5,400,795 A 3/1995 Murphy et al.
5,408,999 A 4/1995 Singh et al.
5,411,647 A 5/1995 Johnson et al.
5,425,749 A 6/1995 Adams
5,425,868 A 6/1995 Pedersen
5,431,160 A 7/1995 Wilkins
5,431,921 A 7/1995 Thombre
5,438,983 A 8/1995 Falcone
5,462,645 A 10/1995 Albery et al.
5,472,317 A 12/1995 Field et al.
5,489,414 A 2/1996 Schreiber et al.
5,497,772 A 3/1996 Schulman et al.
5,505,828 A 4/1996 Wong et al.
5,507,288 A 4/1996 Bocker et al.
5,509,410 A 4/1996 Hill et al.
5,514,718 A 5/1996 Lewis et al.
5,520,191 A 5/1996 Karlsson et al.
5,531,878 A 7/1996 Vadgama et al.
5,532,686 A 7/1996 Urbas et al.
5,543,326 A 8/1996 Heller et al.
5,552,997 A 9/1996 Massart
5,568,400 A 10/1996 Stark et al.
5,568,806 A 10/1996 Cheney, II et al.
5,569,186 A 10/1996 Lord et al.
5,582,184 A 12/1996 Erickson et al.
5,586,553 A 12/1996 Halili et al.
5,593,852 A 1/1997 Heller et al.
5,601,435 A 2/1997 Quy
5,609,575 A 3/1997 Larson et al.
5,628,310 A 5/1997 Rao et al.
5,628,890 A 5/1997 Carter et al.
5,634,468 A 6/1997 Platt et al.
5,640,954 A 6/1997 Pfeiffer et al.
5,653,239 A 8/1997 Pompei et al.
5,660,163 A 8/1997 Schulman et al.
5,665,222 A 9/1997 Heller et al.
5,695,623 A 12/1997 Michel et al.
5,707,502 A 1/1998 McCaffrey et al.
5,711,001 A 1/1998 Bussan et al.
5,711,861 A 1/1998 Ward et al.
5,720,295 A 2/1998 Greenhut et al.
5,724,030 A 3/1998 Urbas et al.
5,733,259 A 3/1998 Valcke et al.

(56) References Cited

U.S. PATENT DOCUMENTS 5,735,285 A 4/1998 Albert et al.
5,741,211 A 4/1998 Renirie et al.
5,749,907 A 5/1998 Mann
5,772,586 A 6/1998 Heinonen et al.
5,785,660 A 7/1998 van Lake et al.
5,786,439 A 7/1998 Van Antwerp et al.
5,791,344 A 8/1998 Schulman et al.
5,792,065 A 8/1998 Xue et al.
5,804,047 A 9/1998 Karube et al.
5,820,551 A 10/1998 Hill et al.
5,822,715 A 10/1998 Worthington et al.
5,863,400 A 1/1999 Drummond et al.
5,891,047 A 4/1999 Lander et al.
5,891,049 A 4/1999 Cyrus et al.
5,899,855 A 5/1999 Brown
5,914,026 A 6/1999 Blubaugh, Jr. et al.
5,918,603 A 7/1999 Brown
5,925,021 A 7/1999 Castellano et al.
5,935,224 A 8/1999 Svancarek et al.
5,942,979 A 8/1999 Luppino
5,951,485 A 9/1999 Cyrus et al.
5,957,854 A 9/1999 Besson et al.
5,960,797 A 10/1999 Kramer et al.
5,961,451 A 10/1999 Reber et al.
5,964,993 A 10/1999 Blubaugh, Jr. et al.
5,965,380 A 10/1999 Heller et al.
5,971,922 A 10/1999 Arita et al.
5,973,613 A 10/1999 Reis et al.
5,995,860 A 11/1999 Sun et al.
6,001,067 A 12/1999 Shults et al.
6,016,443 A 1/2000 Ekwall et al.
6,021,350 A 2/2000 Mathson
6,024,699 A 2/2000 Surwit et al.
6,038,469 A 3/2000 Karlsson et al.
6,049,727 A 4/2000 Crothall
6,071,391 A 6/2000 Gotoh et al.
6,073,031 A 6/2000 Helstab et al.
6,083,710 A 7/2000 Heller et al.
6,088,608 A 7/2000 Schulman et al.
6,091,976 A 7/2000 Pfeiffer et al.
6,091,987 A 7/2000 Thompson
6,093,172 A 7/2000 Funderburk et al.
6,103,033 A 8/2000 Say et al.
6,108,577 A 8/2000 Benser
6,112,116 A 8/2000 Fischell
6,115,622 A 9/2000 Minoz
6,115,628 A 9/2000 Stadler et al.
6,117,290 A 9/2000 Say et al.
6,119,028 A 9/2000 Schulman et al.
6,120,676 A 9/2000 Heller et al.
6,121,009 A 9/2000 Heller et al.
6,121,611 A 9/2000 Lindsay et al.
6,122,351 A 9/2000 Schlueter, Jr. et al.
6,128,526 A 10/2000 Stadler et al.
6,130,623 A 10/2000 MacLellan et al.
6,134,461 A 10/2000 Say et al.
6,143,164 A 11/2000 Heller et al.
6,144,837 A 11/2000 Quy
6,144,871 A 11/2000 Saito et al.
6,159,147 A 12/2000 Lichter et al.
6,161,095 A 12/2000 Brown
6,162,611 A 12/2000 Heller et al.
6,168,957 B1 1/2001 Matzinger et al.
6,175,752 B1 1/2001 Say et al.
6,200,265 B1 3/2001 Walsh et al.
6,212,416 B1 4/2001 Ward et al.
6,212,417 B1 4/2001 Ikeda et al.
6,219,574 B1 4/2001 Cormier et al.
6,223,283 B1 4/2001 Chaiken et al.
6,233,471 B1 5/2001 Berner et al.
6,233,486 B1 5/2001 Ekwall et al.
6,237,394 B1 5/2001 Harris et al.
6,248,067 B1 6/2001 Causey, III et al.
6,249,705 B1 6/2001 Snell
6,254,586 B1 7/2001 Mann et al.
6,256,538 B1 7/2001 Ekwall
6,264,606 B1 7/2001 Ekwall et al.
6,270,455 B1 8/2001 Brown
6,272,379 B1 8/2001 Fischell et al.
6,275,717 B1 8/2001 Gross et al.
6,283,761 B1 9/2001 Joao
6,284,478 B1 9/2001 Heller et al.
6,291,200 B1 9/2001 LeJeune et al.
6,293,925 B1 9/2001 Safabash et al.
6,294,997 B1 9/2001 Paratore et al.
6,295,506 B1 9/2001 Heinonen et al.
6,299,757 B1 10/2001 Feldman et al.
6,306,104 B1 10/2001 Cunningham et al.
6,309,884 B1 10/2001 Cooper et al.
6,329,161 B1 12/2001 Heller et al.
6,338,790 B1 1/2002 Feldman et al.
6,348,640 B1 2/2002 Navot et al.
6,359,444 B1 3/2002 Grimes
6,360,888 B1 3/2002 McIvor et al.
6,361,503 B1 3/2002 Starobin et al.
6,366,794 B1 4/2002 Moussy et al.
6,368,141 B1 4/2002 VanAntwerp et al.
6,377,828 B1 4/2002 Chaiken et al.
6,377,852 B1 4/2002 Bornzin et al.
6,377,894 B1 4/2002 Deweese et al.
6,379,301 B1 4/2002 Worthington et al.
6,381,493 B1 4/2002 Stadler et al.
6,387,048 B1 5/2002 Schulman et al.
6,400,974 B1 6/2002 Lesho
6,405,066 B1 6/2002 Essenpreis et al.
6,413,393 B1 7/2002 Van Antwerp et al.
6,416,471 B1 7/2002 Kumar et al.
6,418,346 B1 7/2002 Nelson et al.
6,424,847 B1 7/2002 Mastrototaro et al.
6,427,088 B1 7/2002 Bowman, IV et al.
6,440,068 B1 8/2002 Brown et al.
6,461,496 B1 10/2002 Feldman et al.
6,471,689 B1 10/2002 Joseph et al.
6,475,372 B1 11/2002 Ohara et al.
6,475,750 B1 11/2002 Han et al.
6,478,736 B1 11/2002 Mault
6,484,046 B1 11/2002 Say et al.
6,496,729 B2 12/2002 Thompson
6,497,655 B1 12/2002 Linberg et al.
6,501,983 B1 12/2002 Natarajan et al.
6,503,381 B1 1/2003 Gotoh et al.
6,514,460 B1 2/2003 Fendrock
6,514,718 B2 2/2003 Heller et al.
6,520,326 B2 2/2003 McIvor et al.
6,522,903 B1 2/2003 Berman et al.
6,540,891 B1 4/2003 Stewart et al.
6,544,212 B2 4/2003 Galley et al.
6,549,796 B2 4/2003 Sohrab
6,551,494 B1 4/2003 Heller et al.
6,558,320 B1 5/2003 Causey, III et al.
6,558,321 B1 5/2003 Burd et al.
6,558,351 B1 5/2003 Steil et al.
6,560,471 B1 5/2003 Heller et al.
6,561,975 B1 5/2003 Pool et al.
6,561,978 B1 5/2003 Conn et al.
6,562,001 B2 5/2003 Lebel et al.
6,564,105 B2 5/2003 Starkweather et al.
6,565,509 B1 5/2003 Say et al.
6,571,128 B2 5/2003 Lebel et al.
6,572,542 B1 6/2003 Houben et al.
6,574,490 B2 6/2003 Abbink et al.
6,574,510 B2 6/2003 Von Arx et al.
6,576,101 B1 6/2003 Heller et al.
6,577,899 B2 6/2003 Lebel et al.
6,579,231 B1 6/2003 Phipps
6,579,690 B1 6/2003 Bonnecaze et al.
6,585,644 B2 7/2003 Lebel et al.
6,587,704 B1 7/2003 Fine et al.
6,591,125 B1 7/2003 Buse et al.
6,592,745 B1 7/2003 Feldman et al.
6,595,919 B2 7/2003 Berner et al.
6,600,997 B2 7/2003 Deweese et al.
6,605,200 B1 8/2003 Mao et al.
6,605,201 B1 8/2003 Mao et al.

(56) References Cited

U.S. PATENT DOCUMENTS 6,607,509 B2 8/2003 Bobroff et al.
6,610,012 B2 8/2003 Mault
6,616,819 B1 9/2003 Liamos et al.
6,618,934 B1 9/2003 Feldman et al.
6,622,045 B2 9/2003 Snell et al.
6,633,772 B2 10/2003 Ford et al.
6,635,014 B2 10/2003 Starkweather et al.
6,635,167 B1 10/2003 Batman et al.
6,641,533 B2 11/2003 Causey, III et al.
6,648,821 B2 11/2003 Lebel et al.
6,650,471 B2 11/2003 Doi
6,654,625 B1 11/2003 Say et al.
6,656,114 B1 12/2003 Poulson et al.
6,658,396 B1 12/2003 Tang et al.
6,659,948 B2 12/2003 Lebel et al.
6,668,196 B1 12/2003 Villegas et al.
6,675,030 B2 1/2004 Ciuczak et al.
6,676,816 B2 1/2004 Mao et al.
6,687,546 B2 2/2004 Lebel et al.
6,689,056 B1 2/2004 Kilcoyne et al.
6,694,191 B2 2/2004 Starkweather et al.
6,695,860 B1 2/2004 Ward et al.
6,698,269 B2 3/2004 Baber et al.
6,702,857 B2 3/2004 Brauker et al.
6,721,582 B2 4/2004 Trepagnier et al.
6,730,200 B1 5/2004 Stewart et al.
6,731,976 B2 5/2004 Penn et al.
6,731,985 B2 5/2004 Poore et al.
6,733,446 B2 5/2004 Lebel et al.
6,735,183 B2 5/2004 O'Toole et al.
6,736,957 B1 5/2004 Forrow et al.
6,740,075 B2 5/2004 Lebel et al.
6,741,877 B1 5/2004 Shults et al.
6,746,582 B2 6/2004 Heller et al.
6,749,740 B2 6/2004 Liamos et al.
6,758,810 B2 7/2004 Lebel et al.
6,764,581 B1 7/2004 Forrow et al.
6,770,030 B1 8/2004 Schaupp et al.
6,773,671 B1 8/2004 Lewis et al.
6,790,178 B1 9/2004 Mault et al.
6,804,558 B2 10/2004 Haller et al.
6,809,653 B1 10/2004 Mann et al.
6,810,290 B2 10/2004 Lebel et al.
6,811,533 B2 11/2004 Lebel et al.
6,811,534 B2 11/2004 Bowman, IV et al.
6,813,519 B2 11/2004 Lebel et al.
6,835,553 B2 12/2004 Han et al.
6,850,790 B2 2/2005 Berner et al.
6,850,859 B1 2/2005 Schuh
6,862,465 B2 3/2005 Shults et al.
6,865,407 B2 3/2005 Kimball et al.
6,873,268 B2 3/2005 Lebel et al.
6,878,112 B2 4/2005 Linberg et al.
6,881,551 B2 4/2005 Heller et al.
6,882,940 B2 4/2005 Potts et al.
6,892,085 B2 5/2005 McIvor et al.
6,893,545 B2 5/2005 Gotoh et al.
6,895,263 B2 5/2005 Shin et al.
6,895,265 B2 5/2005 Silver
6,912,413 B2 6/2005 Rantala et al.
6,923,763 B1 8/2005 Kovatchev et al.
6,923,764 B2 8/2005 Aceti et al.
6,931,327 B2 8/2005 Goode, Jr. et al.
6,932,892 B2 8/2005 Chen et al.
6,932,894 B2 8/2005 Mao et al.
6,936,006 B2 8/2005 Sabra
6,940,403 B2 9/2005 Kail, IV
6,941,163 B2 9/2005 Ford et al.
6,942,518 B2 9/2005 Liamos et al.
6,950,708 B2 9/2005 Bowman IV et al.
6,954,662 B2 10/2005 Freger et al.
6,958,705 B2 10/2005 Lebel et al.
6,968,294 B2 11/2005 Gutta et al.
6,971,274 B2 12/2005 Olin
6,974,437 B2 12/2005 Lebel et al.
6,990,366 B2 1/2006 Say et al.
6,997,907 B2 2/2006 Safabash et al.
6,998,247 B2 2/2006 Monfre et al.
7,003,336 B2 2/2006 Holker et al.
7,003,340 B2 2/2006 Say et al.
7,003,341 B2 2/2006 Say et al.
7,009,511 B2 3/2006 Mazar et al.
7,010,345 B2 3/2006 Hill et al.
7,011,630 B2 3/2006 Desai et al.
7,016,713 B2 3/2006 Gardner et al.
7,016,720 B2 3/2006 Kroll
7,020,508 B2 3/2006 Stivoric et al.
7,022,072 B2 4/2006 Fox et al.
7,022,219 B2 4/2006 Mansouri et al.
7,024,236 B2 4/2006 Ford et al.
7,024,245 B2 4/2006 Lebel et al.
7,025,425 B2 4/2006 Kovatchev et al.
7,029,443 B2 4/2006 Kroll
7,029,444 B2 4/2006 Shin et al.
7,041,068 B2 5/2006 Freeman et al.
7,041,468 B2 5/2006 Drucker et al.
7,043,287 B1 5/2006 Khalil et al.
7,043,305 B2 5/2006 KenKnight et al.
7,052,472 B1 5/2006 Miller et al.
7,052,483 B2 5/2006 Wojcik
7,056,302 B2 6/2006 Douglas
7,058,453 B2 6/2006 Nelson et al.
7,060,031 B2 6/2006 Webb et al.
7,074,307 B2 7/2006 Simpson et al.
7,076,300 B1 7/2006 Kroll et al.
7,081,195 B2 7/2006 Simpson et al.
7,082,334 B2 7/2006 Boute et al.
7,092,891 B2 8/2006 Maus et al.
7,096,064 B2 8/2006 Deno et al.
7,098,803 B2 8/2006 Mann et al.
7,103,412 B1 9/2006 Kroll
7,108,778 B2 9/2006 Simpson et al.
7,110,803 B2 9/2006 Shults et al.
7,113,821 B1 9/2006 Sun et al.
7,118,667 B2 10/2006 Lee
7,123,950 B2 10/2006 Mannheimer
7,125,382 B2 10/2006 Zhou et al.
7,134,999 B2 11/2006 Brauker et al.
7,136,689 B2 11/2006 Shults et al.
7,142,911 B2 11/2006 Boileau et al.
7,153,265 B2 12/2006 Vachon
7,155,729 B1 12/2006 Andrew et al.
7,167,818 B2 1/2007 Brown
7,171,274 B2 1/2007 Starkweather et al.
7,183,102 B2 2/2007 Monfre et al.
7,190,988 B2 3/2007 Say et al.
7,192,450 B2 3/2007 Brauker et al.
7,198,606 B2 4/2007 Boecker et al.
7,203,549 B2 4/2007 Schommer et al.
7,220,387 B2 5/2007 Flaherty et al.
7,225,535 B2 6/2007 Feldman et al.
7,226,978 B2 6/2007 Tapsak et al.
7,228,182 B2 6/2007 Healy et al.
7,237,712 B2 7/2007 DeRocco et al.
7,258,673 B2 8/2007 Racchini et al.
7,267,665 B2 9/2007 Steil et al.
7,272,436 B2 9/2007 Gill et al.
7,276,029 B2 10/2007 Goode, Jr. et al.
7,278,983 B2 10/2007 Ireland et al.
7,295,867 B2 11/2007 Berner et al.
7,297,114 B2 11/2007 Gill et al.
7,299,082 B2 11/2007 Feldman et al.
7,301,463 B1 11/2007 Paterno
7,310,544 B2 12/2007 Brister et al.
7,317,938 B2 1/2008 Lorenz et al.
7,318,816 B2 1/2008 Bobroff et al.
7,324,850 B2 1/2008 Persen et al.
7,335,294 B2 2/2008 Heller et al.
7,347,819 B2 3/2008 Lebel et al.
7,354,420 B2 4/2008 Steil et al.
7,364,592 B2 4/2008 Carr-Brendel et al.
7,366,556 B2 4/2008 Brister et al.
7,379,765 B2 5/2008 Petisce et al.
7,384,397 B2 6/2008 Zhang et al.

(56) References Cited

U.S. PATENT DOCUMENTS

| | | | |
|---|---|---|---|
| 7,387,010 | B2 | 6/2008 | Sunshine et al. |
| 7,399,277 | B2 | 7/2008 | Saidara et al. |
| 7,402,153 | B2 | 7/2008 | Steil et al. |
| 7,404,796 | B2 | 7/2008 | Ginsberg |
| 7,419,573 | B2 | 9/2008 | Gundel |
| 7,424,318 | B2 | 9/2008 | Brister et al. |
| 7,460,898 | B2 | 12/2008 | Brister et al. |
| 7,467,003 | B2 | 12/2008 | Brister et al. |
| 7,468,125 | B2 | 12/2008 | Kraft et al. |
| 7,471,972 | B2 | 12/2008 | Rhodes et al. |
| 7,474,992 | B2 | 1/2009 | Ariyur |
| 7,491,303 | B2 | 2/2009 | Sakata et al. |
| 7,492,254 | B2 | 2/2009 | Bandy et al. |
| 7,494,465 | B2 | 2/2009 | Brister et al. |
| 7,497,827 | B2 | 3/2009 | Brister et al. |
| 7,499,002 | B2 | 3/2009 | Blasko et al. |
| 7,502,644 | B2 | 3/2009 | Gill et al. |
| 7,519,408 | B2 | 4/2009 | Rasdal et al. |
| 7,519,478 | B2 | 4/2009 | Bartkowiak et al. |
| 7,523,004 | B2 | 4/2009 | Bartkowiak et al. |
| 7,524,287 | B2 | 4/2009 | Bharmi |
| 7,547,281 | B2 | 6/2009 | Hayes et al. |
| 7,565,197 | B2 | 7/2009 | Haubrich et al. |
| 7,569,030 | B2 | 8/2009 | Lebel et al. |
| 7,574,266 | B2 | 8/2009 | Dudding et al. |
| 7,583,990 | B2 | 9/2009 | Goode, Jr. et al. |
| 7,591,801 | B2 | 9/2009 | Brauker et al. |
| 7,599,726 | B2 | 10/2009 | Goode, Jr. et al. |
| 7,602,310 | B2 | 10/2009 | Mann et al. |
| 7,604,178 | B2 | 10/2009 | Stewart |
| 7,613,491 | B2 | 11/2009 | Boock et al. |
| 7,615,007 | B2 | 11/2009 | Shults et al. |
| 7,618,369 | B2 | 11/2009 | Hayter et al. |
| 7,620,438 | B2 | 11/2009 | He |
| 7,630,748 | B2 | 12/2009 | Budiman |
| 7,632,228 | B2 | 12/2009 | Brauker et al. |
| 7,635,594 | B2 | 12/2009 | Holmes et al. |
| 7,637,868 | B2 | 12/2009 | Saint et al. |
| 7,640,048 | B2 | 12/2009 | Dobbles et al. |
| 7,643,798 | B2 | 1/2010 | Ljung |
| 7,659,823 | B1 | 2/2010 | Killian et al. |
| 7,668,596 | B2 | 2/2010 | Von Arx et al. |
| 7,699,775 | B2 | 4/2010 | Desai et al. |
| 7,699,964 | B2 | 4/2010 | Feldman et al. |
| 7,711,493 | B2 | 5/2010 | Bartkowiak et al. |
| 7,736,310 | B2 | 6/2010 | Taub et al. |
| 7,741,734 | B2 | 6/2010 | Joannopoulos et al. |
| 7,751,864 | B2 | 7/2010 | Buck, Jr. |
| 7,766,829 | B2 | 8/2010 | Sloan et al. |
| 7,771,352 | B2 | 8/2010 | Shults et al. |
| 7,774,145 | B2 | 8/2010 | Bruaker et al. |
| 7,778,680 | B2 | 8/2010 | Goode, Jr. et al. |
| 7,779,332 | B2 | 8/2010 | Karr et al. |
| 7,782,192 | B2 | 8/2010 | Jeckelmann et al. |
| 7,783,333 | B2 | 8/2010 | Brister et al. |
| 7,791,467 | B2 | 9/2010 | Mazar et al. |
| 7,792,562 | B2 | 9/2010 | Shults et al. |
| 7,826,981 | B2 | 11/2010 | Goode, Jr. et al. |
| 7,831,310 | B2 | 11/2010 | Lebel et al. |
| 7,857,760 | B2 | 12/2010 | Brister et al. |
| 7,860,574 | B2 | 12/2010 | Von Arx et al. |
| 7,866,026 | B1 | 1/2011 | Wang et al. |
| 7,882,611 | B2 | 2/2011 | Shah et al. |
| 7,885,697 | B2 | 2/2011 | Brister et al. |
| 7,889,069 | B2 | 2/2011 | Fifolt et al. |
| 7,899,511 | B2 | 3/2011 | Shults et al. |
| 7,905,833 | B2 | 3/2011 | Brister et al. |
| 7,912,674 | B2 | 3/2011 | Killoren Clark et al. |
| 7,914,450 | B2 | 3/2011 | Goode, Jr. et al. |
| 7,916,013 | B2 | 3/2011 | Stevenson |
| 7,938,797 | B2 | 5/2011 | Estes |
| 7,946,984 | B2 | 5/2011 | Brister et al. |
| 7,955,258 | B2 | 6/2011 | Goscha et al. |
| 7,970,448 | B2 | 6/2011 | Shults et al. |
| 7,974,672 | B2 | 7/2011 | Shults et al. |
| 7,999,674 | B2 | 8/2011 | Kamen |
| 8,060,173 | B2 | 11/2011 | Goode, Jr. et al. |
| 8,072,310 | B1 | 12/2011 | Everhart |
| 8,090,445 | B2 | 1/2012 | Ginggen |
| 8,093,991 | B2 | 1/2012 | Stevenson et al. |
| 8,094,009 | B2 | 1/2012 | Allen et al. |
| 8,098,159 | B2 | 1/2012 | Batra et al. |
| 8,098,160 | B2 | 1/2012 | Howarth et al. |
| 8,098,161 | B2 | 1/2012 | Lavedas |
| 8,098,201 | B2 | 1/2012 | Choi et al. |
| 8,098,208 | B2 | 1/2012 | Ficker et al. |
| 8,102,021 | B2 | 1/2012 | Degani |
| 8,102,154 | B2 | 1/2012 | Bishop et al. |
| 8,102,263 | B2 | 1/2012 | Yeo et al. |
| 8,102,789 | B2 | 1/2012 | Rosar et al. |
| 8,103,241 | B2 | 1/2012 | Young et al. |
| 8,103,325 | B2 | 1/2012 | Swedlow et al. |
| 8,111,042 | B2 | 2/2012 | Bennett |
| 8,115,488 | B2 | 2/2012 | McDowell |
| 8,116,681 | B2 | 2/2012 | Baarman |
| 8,116,683 | B2 | 2/2012 | Baarman |
| 8,116,837 | B2 | 2/2012 | Huang |
| 8,117,481 | B2 | 2/2012 | Anselmi et al. |
| 8,120,493 | B2 | 2/2012 | Burr |
| 8,124,452 | B2 | 2/2012 | Sheats |
| 8,130,093 | B2 | 3/2012 | Mazar et al. |
| 8,131,351 | B2 | 3/2012 | Kalgren et al. |
| 8,131,365 | B2 | 3/2012 | Zhang et al. |
| 8,131,565 | B2 | 3/2012 | Dicks et al. |
| 8,132,037 | B2 | 3/2012 | Fehr et al. |
| 8,135,352 | B2 | 3/2012 | Langsweirdt et al. |
| 8,136,735 | B2 | 3/2012 | Arai et al. |
| 8,138,925 | B2 | 3/2012 | Downie et al. |
| 8,140,160 | B2 | 3/2012 | Pless et al. |
| 8,140,168 | B2 | 3/2012 | Olson et al. |
| 8,140,299 | B2 | 3/2012 | Siess |
| 8,140,312 | B2 | 3/2012 | Hayter et al. |
| 8,150,321 | B2 | 4/2012 | Winter et al. |
| 8,150,516 | B2 | 4/2012 | Levine et al. |
| 8,160,669 | B2 | 4/2012 | Brauker et al. |
| 8,160,900 | B2 | 4/2012 | Taub et al. |
| 8,170,803 | B2 | 5/2012 | Kamath et al. |
| 8,179,266 | B2 | 5/2012 | Hermle |
| 8,211,016 | B2 | 7/2012 | Budiman |
| 8,216,137 | B2 | 7/2012 | Budiman |
| 8,216,138 | B1 | 7/2012 | McGarraugh et al. |
| 8,224,415 | B2 | 7/2012 | Budiman et al. |
| 8,239,166 | B2 | 8/2012 | Hayter et al. |
| 8,255,026 | B1 | 8/2012 | Al-Ali |
| 8,282,549 | B2 | 10/2012 | Brauker et al. |
| 8,376,945 | B2 | 2/2013 | Hayter et al. |
| 8,396,670 | B2 | 3/2013 | St-Pierre |
| 8,444,560 | B2 | 5/2013 | Hayter et al. |
| 8,457,703 | B2 | 6/2013 | Al-Ali |
| 8,484,005 | B2 | 7/2013 | Hayter et al. |
| 8,532,935 | B2 | 9/2013 | Budiman |
| 8,543,354 | B2 | 9/2013 | Luo et al. |
| 8,571,808 | B2 | 10/2013 | Hayter |
| 8,612,163 | B2 | 12/2013 | Hayter et al. |
| 8,657,746 | B2 | 2/2014 | Roy |
| 8,682,615 | B2 | 3/2014 | Hayter et al. |
| 9,000,914 | B2 | 4/2015 | Baker et al. |
| 9,060,719 | B2 | 6/2015 | Hayter et al. |
| 9,113,828 | B2 | 8/2015 | Budiman |
| 9,119,528 | B2 | 9/2015 | Cobelli et al. |
| 9,398,872 | B2 | 7/2016 | Hayter et al. |
| 9,408,566 | B2 | 8/2016 | Hayter et al. |
| 9,483,608 | B2 | 11/2016 | Hayter et al. |
| 9,558,325 | B2 | 1/2017 | Hayter et al. |
| 9,622,691 | B2 | 4/2017 | Budiman |
| 9,801,541 | B2 | 10/2017 | Mensinger et al. |
| 9,913,619 | B2 | 3/2018 | Budiman |
| 9,980,140 | B1 | 5/2018 | Spencer et al. |
| 10,375,222 | B2 | 8/2019 | Mandapaka et al. |
| 10,702,215 | B2 | 7/2020 | Hampapuram et al. |
| 10,827,954 | B2 | 11/2020 | Hoss et al. |
| 10,855,788 | B2 | 12/2020 | Arabo et al. |
| 10,973,443 | B2 | 4/2021 | Funderburk et al. |
| 10,980,461 | B2 | 4/2021 | Simpson et al. |

(56) References Cited

U.S. PATENT DOCUMENTS 11,000,213 B2 5/2021 Kamath et al.
11,000,216 B2 5/2021 Curry et al.
11,020,031 B1 6/2021 Simpson et al.
11,064,917 B2 7/2021 Simpson et al.
11,141,084 B2 10/2021 Funderburk et al.
11,213,204 B2 1/2022 Mensinger et al.
11,991,175 B2 5/2024 Rolfe et al.
2001/0041831 A1 11/2001 Starkweather et al.
2002/0010390 A1 1/2002 Guice et al.
2002/0016534 A1 2/2002 Trepagnier et al.
2002/0019022 A1 2/2002 Dunn et al.
2002/0042090 A1 4/2002 Heller et al.
2002/0043651 A1 4/2002 Darrow et al.
2002/0065454 A1 5/2002 Lebel et al.
2002/0068860 A1 6/2002 Clark
2002/0072784 A1 6/2002 Sheppard et al.
2002/0103499 A1 8/2002 Perez et al.
2002/0106709 A1 8/2002 Potts et al.
2002/0120186 A1 8/2002 Keimel
2002/0128594 A1 9/2002 Das et al.
2002/0143266 A1 10/2002 Bock
2002/0143372 A1 10/2002 Snell et al.
2002/0161288 A1 10/2002 Shin et al.
2002/0169635 A1 11/2002 Shillingburg
2002/0177764 A1 11/2002 Sohrab
2002/0193679 A1 12/2002 Malave et al.
2003/0003524 A1 1/2003 Taniike et al.
2003/0004403 A1 1/2003 Drinan et al.
2003/0023317 A1 1/2003 Brauker et al.
2003/0023461 A1 1/2003 Quintanilla et al.
2003/0028184 A1 2/2003 Lebel et al.
2003/0032867 A1 2/2003 Crothall et al.
2003/0032874 A1 2/2003 Rhodes et al.
2003/0042137 A1 3/2003 Mao et al.
2003/0050546 A1 3/2003 Desai et al.
2003/0054428 A1 3/2003 Monfre et al.
2003/0065308 A1 4/2003 Lebel et al.
2003/0076082 A1 4/2003 Morgan et al.
2003/0100821 A1 5/2003 Heller et al.
2003/0125612 A1 7/2003 Fox et al.
2003/0130616 A1 7/2003 Steil et al.
2003/0134347 A1 7/2003 Heller et al.
2003/0168338 A1 9/2003 Gao et al.
2003/0176933 A1 9/2003 Lebel et al.
2003/0187338 A1 10/2003 Say et al.
2003/0191377 A1 10/2003 Robinson et al.
2003/0199744 A1 10/2003 Buse et al.
2003/0199790 A1 10/2003 Boecker et al.
2003/0208113 A1 11/2003 Mault et al.
2003/0212317 A1 11/2003 Kovatchev et al.
2003/0212379 A1 11/2003 Bylund et al.
2003/0216630 A1 11/2003 Jersey-Willuhn et al.
2003/0217966 A1 11/2003 Tapsak et al.
2003/0235817 A1 12/2003 Bartkowiak et al.
2004/0010186 A1 1/2004 Kimball et al.
2004/0010207 A1 1/2004 Flaherty et al.
2004/0011671 A1 1/2004 Shults et al.
2004/0018486 A1 1/2004 Dunn et al.
2004/0022438 A1 2/2004 Hibbard
2004/0024553 A1 2/2004 Monfre et al.
2004/0039298 A1 2/2004 Abreu
2004/0040840 A1 3/2004 Mao et al.
2004/0045879 A1 3/2004 Shults et al.
2004/0054263 A1 3/2004 Moerman et al.
2004/0064068 A1 4/2004 DeNuzzio et al.
2004/0077962 A1 4/2004 Kroll
2004/0078065 A1 4/2004 Kroll
2004/0093167 A1 5/2004 Braig et al.
2004/0099529 A1 5/2004 Mao et al.
2004/0106858 A1 6/2004 Say et al.
2004/0122353 A1 6/2004 Shahmirian et al.
2004/0127777 A1 7/2004 Ruchti et al.
2004/0133164 A1 7/2004 Funderburk et al.
2004/0135684 A1 7/2004 Steinthal et al.
2004/0138588 A1 7/2004 Saikley et al.
2004/0138716 A1 7/2004 Kon et al.
2004/0142403 A1 7/2004 Hetzel et al.
2004/0146909 A1 7/2004 Duong et al.
2004/0152622 A1 8/2004 Keith et al.
2004/0162678 A1 8/2004 Hetzel et al.
2004/0167801 A1 8/2004 Say et al.
2004/0171921 A1 9/2004 Say et al.
2004/0172307 A1 9/2004 Gruber
2004/0176672 A1 9/2004 Silver et al.
2004/0186362 A1 9/2004 Brauker et al.
2004/0186365 A1 9/2004 Jin et al.
2004/0193025 A1 9/2004 Steil et al.
2004/0193090 A1 9/2004 Lebel et al.
2004/0197846 A1 10/2004 Hockersmith et al.
2004/0199056 A1 10/2004 Husemann et al.
2004/0199059 A1 10/2004 Brauker et al.
2004/0204687 A1 10/2004 Mogensen et al.
2004/0208780 A1 10/2004 Faries, Jr. et al.
2004/0225338 A1 11/2004 Lebel et al.
2004/0236200 A1 11/2004 Say et al.
2004/0244151 A1 12/2004 Sakata et al.
2004/0249253 A1 12/2004 Racchini et al.
2004/0249420 A1 12/2004 Olson et al.
2004/0254433 A1 12/2004 Bandis et al.
2004/0254434 A1 12/2004 Goodnow et al.
2004/0260478 A1 12/2004 Schwamm
2004/0263354 A1 12/2004 Mann et al.
2004/0267300 A1 12/2004 Mace
2005/0003470 A1 1/2005 Nelson et al.
2005/0004439 A1 1/2005 Shin et al.
2005/0004494 A1 1/2005 Perez et al.
2005/0010087 A1 1/2005 Banet et al.
2005/0010269 A1 1/2005 Lebel et al.
2005/0016276 A1 1/2005 Guan et al.
2005/0017864 A1 1/2005 Tsoukalis
2005/0020892 A1* 1/2005 Acosta ................ A61B 5/4872 600/316
2005/0027177 A1 2/2005 Shin et al.
2005/0027180 A1 2/2005 Goode, Jr. et al.
2005/0027181 A1 2/2005 Goode et al.
2005/0027462 A1 2/2005 Goode et al.
2005/0027463 A1 2/2005 Goode et al.
2005/0031689 A1 2/2005 Shults et al.
2005/0038332 A1 2/2005 Saidara et al.
2005/0043598 A1 2/2005 Goode, Jr. et al.
2005/0049179 A1 3/2005 Davidson et al.
2005/0049473 A1 3/2005 Desai et al.
2005/0059871 A1 3/2005 Gough et al.
2005/0069892 A1 3/2005 Iyengar et al.
2005/0070774 A1 3/2005 Addison et al.
2005/0090607 A1 4/2005 Tapsak et al.
2005/0096511 A1 5/2005 Fox et al.
2005/0096512 A1 5/2005 Fox et al.
2005/0112169 A1 5/2005 Brauker et al.
2005/0113653 A1 5/2005 Fox et al.
2005/0114068 A1 5/2005 Chey et al.
2005/0115832 A1 6/2005 Simpson et al.
2005/0121322 A1 6/2005 Say et al.
2005/0131346 A1 6/2005 Douglas
2005/0143635 A1 6/2005 Kamath et al.
2005/0143636 A1 6/2005 Zhang et al.
2005/0148890 A1 7/2005 Hastings
2005/0151976 A1 7/2005 Toma
2005/0154271 A1 7/2005 Rasdal et al.
2005/0176136 A1 8/2005 Burd et al.
2005/0177398 A1 8/2005 Watanabe et al.
2005/0182306 A1 8/2005 Sloan
2005/0187720 A1 8/2005 Goode, Jr. et al.
2005/0192494 A1 9/2005 Ginsberg
2005/0192557 A1 9/2005 Brauker et al.
2005/0195930 A1 9/2005 Spital et al.
2005/0196821 A1 9/2005 Monfre et al.
2005/0199494 A1 9/2005 Say et al.
2005/0203360 A1 9/2005 Brauker et al.
2005/0214892 A1 9/2005 Kovatchev et al.
2005/0215871 A1 9/2005 Feldman et al.
2005/0239154 A1 10/2005 Feldman et al.
2005/0239156 A1 10/2005 Drucker et al.
2005/0241957 A1 11/2005 Mao et al.

(56) References Cited

U.S. PATENT DOCUMENTS

2005/0245795 A1 11/2005 Goode, Jr. et al.
2005/0245799 A1 11/2005 Brauker et al.
2005/0245839 A1 11/2005 Stivoric et al.
2005/0245904 A1 11/2005 Estes et al.
2005/0277164 A1 12/2005 Drucker et al.
2005/0277912 A1 12/2005 John
2005/0283208 A1 12/2005 Von Arx et al.
2005/0287620 A1 12/2005 Heller et al.
2005/0288725 A1 12/2005 Hettrick et al.
2006/0001538 A1 1/2006 Kraft et al.
2006/0004270 A1 1/2006 Bedard et al.
2006/0010098 A1 1/2006 Goodnow et al.
2006/0015020 A1 1/2006 Neale et al.
2006/0015024 A1 1/2006 Brister et al.
2006/0016700 A1 1/2006 Brister et al.
2006/0017923 A1 1/2006 Ruchti et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0025662 A1 2/2006 Buse et al.
2006/0025663 A1 2/2006 Talbot et al.
2006/0029177 A1 2/2006 Cranford, Jr. et al.
2006/0031094 A1 2/2006 Cohen et al.
2006/0036139 A1 2/2006 Brister et al.
2006/0036140 A1 2/2006 Brister et al.
2006/0036141 A1 2/2006 Kamath et al.
2006/0036142 A1 2/2006 Brister et al.
2006/0036143 A1 2/2006 Brister et al.
2006/0036144 A1 2/2006 Brister et al.
2006/0036145 A1 2/2006 Brister et al.
2006/0058588 A1 3/2006 Zdeblick
2006/0091006 A1 5/2006 Wang et al.
2006/0094944 A1 5/2006 Chuang
2006/0094945 A1 5/2006 Barman et al.
2006/0142651 A1 6/2006 Brister et al.
2006/0155180 A1 7/2006 Brister et al.
2006/0166629 A1 7/2006 Reggiardo
2006/0167365 A1 7/2006 Bharmi
2006/0167517 A1 7/2006 Gill et al.
2006/0167518 A1 7/2006 Gill et al.
2006/0167519 A1 7/2006 Gill et al.
2006/0173260 A1 8/2006 Gaoni et al.
2006/0173406 A1 8/2006 Hayes et al.
2006/0173444 A1 8/2006 Choy et al.
2006/0183984 A1 8/2006 Dobbles et al.
2006/0183985 A1 8/2006 Brister et al.
2006/0189851 A1 8/2006 Tvig et al.
2006/0189863 A1 8/2006 Peyser et al.
2006/0193375 A1 8/2006 Lee
2006/0222566 A1 10/2006 Brauker et al.
2006/0224109 A1 10/2006 Steil et al.
2006/0226985 A1 10/2006 Goodnow et al.
2006/0229512 A1 10/2006 Petisce et al.
2006/0247508 A1 11/2006 Fennell
2006/0247685 A1 11/2006 Bharmi
2006/0247710 A1 11/2006 Goetz et al.
2006/0247985 A1 11/2006 Liamos et al.
2006/0258929 A1 11/2006 Goode, Jr. et al.
2006/0258959 A1 11/2006 Sode
2006/0264785 A1 11/2006 Dring et al.
2006/0272652 A1 12/2006 Stocker et al.
2006/0276771 A1 12/2006 Galley et al.
2006/0281985 A1 12/2006 Ward et al.
2006/0287691 A1 12/2006 Drew
2006/0293576 A1 12/2006 Van Antwerp et al.
2007/0016381 A1 1/2007 Kamath et al.
2007/0027381 A1 2/2007 Stafford
2007/0032706 A1 2/2007 Kamath et al.
2007/0033074 A1 2/2007 Nitzan et al.
2007/0038044 A1 2/2007 Dobbles et al.
2007/0055799 A1 3/2007 Koehler et al.
2007/0056858 A1 3/2007 Chen et al.
2007/0060803 A1 3/2007 Liljeryd et al.
2007/0060814 A1 3/2007 Stafford
2007/0066873 A1 3/2007 Kamath et al.
2007/0068807 A1 3/2007 Feldman et al.
2007/0071681 A1 3/2007 Gadkar et al.
2007/0073129 A1 3/2007 Shah et al.
2007/0078320 A1 4/2007 Stafford
2007/0078321 A1 4/2007 Mazza et al.
2007/0078322 A1 4/2007 Stafford
2007/0078323 A1 4/2007 Reggiardo et al.
2007/0095661 A1 5/2007 Wang et al.
2007/0106135 A1 5/2007 Sloan et al.
2007/0108048 A1 5/2007 Wang et al.
2007/0118030 A1 5/2007 Bruce et al.
2007/0118405 A1 5/2007 Campbell et al.
2007/0124002 A1 5/2007 Estes et al.
2007/0129621 A1 6/2007 Kellogg et al.
2007/0149875 A1 6/2007 Ouyang et al.
2007/0156033 A1 7/2007 Causey, III et al.
2007/0163880 A1 7/2007 Woo et al.
2007/0168224 A1 7/2007 Letzt et al.
2007/0173706 A1 7/2007 Neinast et al.
2007/0173709 A1 7/2007 Petisce et al.
2007/0173710 A1 7/2007 Petisce et al.
2007/0173761 A1 7/2007 Kanderian et al.
2007/0179349 A1 8/2007 Hoyme et al.
2007/0179352 A1 8/2007 Randlov et al.
2007/0179434 A1 8/2007 Weinert et al.
2007/0191701 A1 8/2007 Feldman et al.
2007/0199818 A1 8/2007 Petyt et al.
2007/0202562 A1 8/2007 Curry et al.
2007/0203407 A1 8/2007 Hoss et al.
2007/0203966 A1 8/2007 Brauker et al.
2007/0208244 A1 9/2007 Brauker et al.
2007/0213657 A1 9/2007 Jennewine et al.
2007/0227911 A1 10/2007 Wang et al.
2007/0232877 A1 10/2007 He
2007/0232878 A1 10/2007 Kovatchev et al.
2007/0232880 A1 10/2007 Siddiqui et al.
2007/0233013 A1 10/2007 Schoenberg et al.
2007/0235331 A1 10/2007 Simpson et al.
2007/0244383 A1 10/2007 Talbot et al.
2007/0249922 A1 10/2007 Peyser et al.
2007/0253021 A1 11/2007 Mehta et al.
2007/0255116 A1 11/2007 Mehta et al.
2007/0255321 A1 11/2007 Gerber et al.
2007/0255531 A1 11/2007 Drew
2007/0258395 A1 11/2007 Jollota et al.
2007/0270672 A1 11/2007 Hayter
2007/0282299 A1 12/2007 Hellwig
2007/0285238 A1 12/2007 Batra
2007/0299617 A1 12/2007 Willis
2008/0004515 A1 1/2008 Jennewine et al.
2008/0004601 A1 1/2008 Jennewine et al.
2008/0009692 A1 1/2008 Stafford
2008/0012701 A1 1/2008 Kass et al.
2008/0017522 A1 1/2008 Heller et al.
2008/0018433 A1 1/2008 Pitt-Pladdy
2008/0021666 A1 1/2008 Goode, Jr. et al.
2008/0021972 A1 1/2008 Huelskamp et al.
2008/0029391 A1 2/2008 Mao et al.
2008/0030369 A1 2/2008 Mann et al.
2008/0033254 A1 2/2008 Kamath et al.
2008/0039702 A1 2/2008 Hayter et al.
2008/0045824 A1 2/2008 Tapsak et al.
2008/0058625 A1 3/2008 McGarraugh et al.
2008/0064937 A1 3/2008 McGarraugh et al.
2008/0064943 A1 3/2008 Talbot et al.
2008/0066305 A1 3/2008 Wang et al.
2008/0071156 A1 3/2008 Brister et al.
2008/0071157 A1 3/2008 McGarraugh et al.
2008/0071158 A1 3/2008 McGarraugh et al.
2008/0071328 A1 3/2008 Haubrich et al.
2008/0081977 A1 4/2008 Hayter et al.
2008/0083617 A1 4/2008 Simpson et al.
2008/0086042 A1 4/2008 Brister et al.
2008/0086044 A1 4/2008 Brister et al.

(56) References Cited

U.S. PATENT DOCUMENTS

2008/0086273 A1 4/2008 Shults et al.
2008/0097289 A1 4/2008 Steil et al.
2008/0102441 A1 5/2008 Chen et al.
2008/0103447 A1 5/2008 Reggiardo et al.
2008/0108942 A1 5/2008 Brister et al.
2008/0119703 A1 5/2008 Brister et al.
2008/0119705 A1 5/2008 Patel et al.
2008/0119708 A1 5/2008 Budiman
2008/0119710 A1 5/2008 Reggiardo et al.
2008/0139910 A1 6/2008 Mastrototaro et al.
2008/0148873 A1 6/2008 Wang
2008/0154099 A1 6/2008 Aspel et al.
2008/0154513 A1 6/2008 Kovatchev et al.
2008/0161666 A1 7/2008 Feldman et al.
2008/0167543 A1 7/2008 Say et al.
2008/0167572 A1 7/2008 Stivoric et al.
2008/0172205 A1 7/2008 Breton et al.
2008/0177149 A1 7/2008 Weinert et al.
2008/0177165 A1 7/2008 Blomquist et al.
2008/0183060 A1 7/2008 Steil et al.
2008/0183061 A1 7/2008 Goode et al.
2008/0183399 A1 7/2008 Goode et al.
2008/0188731 A1 8/2008 Brister et al.
2008/0188796 A1 8/2008 Steil et al.
2008/0189051 A1 8/2008 Goode et al.
2008/0194934 A1 8/2008 Ray et al.
2008/0194935 A1 8/2008 Brister et al.
2008/0194936 A1 8/2008 Goode et al.
2008/0194937 A1 8/2008 Goode et al.
2008/0194938 A1 8/2008 Brister et al.
2008/0195232 A1 8/2008 Carr-Brendel et al.
2008/0195967 A1 8/2008 Goode et al.
2008/0197024 A1 8/2008 Simpson et al.
2008/0200788 A1 8/2008 Brister et al.
2008/0200789 A1 8/2008 Brister et al.
2008/0200791 A1 8/2008 Simpson et al.
2008/0201325 A1 8/2008 Doniger et al.
2008/0208025 A1 8/2008 Shults et al.
2008/0208113 A1 8/2008 Damiano et al.
2008/0214910 A1 9/2008 Buck
2008/0214915 A1 9/2008 Brister et al.
2008/0214918 A1 9/2008 Brister et al.
2008/0228051 A1 9/2008 Shults et al.
2008/0228054 A1 9/2008 Shults et al.
2008/0234943 A1 9/2008 Ray et al.
2008/0234992 A1 9/2008 Ray et al.
2008/0235469 A1 9/2008 Drew
2008/0242961 A1 10/2008 Brister et al.
2008/0242963 A1 10/2008 Essenpreis et al.
2008/0255434 A1 10/2008 Hayter et al.
2008/0255437 A1 10/2008 Hayter
2008/0255438 A1 10/2008 Saidara et al.
2008/0255808 A1 10/2008 Hayter
2008/0256048 A1 10/2008 Hayter
2008/0262469 A1 10/2008 Brister et al.
2008/0267823 A1 10/2008 Wang et al.
2008/0275313 A1 11/2008 Brister et al.
2008/0278332 A1 11/2008 Fennel et al.
2008/0278333 A1 11/2008 Fennell et al.
2008/0287761 A1 11/2008 Hayter
2008/0287762 A1 11/2008 Hayter
2008/0287763 A1 11/2008 Hayter
2008/0287764 A1 11/2008 Rasdal et al.
2008/0287765 A1 11/2008 Rasdal et al.
2008/0287766 A1 11/2008 Rasdal et al.
2008/0288180 A1 11/2008 Hayter
2008/0288204 A1 11/2008 Hayter et al.
2008/0296155 A1 12/2008 Shults et al.
2008/0300572 A1 12/2008 Rankers et al.
2008/0306368 A1 12/2008 Goode et al.
2008/0306434 A1 12/2008 Dobbles et al.
2008/0306435 A1 12/2008 Kamath et al.
2008/0306444 A1 12/2008 Brister et al.
2008/0312518 A1 12/2008 Jina et al.
2008/0312841 A1 12/2008 Hayter
2008/0312842 A1 12/2008 Hayter et al.
2008/0312844 A1 12/2008 Hayter et al.
2008/0312845 A1 12/2008 Hayter et al.
2008/0314395 A1 12/2008 Kovatchev et al.
2008/0319279 A1 12/2008 Ramsay et al.
2008/0319295 A1 12/2008 Bernstein et al.
2008/0319296 A1 12/2008 Bernstein et al.
2009/0005665 A1 1/2009 Hayter et al.
2009/0005666 A1 1/2009 Shin et al.
2009/0006034 A1 1/2009 Hayter et al.
2009/0006061 A1 1/2009 Thukral et al.
2009/0006133 A1 1/2009 Weinert et al.
2009/0012376 A1 1/2009 Agus
2009/0012379 A1 1/2009 Goode et al.
2009/0018424 A1 1/2009 Kamath et al.
2009/0018425 A1 1/2009 Ouyang et al.
2009/0030293 A1 1/2009 Cooper et al.
2009/0030294 A1 1/2009 Petisce et al.
2009/0030641 A1 1/2009 Fjield et al.
2009/0033482 A1 2/2009 Hayter et al.
2009/0036747 A1 2/2009 Hayter et al.
2009/0036758 A1 2/2009 Brauker et al.
2009/0036760 A1 2/2009 Hayter
2009/0036763 A1 2/2009 Brauker et al.
2009/0043181 A1 2/2009 Brauker et al.
2009/0043182 A1 2/2009 Brauker et al.
2009/0043525 A1 2/2009 Brauker et al.
2009/0043541 A1 2/2009 Brauker et al.
2009/0043542 A1 2/2009 Brauker et al.
2009/0045055 A1 2/2009 Rhodes et al.
2009/0048503 A1 2/2009 Dalal et al.
2009/0054737 A1 2/2009 Magar et al.
2009/0054745 A1 2/2009 Jennewine et al.
2009/0054748 A1 2/2009 Feldman et al.
2009/0054749 A1 2/2009 He
2009/0054753 A1 2/2009 Robinson et al.
2009/0055149 A1 2/2009 Hayter et al.
2009/0062633 A1 3/2009 Brauker et al.
2009/0062635 A1 3/2009 Brauker et al.
2009/0062767 A1 3/2009 VanAntwerp et al.
2009/0063402 A1 3/2009 Hayter
2009/0069649 A1 3/2009 Budiman
2009/0076356 A1 3/2009 Simpson et al.
2009/0076360 A1 3/2009 Brister et al.
2009/0076361 A1 3/2009 Kamath et al.
2009/0082693 A1 3/2009 Stafford
2009/0085768 A1 4/2009 Patel et al.
2009/0099436 A1 4/2009 Brister et al.
2009/0102678 A1 4/2009 Mazza et al.
2009/0105554 A1 4/2009 Stahmann et al.
2009/0105560 A1 4/2009 Solomon
2009/0105570 A1 4/2009 Sloan et al.
2009/0105636 A1 4/2009 Hayter et al.
2009/0112478 A1 4/2009 Mueller, Jr. et al.
2009/0112626 A1 4/2009 Talbot et al.
2009/0118589 A1 5/2009 Ueshima et al.
2009/0124877 A1 5/2009 Goode, Jr. et al.
2009/0124878 A1 5/2009 Goode et al.
2009/0124879 A1 5/2009 Brister et al.
2009/0124964 A1 5/2009 Leach et al.
2009/0131768 A1 5/2009 Simpson et al.
2009/0131769 A1 5/2009 Leach et al.
2009/0131776 A1 5/2009 Simpson et al.
2009/0131777 A1 5/2009 Simpson et al.
2009/0137886 A1 5/2009 Shariati et al.
2009/0137887 A1 5/2009 Shariati et al.
2009/0143659 A1 6/2009 Li et al.
2009/0143660 A1 6/2009 Brister et al.
2009/0143725 A1 6/2009 Peyser et al.
2009/0149728 A1 6/2009 Van Antwerp et al.
2009/0150186 A1 6/2009 Cohen et al.
2009/0156919 A1 6/2009 Brister et al.
2009/0156924 A1 6/2009 Shariati et al.
2009/0163789 A1 6/2009 Say et al.
2009/0163790 A1 6/2009 Brister et al.
2009/0163791 A1 6/2009 Brister et al.
2009/0163855 A1 6/2009 Shin et al.
2009/0164190 A1 6/2009 Hayter
2009/0164239 A1 6/2009 Hayter et al.

(56) References Cited

U.S. PATENT DOCUMENTS

2009/0164251 A1 6/2009 Hayter
2009/0178459 A1 7/2009 Li et al.
2009/0182217 A1 7/2009 Li et al.
2009/0182517 A1 7/2009 Gandhi et al.
2009/0189738 A1 7/2009 Hermle
2009/0192366 A1 7/2009 Mensinger et al.
2009/0192380 A1 7/2009 Shariati et al.
2009/0192722 A1 7/2009 Shariati et al.
2009/0192724 A1 7/2009 Brauker et al.
2009/0192745 A1 7/2009 Kamath et al.
2009/0192751 A1 7/2009 Kamath et al.
2009/0198118 A1 8/2009 Hayter et al.
2009/0203981 A1 8/2009 Brauker et al.
2009/0204341 A1 8/2009 Brauker et al.
2009/0216103 A1 8/2009 Brister et al.
2009/0234200 A1 9/2009 Husheer
2009/0240120 A1 9/2009 Mensinger et al.
2009/0240128 A1 9/2009 Mensinger et al.
2009/0240193 A1 9/2009 Mensinger et al.
2009/0242399 A1 10/2009 Kamath et al.
2009/0242425 A1 10/2009 Kamath et al.
2009/0247848 A1* 10/2009 Baker, Jr. ............. A61B 5/7221 600/323
2009/0247855 A1 10/2009 Boock et al.
2009/0247856 A1 10/2009 Boock et al.
2009/0247857 A1 10/2009 Harper et al.
2009/0253973 A1 10/2009 Bashan et al.
2009/0257911 A1 10/2009 Thomas et al.
2009/0267765 A1 10/2009 Greene et al.
2009/0275815 A1 11/2009 Bickoff et al.
2009/0281407 A1 11/2009 Budiman
2009/0287073 A1 11/2009 Boock et al.
2009/0287074 A1 11/2009 Shults et al.
2009/0289796 A1 11/2009 Blumberg
2009/0291634 A1 11/2009 Saarisalo
2009/0294277 A1 12/2009 Thomas et al.
2009/0299155 A1 12/2009 Yang et al.
2009/0299156 A1 12/2009 Simpson et al.
2009/0299162 A1 12/2009 Brauker et al.
2009/0299276 A1 12/2009 Brauker et al.
2010/0010324 A1 1/2010 Brauker et al.
2010/0010331 A1 1/2010 Brauker et al.
2010/0010332 A1 1/2010 Brauker et al.
2010/0045425 A1 2/2010 Chivallier
2010/0057040 A1 3/2010 Hayter
2010/0057041 A1 3/2010 Hayter
2010/0057042 A1 3/2010 Hayter
2010/0057044 A1 3/2010 Hayter
2010/0057057 A1 3/2010 Hayter et al.
2010/0063372 A1 3/2010 Potts et al.
2010/0064764 A1 3/2010 Hayter et al.
2010/0081906 A1 4/2010 Hayter et al.
2010/0081909 A1 4/2010 Budiman et al.
2010/0081953 A1 4/2010 Syeda-Mahmood et al.
2010/0121167 A1 5/2010 McGarraugh et al.
2010/0141656 A1 6/2010 Krieftewirth
2010/0152561 A1 6/2010 Goodnow et al.
2010/0160759 A1 6/2010 Celentano et al.
2010/0168538 A1 7/2010 Keenan et al.
2010/0168546 A1 7/2010 Kamath et al.
2010/0174266 A1 7/2010 Estes
2010/0190435 A1 7/2010 Cook et al.
2010/0191085 A1 7/2010 Budiman
2010/0191472 A1 7/2010 Doniger et al.
2010/0198034 A1 8/2010 Thomas et al.
2010/0198142 A1 8/2010 Sloan et al.
2010/0198314 A1 8/2010 Wei
2010/0204557 A1 8/2010 Kiaie et al.
2010/0213057 A1 8/2010 Feldman et al.
2010/0230285 A1 9/2010 Hoss et al.
2010/0234710 A1 9/2010 Budiman et al.
2010/0261987 A1 10/2010 Kamath et al.
2010/0265073 A1 10/2010 Harper et al.
2010/0268157 A1 10/2010 Wehba et al.
2010/0274515 A1 10/2010 Hoss et al.
2010/0277342 A1 11/2010 Sicurello et al.
2010/0280441 A1 11/2010 Willinska et al.
2010/0280782 A1 11/2010 Harper et al.
2010/0295686 A1* 11/2010 Sloan .................. A61B 5/4839 703/2
2010/0312176 A1 12/2010 Lauer et al.
2010/0313105 A1 12/2010 Nekoomaram et al.
2010/0317952 A1* 12/2010 Budiman ............. A61B 5/4839 600/365
2010/0324392 A1 12/2010 Yee et al.
2010/0326842 A1 12/2010 Mazza et al.
2011/0004276 A1 1/2011 Blair et al.
2011/0021889 A1 1/2011 Hoss et al.
2011/0024043 A1 2/2011 Boock et al.
2011/0024307 A1 2/2011 Simpson et al.
2011/0027127 A1 2/2011 Simpson et al.
2011/0027453 A1 2/2011 Boock et al.
2011/0027458 A1 2/2011 Boock et al.
2011/0028815 A1 2/2011 Simpson et al.
2011/0028816 A1 2/2011 Simpson et al.
2011/0029247 A1 2/2011 Kalathil
2011/0040163 A1 2/2011 Telson et al.
2011/0058485 A1 3/2011 Sloan
2011/0060530 A1 3/2011 Fennell
2011/0077490 A1 3/2011 Simpson et al.
2011/0077494 A1 3/2011 Doniger et al.
2011/0081726 A1 4/2011 Berman et al.
2011/0082484 A1 4/2011 Saravia et al.
2011/0105873 A1 5/2011 Feldman et al.
2011/0106011 A1 5/2011 Cinar et al.
2011/0106126 A1 5/2011 Love et al.
2011/0112696 A1 5/2011 Yodfat et al.
2011/0148905 A1 6/2011 Simmons et al.
2011/0152637 A1 6/2011 Kateraas et al.
2011/0173308 A1 7/2011 Gutekunst
2011/0178717 A1 7/2011 Goodnow et al.
2011/0184267 A1 7/2011 Duke et al.
2011/0184268 A1 7/2011 Taub
2011/0190603 A1 8/2011 Stafford
2011/0191044 A1 8/2011 Stafford
2011/0193704 A1 8/2011 Harper et al.
2011/0202495 A1 8/2011 Gawlick
2011/0208027 A1 8/2011 Wagner et al.
2011/0208155 A1 8/2011 Palerm et al.
2011/0210830 A1 9/2011 Talty et al.
2011/0213225 A1 9/2011 Bernstein et al.
2011/0224523 A1 9/2011 Budiman
2011/0228098 A1* 9/2011 Lamb ...................... G01S 17/86 348/169
2011/0257495 A1 10/2011 Hoss et al.
2011/0257895 A1 10/2011 Brauker et al.
2011/0263958 A1 10/2011 Brauker et al.
2011/0288574 A1 11/2011 Curry et al.
2011/0319729 A1 12/2011 Donnay et al.
2011/0320130 A1 12/2011 Valdes et al.
2011/0320167 A1 12/2011 Budiman
2012/0010642 A1 1/2012 Lee et al.
2012/0078071 A1 3/2012 Bohm et al.
2012/0084053 A1 4/2012 Yuen et al.
2012/0108931 A1 5/2012 Taub
2012/0108934 A1 5/2012 Valdes et al.
2012/0165626 A1 6/2012 Irina et al.
2012/0165640 A1 6/2012 Galley et al.
2012/0173200 A1 7/2012 Breton et al.
2012/0209099 A1 8/2012 Ljuhs et al.
2012/0215462 A1 8/2012 Goode et al.
2012/0233679 A1 9/2012 Shedrinsky
2012/0238851 A1 9/2012 Kamen et al.
2012/0245447 A1 9/2012 Karan et al.
2012/0255875 A1 10/2012 Vicente et al.
2012/0277565 A1 11/2012 Budiman
2012/0283542 A1 11/2012 McGarraugh
2012/0309302 A1 12/2012 Buhot
2012/0313785 A1 12/2012 Hanson et al.
2013/0035575 A1 2/2013 Mayou et al.
2013/0109944 A1 5/2013 Sparacino et al.
2013/0137953 A1 5/2013 Harper et al.
2013/0184547 A1 7/2013 Taub et al.
2013/0231541 A1 9/2013 Hayter et al.

(56) References Cited

U.S. PATENT DOCUMENTS

| | | | |
|---|---|---|---|
| 2013/0324823 | A1 | 12/2013 | Koski et al. |
| 2014/0005499 | A1 | 1/2014 | Catt et al. |
| 2014/0012511 | A1 | 1/2014 | Mensinger et al. |
| 2014/0046160 | A1 | 2/2014 | Terashima et al. |
| 2014/0088392 | A1 | 3/2014 | Bernstein et al. |
| 2014/0121480 | A1 | 5/2014 | Budiman et al. |
| 2014/0121488 | A1 | 5/2014 | Budiman |
| 2014/0221966 | A1 | 8/2014 | Buckingham et al. |
| 2014/0266785 | A1 | 9/2014 | Miller et al. |
| 2014/0313052 | A1 | 10/2014 | Yarger et al. |
| 2014/0379273 | A1 | 12/2014 | Petisce et al. |
| 2015/0005601 | A1 | 1/2015 | Hoss et al. |
| 2015/0123810 | A1 | 5/2015 | Hernandez-Rosas et al. |
| 2015/0205947 | A1 | 7/2015 | Berman et al. |
| 2015/0207796 | A1 | 7/2015 | Love et al. |
| 2015/0241407 | A1 | 8/2015 | Ou et al. |
| 2015/0366510 | A1 | 12/2015 | Budiman |
| 2019/0274598 | A1 | 9/2019 | Scott et al. |

FOREIGN PATENT DOCUMENTS

| | | |
|---|---|---|
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1 391 728 | 2/2004 |
| EP | 1419731 | 5/2004 |
| EP | 0939602 | 9/2004 |
| EP | 1850909 | 4/2010 |
| EP | 1677668 | 7/2010 |
| EP | 1 413 879 | 1/2012 |
| EP | 2 498 196 | 9/2012 |
| EP | 3 575 796 | 12/2019 |
| EP | 3 210 137 B1 | 3/2021 |
| EP | 2914159 B1 | 4/2021 |
| EP | 2939158 | 3/2022 |
| WO | WO-1996/025089 | 8/1996 |
| WO | WO-1996/035370 | 11/1996 |
| WO | WO 97/18639 | 5/1997 |
| WO | WO-1997/015227 | 5/1997 |
| WO | WO 00/49941 | 8/2000 |
| WO | WO-2000/049940 | 8/2000 |
| WO | WO-2000/059370 | 10/2000 |
| WO | WO-2000/074753 | 12/2000 |
| WO | WO-2001/052935 | 7/2001 |
| WO | WO-2001/054753 | 8/2001 |
| WO | WO-2002/016905 | 2/2002 |
| WO | WO 02/058537 | 8/2002 |
| WO | WO 03/012422 | 2/2003 |
| WO | WO 03/032411 | 4/2003 |
| WO | WO-2003/076893 | 9/2003 |
| WO | WO-2003/082091 | 10/2003 |
| WO | WO 03/094714 | 11/2003 |
| WO | WO-2004/060455 | 7/2004 |
| WO | WO-2005/010756 | 2/2005 |
| WO | WO 2005/011489 | 2/2005 |
| WO | WO 2005/065538 | 7/2005 |
| WO | WO-2005/065542 | 7/2005 |
| WO | WO 2005/070287 | 8/2005 |
| WO | WO 2005/121785 | 12/2005 |
| WO | WO-2006/024671 | 3/2006 |
| WO | WO 2006/026741 A1 | 3/2006 |
| WO | WO-2006/081336 | 8/2006 |
| WO | WO-2007/097754 | 8/2007 |
| WO | WO-2008/001366 | 1/2008 |
| WO | WO 2008/021913 | 2/2008 |
| WO | WO-2008/086541 | 7/2008 |
| WO | WO-2010/022387 | 2/2010 |
| WO | WO 2010/099507 | 9/2010 |
| WO | WO 2011/011643 | 1/2011 |
| WO | WO 2012/142502 | 10/2012 |
| WO | WO 2012/154286 | 11/2012 |
| WO | WO 2013/019225 | 2/2013 |
| WO | WO 2014/070456 | 5/2014 |
| WO | WO 2015/069797 | 5/2015 |
| WO | WO 2016/092448 | 6/2016 |

OTHER PUBLICATIONS

U.S. Appl. No. 15/487,365 (U.S. Pat. No. 9,913,619, filed Apr. 13, 2017 (Feb. 21, 2018).

U.S. Appl. No. 14/128,583 (U.S. Pat. No. 9,622,691, filed Dec. 20, 2013 (Mar. 29, 2017).

U.S. Appl. No. 14/128,583, Dec. 7, 2016 Notice of Allowance.

U.S. Appl. No. 14/128,583, Jan. 5, 2017 Amendment After Allowance.

U.S. Appl. No. 14/128,583, Mar. 3, 3028 Issue Fee Payment.

U.S. Appl. No. 15/487,365, Jan. 19, 2018 Notice of Allowance.

U.S. Appl. No. 15/487,365, Jan. 25, 2018 Issue Fee Payment.

U.S. Appl. No. 15/916,258, Oct. 2, 2020 Non-Final Office Action.

U.S. Appl. No. 15/916,258, Jan. 4, 2021 Response to Non-Final Office Action.

U.S. Appl. No. 15/916,258, Apr. 15, 2021 Final Office Action.

U.S. Appl. No. 15/916,258, Jul. 16, 2021 Amendment and Request for Continued Examination (RCE).

U.S. Appl. No. 15/916,258, Sep. 10, 2021 Non-Final Office Action.

U.S. Appl. No. 15/916,258, Nov. 24, 2021 Examiner Interview Summary.

U.S. Appl. No. 15/916,258, Dec. 10, 2021 Response to Non Final Office Action.

U.S. Appl. No. 15/916,258, Apr. 5, 2022 Notice of Allowance.

U.S. Appl. No. 15/916,258, Jul. 5, 2022 Issue Fee Payment.

Armour, J. C., et al., "Application of Chronic Intravascular Blood Glucose Sensor in Dogs", *Diabetes*, vol. 39, 1990, pp. 1519-1526.

Arnold, M. A., et al., "Selectivity Assessment of Noninvasive Glucose Measurements Based on Analysis of Multivariate Calibration Vectors", *Journal of Diabetes Science and Technology*, vol. 1. No. 4, 2007, pp. 454-462.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4. No. 5, 2002, pp. 607-613.

Choleau, C., et al., "Calibration of a Subcutaneous Amperometric Glucose Sensor Implanted for 7 Days in Diabetic Patients Part 2. Superiority of the One-Point Calibration Method", *Biosensors and Bioelectronics*, vol. 17, No. 8, 2002, pp. 647-654.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Diabetes Control and Complications Trial Research Group, "The Effect of Intensive Treatment of Diabetes on the Development and Progression of Long-Term Complications in Insulin-Dependent Diabetes Mellitus," *New England J. Med.* vol 329, 1993, pp. 977-986.

(56) References Cited

OTHER PUBLICATIONS

Eren-Oruklu, M., et al., "Estimation of Future Glucose Concentrations with Subject-Specific Recursive Linear Models", *Diabetes Technology & Therapeutics* vol. 11(4), 2009, pp. 243-253.
Feldman, B., et al., "A Continuous Glucose Sensor Based on Wired Enzyme™ Technology—Results from a 3-Day Trial in Patients with Type 1 Diabetes", *Diabetes Technology & Therapeutics*. vol. 5. No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Georgescu, B., et al., "Real-Time Multimodel Tracking of Myocardium in Echocardiography Using Robust Information Fusion", *Medical Image Computing and Computer-Assisted Intervention*, 2004, pp. 777-785.
Goldman, J. M., et al., "Masimo Signal Extraction Pulse Oximetry", *Journal of Clinical Monitoring and Computing*, vol. 16, No. 7, 2000, pp. 475-483.
Guerci, B., et al., "Clinical Performance of CGMS in Type 1 Diabetic Patients Treated by Continuous Subcutaneous Insulin Infusion Using Insulin Analogs", *Diabetes Care*, vol. 26, 2003, pp. 582-589.
Isermann, R., "Supervision, Fault-Detection and Fault-Diagnosis Methods—An Introduction", *Control Engineering Practice*, vol. 5. No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, P. C., "Peripheral Circulation", John Wiley & Sons, 1978, pp. 198.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Kaplan, S. M., "Wiley Electrical and Electronics Engineering Dictionary", *IEEE Press*, 2004, pp. 141, 142, 548, 549.
Kovatchev, B. P., et al., "Evaluating the Accuracy of Continuous Glucose-Monitoring Sensors", *Diabetes Care*, vol. 27, No. 8, 2004, pp. 1922-1928.
Kuure-Kinsey, M., et al., "A Dual-Rate Kalman Filter for Continuous Glucose Monitoring", *Proceedings of the 28th IEEE, EMBS Annual International Conference, New York City*, 2006, pp. 63-66.
Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.
Lortz, J., et al., "What is Bluetooth? We Explain The Newest Short-Range Connectivity Technology", *Smart Computing Learning Series, Wireless Computing*, vol. 8, Issue 5, 2002, pp. 72-74.
Maher, "A Method for Extrapolation of Missing Digital Audio Data", *Preprints of Papers Presented at the AES Convention*, 1993, pp. 1-19.
Maher, "Audio Enhancement using Nonlinear Time-Frequency Filtering", *AES 26th International Conference*, 2005, pp. 1-9.
Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.
McGarraugh, G., et al., "Glucose Measurements Using Blood Extracted from the Forearm and the Finger", *TheraSense, Inc.*, 2001, 16 Pages.
McGarraugh, G., et al., "Physiological Influences on Off-Finger Glucose Testing", *Diabetes Technology & Therapeutics*. vol. 3. No. 3, 2001, pp. 367-376.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
Morbiducci, U, et al., "Improved Usability of the Minimal Model of Insulin Sensitivity Based on an Automated Approach and Genetic Algorithms for Parameter Estimation", *Clinical Science*, vol. 112, 2007, pp. 257-263.
Mougiakakou, et al., "A Real Time Simulation Model of Glucose-Insulin Metabolism for Type 1 Diabetes Patients", *Proceedings of the 2005 IEEE*, 2005, pp. 298-301.
Panteleon, A. E., et al., "The Role of the Independent Variable to Glucose Sensor Calibration", *Diabetes Technology & Therapeutics*, vol. 5, No. 3, 2003, pp. 401-410.
Parker, R., et al., "Robust H∞ Glucose Control in Diabetes Using a Physiological Model", *AIChE Journal*, vol. 46, No. 12. 2000, pp. 2537-2549.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*. vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*. Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.

(56) References Cited

OTHER PUBLICATIONS

Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Whipple, G., "Low Residual Noise Speech Enhancement Utilizing Time-Frequency", *Proceedings of the International Conference on Acoustics, Speech, and Signal Processing*, vol. 19, 1994, pp. 15-18.
Wilson, G. S., et al., "Progress Toward the Development of an Implantable Sensor for Glucose", *Clinical Chemistry*, vol. 38, No. 9, 1992, pp. 1613-1617.
Wolfe, P. J., et al., "Interpolation of Missing Data Values for Audio Signal Restoration Using a Gabor Regression Model", *2005 IEEE International Conference on Acoustics, Speech, and Signal Processing*. vol. 5, 2005, pp. 517-520.
PCT Application No. PCT/US2012/062541, International Preliminary Report on Patentability and Written Opinion of The International Searching Authority mailed May 15, 2014.
PCT Application No. PCT/US2012/062541, International Search Report and Written Opinion of the International Searching Authority mailed Dec. 31, 2012.
Alva et al., "Accuracy of a 14-Day Factory-Calibrated Continuous Glucose Monitoring System with Advanced Algorithm in Pediatric and Adult Population with Diabetes," Journal of Diabetes Science and Technology, vol. 16(1) 70-77 (2022).
Campbell et al., "Outcomes of using flash glucose monitoring technology by children and young people with type 1 diabetes in a single arm study," Pediatric Diabetes, 1294-1301 (2018).
Deshmuk et al., "Effect of Flash Glucose Monitoring on Glycemic Control, Hypoglycemia, Diabetes-Related Distress, and Resource Utilization in the Association of British Clinical Diabetologists (ABCD) Nationwide Audit," https://doi.org/10.2337/dc20-0738, Diabetes Care, 8 pages (2020).
Deutscher Gesundheitsbericht, Diabetes 2021, Die Bestandsaufnahme , German Diabetes Society, with English Abstract, 15 pages (2021).
DexCom™ STS™ Continuous Glucose Monitoring System, User's Guide, 2006, 57 pages.
FDA, STS-7 Continuous Glucose Monitoring System, P050012/S001, May 31, 2007, 95 pages.
Haak et al., "Use of Flash Glucose-Sensing Technology for 12 months as a Replacement for Blood Glucose Monitoring in Insulin-treated Type 2 Diabetes," Diabetes Ther., 14 pages (2017).
Roussel et al., "Important Drop in Rate of Acute Diabetes Complications in People With Type 1 or Type 2 Diabetes After Initiation of Flash Glucose Monitoring in France: The Relief Study," American Diabetes Association, Diabetes Care, 1368-1376 (2021).
Exhibit CP-2, Expert Report of Dr. Cesar C. Palerm, Sep. 20, 2022: Sparacino, et al., Glucose Concentration can be Predicted Ahead in Time From Continuous Glucose Monitoring Sensor Time-Series, IEEE Transactions on Biomedical Engineering, vol. 54, No. 5, pp. 931-937 (2007).
Exhibit CP-3, Expert Report of Dr. Cesar C. Palerm, Sep. 20, 2022: In Vivo Glucose Sensing, Chemical Analysis, A Series of Monographs on Analytical Chemistry and Its Applications, vol. 174, Wiley (2010).
Exhibit CP-4, Expert Report of Dr. Cesar C. Palerm, Sep. 20, 2022: Animas® Vibe™, the First Integrated Offering from Animas Corporation and Dexcom, Inc., Receives European CE Mark Approval (2011).
Exhibit CP-6, Second Expert Report of Dr. Cesar C. Palerm, Oct. 21, 2022: Bailey, et al., Reduction in Hemoglobin A 1 c with Real-Time Continuous Glucose Monitoring: Results from a 12-Week Observational Study, Diabetes Technology & Therapeutics, vol. 9, No. 3, pp. 203-210 (2007).
Exhibit CP-7, Second Expert Report of Dr. Cesar C. Palerm, Oct. 21, 2022: Garg, et al., Improvement in Glycemic Excusions With a Transcutaneous, Real-Time Continuous Glucose Sensor, Diabetes Care, vol. 29, No. 1, pp. 44-50 (2006).
Exhibit CP-8, Second Expert Report of Dr. Cesar C. Palerm, Oct. 21, 2022: Garg, et al., Relatioship of Fasting and Hourly Blood Glucose Levels to HbAlc Values, Diabetes Care, vol. 29, No. 12, pp. 2644-2649 (2006).
Exhibit CP-9, Second Expert Report of Dr. Cesar C. Palerm, Oct. 21, 2022: Welcome to Your FreeStyle Libre System, In-Service Guide, Abbott (2017).
Exhibit CP-10, Second Expert Report of Dr. Cesar C. Palerm, Oct. 21, 2022: Standards of Medical Care in Diabetes-2009, American Diabetes Association, Diabetes Care, vol. 32, Supplement 1, pp. S13-S61 (2009).
Exhibit No. 2, to the Expert Report of Professor Nick Oliver, Sep. 20, 2022: Committee for Proprietary Medicinal Products (CPMP), Note for Guidance on Clinical Investigation of Medicinal Products in the Treatment of Diabetes Mellitus, EMEA, The European Agency for the Evaluation of Medicinal Products (2002).
Exhibit No. 3, to the Expert Report of Professor Nick Oliver, Sep. 20, 2022: Defining and Reporting Hypoglycemia in Diabetes, Diabetes Care, vol. 28, No. 5, pp. 1245-1249 (2005).
Exhibit No. 4, to the Expert Report of Professor Nick Oliver, Sep. 20, 2022: Amiel, et al., Review Article, Hypoglycaemia in Type 2 diabetes, Diabetic Medicine, vol. 25, pp. 245-254 (2008).
Exhibit No. 5, to the Expert Report of Professor Nick Oliver, Sep. 20, 2022: Swinnen, et al., Changing the glucose cut-off values that define hypoglycaemia has a major effect on reported frequencies of hypoglycaemia, Diabetologia, vol. 52, pp. 38-41 (2009).
Exhibit No. 6, to the Expert Report of Professor Nick Oliver, Sep. 20, 2022: Frier, Defining hypoglycaemia: what level has clinical relevance?, Diabetologia, vol. 52, pp. 31-34 (2009).
Exhibit No. 7, to the Expert Report of Professor Nick Oliver, Sep. 20, 2022: Cryer, Preventing hypoglycaemia: what is the appropriate glucose alert value?, Diabetologia, vol. 52, pp. 35-37 (2009).
Exhibit No. 8, to the Expert Report of Professor Nick Oliver, Sep. 20, 2022: Oxford Textbook of Endocrinology and Diabetes (2011).
Exhibit No. 9, to the Expert Report of Professor Nick Oliver, Sep. 20, 2022: Guideline on clinical investigation of medicinal products in the treatment or prevention of diabetes mellitus, European Medicines Agency, Science Medicines Health (2012).
Exhibit No. 10, to the Expert Report of Professor Nick Oliver, Sep. 20, 2022: Type 1 Diabetes Research Roadmap, Identifying the strengths and weaknesses, gaps and opportunities of UK type 1 diabetes research; clearing a path to the cure, JDRF Improving Lives. Curing Type 1 Diabetes. Join US in finding the cure for type 1 diabetes (2013).
Exhibit No. 11, to the Expert Report of Professor Nick Oliver, Sep. 20, 2022: The Effect of Intensive Treatment of Diabetes on the Development and Progression of Long-Term Complications in Insulin-Dependent Diabetes Mellitus, The New England Journal of Medicine, vol. 329, No. 14 (1993).
Exhibit No. 12, to the Expert Report of Professor Nick Oliver, Sep. 20, 2022: Modern Standards and Service Models, Diabetes, National Service Framework for Diabetes: Standards, Department of Health (2000).
Exhibit No. 13, to the Expert Report of Professor Nick Oliver, Sep. 20, 2022: Training in flexible, intensive, insulin management to enable dietary freedom in people with type 1 diabetes: dose adjustment for normal eating (DAFNE) randomised controlled trial, BMJ, vol. 325 (2002).
Exhibit No. 14, to the Expert Report of Professor Nick Oliver, Sep. 20, 2022: Type 1 diabetes: diagnosis and management of type 1 diabetes in children, young people and adults, Clinical Guideline 15, NHS, National Institute for Clinical Excellence (2004).
Exhibit No. 15, to the Expert Report of Professor Nick Oliver, Sep. 20, 2022: Oxford Textbook of Endocrinology and Diabetes (2011).
Exhibit No. 16, to the Expert Report of Professor Nick Oliver, Sep. 20, 2022: Pickup, et al., Glycaemic control in type 1 diabetes during

(56) References Cited

OTHER PUBLICATIONS real time continuous glucose monitoring compared with self monitoring of blood glucose: meta-analysis of randomised controlled trials using individual patient data, BMJ (2011).
Exhibit No. 17, to the Expert Report of Professor Nick Oliver, Sep. 20, 2022: Diabetes (type 1), NIHR (2011).
Exhibit No. 18, to the Expert Report of Professor Nick Oliver, Sep. 20, 2022: Aleppo, et al., Replace-BG: A Randomized Trial Comparing Continuous Glucose Monitoring With and Without Routine Blood Glucose Monitoring in Adults With Well-Controlled Type 1 Diabetes, Diabetes Care, vol. 40, pp. 538-545 (2017).
Exhibit No. 19, to the Expert Report of Professor Nick Oliver, Sep. 20, 2022: Glucose Concentrations of Less Than 3.0 mmol/L (54 mg/dL) Should Be Reported in Clinical Trials: A Joint Position Statement of the American Diabetes Association and the European Association for the Study of Diabetes, Diabetes Care, vol. 40, pp. 155-157 (2017).
Exhibit No. 20, to the Expert Report of Professor Nick Oliver, Sep. 20, 2022: Continuous Glucose Sensors: Continuing Questions about Clinical Accuracy, J Diabetes Sci Technol vol. 1, Issue 5, pp. 669-675 (2007).
Exhibit No. 21, to the Expert Report of Professor Nick Oliver, Sep. 20, 2022: DeVries, Glucose Sensing Issues for the Artificial Pancreas, Journal of Diabetes Science and Technology, vol. 2, Issue 4, pp. 732-734 (2008).
Exhibit No. 22, to the Expert Report of Professor Nick Oliver, Sep. 20, 2022: Innovation Milestones, et al.
Exhibit No. 23, to the Expert Report of Professor Nick Oliver, Sep. 20, 2022: CGMS® System Gold™ Continuous Glucose Monitoring Overview, Medtronic MiniMed (2004).
Exhibit No. 24, to the Expert Report of Professor Nick Oliver, Sep. 20, 2022: GlucoWatch G2, Automatic Glucose Biographer and Auto Sensors (2002).
Exhibit No. 25, to the Expert Report of Professor Nick Oliver, Sep. 20, 2022: Guardian® REAL-Time, Continuous Glucose Monitoring System, User Guide, Medtronic MiniMed (2006).
Exhibit No. 26, to the Expert Report of Professor Nick Oliver, Sep. 20, 2022: CGMS® iPro™ Continuous Glucose Recorder, User Guide, Medtronic MiniMed (2007).
Exhibit No. 27, to the Expert Report of Professor Nick Oliver, Sep. 20, 2022: FreeStyle Navigator, Continuous Glucose Monitoring System, User Guide, Abbott (2008, 2010).
Exhibit No. 28, to the Expert Report of Professor Nick Oliver, Sep. 20, 2022: FreeStyle Navigator II, Continuous Glucose Monitoring System, User's Manual, Abbott (2011-2013).
Exhibit No. 29, to the Expert Report of Professor Nick Oliver, Sep. 20, 2022: Dexcom G4, Continuous Glucose Monitoring System, User's Guide (2013).
Exhibit No. 30, to the Expert Report of Professor Nick Oliver, Sep. 20, 2022: Revised Specification for US 2007/208244A1.
Exhibit No. 31, to the Expert Report of Professor Nick Oliver, Sep. 20, 2022: Revised Specification for EP625.
Exhibit No. 32, to the Expert Report of Professor Nick Oliver, Sep. 20, 2022: Puhr, et al., Real-World Hypoglycemia Avoidance with a Predictive Low Glucose Alert Does Not Depend on Frequent Screen Views, Journal of Diabetes Science and Technology, vol. 14(1), pp. 83-86 (2020).
Exhibit No. 33, to the Expert Report of Professor Nick Oliver, Sep. 20, 2022: Rilstone, et al., The impact of CGM with a predictive hypoglycaemia alert function on hypoglycaemia in physical activity for people with type 1 diabetes: PACE study (2022).
Exhibit No. 34, to the Expert Report of Professor Nick Oliver, Sep. 20, 2022: FreeStyle Libre 2, Flash Glucose Monitoring System, User's Manual, Abbott (2019-2021).
Exhibit No. 35, to the Expert Report of Professor Nick Oliver, Sep. 20, 2022: FreeStyle Libre 3, Continuous Glucose Monitoring System, User's Manual, Abbott (2022).
Exhibit No. 37, to the Second Expert Report of Professor Nick Oliver, Oct. 21, 2022: Oliver, et al., Review Article, Glucose sensors, a review of current and emerging technology, Diabetic Medicine, vol. 26, pp. 197-210 (2009).
U.S. Appl. No. 61/227,967, filed Jul. 23, 2009, Hoss, et al.
Abel, et al., "Biosensors for in vivo glucose measurement: can we cross the experimental stage", Biosensors and Bioelectronics, 17:1059-1070 (2002).
About Dexcom—Continuous Glucose Monitoring Company, 12 pages (2021).
About the Congressional Record, Congress.gov, Library of Congress, 3 pages (2011).
Alcock, et al., "Continuous Analyte Monitoring to Aid Clinical Practice", IEEE Engineering in Medicine and Biology, pp. 319-325 (1994).
Bard, et al., Electrochemical Methods, Fundamentals and Applications, pp. 174-175 (1980).
Bequette, "Continuous Glucose Monitoring: Real Time Algorithms for Calibration, Filtering, and Alarms", Journal of Diabetes Science and Technology, 4(2):404-418 (2010).
Bindra et al., "Design and in Vitro Studies of a Needle-Type Glucose Sensor for Subcutaneous Monitoring," Analytical Chemistry, vol. 63, No. 17, 1692-1696 (1991).
Burton, "Urging FDA to Act Promptly to Approve Artificial Pancreas Technologies," Congressional Record (Bound Edition), vol. 157, Part 13, 3 pages (2011).
Cass et al., "Ferrocene-Mediated Enzyme Electrode for Amperometric Determination of Glucose," Analytical Chemistry, vol. 56, No. 4, 5 pages (1984).
Cengiz, et al., "A Tale of Two Compartments: Interstitial Versus Blood Glucose Monitoring", Diabetes Technology & Therapeutics, 11(1):S-11-S16 (2009).
Chen, et al., "Defining the Period of Recovery of the Glucose Concentration after Its Local Perturbation by the Implantation of a Miniature Sensor", Clin Chem Lab Med, 40(8):786-789 (2002).
Chen, et al., "Glucose microbiosensor based on alumina sol gel matrix/eletropolymerized composite membrane", Biosensors and Bioelectronics, 17:1005-1013 (2002).
Chen, et al., "In Situ Assembled Mass-Transport Controlling Micromembranes and Their Application in Implanted Amperometric Glucose Sensors", Analytical Chemistry, 72(16):3757-3763 (2000).
Chen, et al., "In vivo Glucose Monitoring with Miniature "Wired" Glucose Oxidase Electrodes", Analytical Sciences, 17:1297-1300 (2001).
Choleau, et al., "Calibration of a subcutaneous amperometric glucose sensor Part 1. Effect of measurement uncertainties on the determination of sensor sensitivity and background current", Biosensors and Bioelectronics, 17:641-646 (2002).
Choudhary et al., "Insulin Pump Therapy with Automated Insulin Suspension in Response to Hypoglycemia, Reduction in nocturnal hypoglycemia in those at greatest risk," Diabetes Care, vol. 34, 2023-2025 (2011).
Chung, "In vitro Evaluation of the Continuous Monitoring Glucose Sensors with Perfluorinated Tetrafluoroethylene Coatings", Bull. Korean Chem. Soc., 24(4):514-516 (2003).
Claims, Specification and Drawings for System and Methods for Providing Sensitive and Specific Alarms, 103 pages.
Clarke et al., "Statistical Tools to Analyze Continuous Glucose Monitor Data," Diabetes Technology & Therapeutics, vol. 11, Supplement 1, S-45-S-54 (2009).
Csöregi, et al., "Design, Characterization, and One-Point in Vivo Calibration of a Subcutaneously Implanted Glucose Electrode", Anal. Chem., 66(19):3131-3138 (1994).
Cunningham et al., "In Vivo Glucose Sensing, Chemical Analysis: A Series of Monographs on Analytical Chemistry and Its Applications," vol. 174, Wiley, 466 pages (2010).
De Block, et al., "Minimally-Invasive and Non-Invasive Continuous Glucose Monitoring Systems: Indications, Advantages, Limitations and Clinical Aspects", Current Diabetes Reviews, 4:159-168 (2008).
Declaration of Duncan Hall (2021) including DexCom™ STS™ Continuous Glucose Monitoring System User's Guide (2006), 64 pages.

(56) References Cited

OTHER PUBLICATIONS

Decuir, "Bluetooth 4.0:Low Energy", Standards Architect, CSR Technology, Councilor, Bluetooth Architecture Review Board, IEEE Region 6 Northwest Area Chair, 104 pages (2012).
Dementyev, et al., "Power Consumption Analysis of Bluetooth Low Energy, ZigBee and ANT Sensor Nodes in a Cyclic Sleep Scenario", IEEE International Wireless Symposium (IWS), 5 pages (2013).
Facchinetti et al., "A New Index to Optimally Design and Compare Continuous Glucose Monitoring Glucose Prediction Algorithms," Diabetes Technology & Therapeutics, vol. 13, No. 2, 111-119 (2011).
Facchinetti, et al., "Enhanced Accuracy of Continuous Glucose Monitoring by Online Extended Kalman Filtering", Diabetes Technology & Therapeutics, 12(5):353-363 (2010).
FDA PMA Approvals, 3 pages.
FDA Premarket Approval (PMA) for Freestyle Navigator Continuous Glucose Monitor, 6 pages, Notice Date: Apr. 1, 2008.
Feature Analysis, 1 page.
Federal Register, vol. 76, No. 120, pp. 36542-36543 (2011).
Feldman, et al., "A Continuous Glucose Sensor Based on Wired Enzyme™ Technology—Results from a 3-Day Trial in Patients with Type 1 Diabetes", Diabetes Technology & Therapeutics, 5(5):769-779 (2003).
Fischer, "Fundamentals of Glucose Sensors", Diabetic Medicine, 8:309-321 (1991).
Fraser, "An Introduction to in vivo Biosensing: Progress and Problems", Biosensors in the Body: Continuous in vivo Monitoring, pp. 1-56 (1997).
FreeStyle Navigator Continuous Glucose Monitoring System, Summary of Safety and Effectiveness Data in support of Pre-Market Approval (PMA) No. P050020, Abbott Diabetes Care, 27 pages (2008).
FreeStyle Navigator Continuous Glucose Monitoring System, User Guide, Abbott Diabetes Care Inc., 195 pages (2008).
Frost, et al., "Implantable chemical sensors for real-time clinical monitoring: progress and challenges", Current Opinion in Chemical Biology, 6:633-641 (2002).
Garg et al., "Improved Glucose Excursions Using an Implantable Real-Time Continuous Glucose Sensor in Adults with Type 1 Diabetes," Diabetes Care, vol. 27, No. 3, 734-738 (2004).
Gerritsen, et al., "Subcutaneously implantable glucose sensors in patients with diabetes mellitus; still many problems", Dutch Journal of Medicine, 146(28):1313-1316 (2002) (with English Machine Translation).
Guardian® REAL-Time, Continuous Glucose Monitoring System, User Guide, Medtronic MiniMed, Inc., 181 pages (2006).
Guardian® RT, Continuous Glucose Monitoring System, REF MMT-7900, User Guide, Medtronic MiniMed, 128 pages (2005).
Guerra et al., "A Dynamic Risk Measure from Continuous Glucose Monitoring Data," Diabetes Technology & Therapeutics, vol. 13, No. 8, 843-852 (2011).
Hayter, P. G. et al., Performance Standards for Continuous Glucose Monitors, Diabetes Technology & Therapeutics, vol. 7, No. 5, pp. 721-726 (2005).
Heinemann, "Continuous Glucose Monitoring by Means of the Microdialysis Technique: Underlying Fundamental Aspects", Diabetes Technology & Therapeutics, 5(4):545-561 (2003).
Heise, et al., "Hypoglycemia Warning Signal and Glucose Sensors: Requirements and Concepts", Diabetes Technology & Therapeutics, 5(4):563-571 (2003).
Heller, "Implanted Electrochemical Glucose Sensors for the Management of Diabetes", Annu. Rev. Biomed. Eng., 01:153-175 (1999).
Heller, et al., "Electrochemical Glucose Sensors and Their Applications in Diabetes Management", Chemical Reviews, 108(7):2482-2505 (2008).
Instructions for Use DexCom™ STS™ Sensor, 1 page.
International Standard, IEC 60601-1-8, Medical Electrical Equipment, 166 pages (2006).
Jiménez, et al., "Glucose sensor based on an amperometric microelectrode with a photopolymerizable enzyme membrane", Sensors and Actuators B, 26-27:421-424 (1995).
Johnson, et al., "Reduction of Electrooxidizable Interferent Effects: Optimization of the Applied Potential for Amperometric Glucose Sensors", Electroanalysis, 6:321-326 (1994).
Klonoff, "A Review of Continuous Glucose Monitoring Technology", Diabetes Technology & Therapeutics, 7(5):770-775 (2005).
Klonoff, "Continuous Glucose Monitoring: Roadmap for 21st century diabetes therapy", Diabetes Care, 28(5):1231-1239 (2005).
Knobbe, et al., "The Extended Kalman Filter for Continuous Glucose Monitoring", Diabetes Technology & Therapeutics, 7(1):15-27 (2005).
Koudelka, et al., "In-vivo Behaviour of Hypodermically Implanted Microfabricated Glucose Sensors", Biosensors & Bioelectronics, 6:31-36 (1991).
Koudelka-Hep, "Electrochemical Sensors for in vivo Glucose Sensing", Biosensors in the Body: Continuous in vivo Monitoring, pp. 57-77 (1997).
Kuure-Kinsey, et al., "A Dual-Rate Kalman Filter for Continuous Glucose Monitoring", Proceedings of the 28th IEEE, Embs Annual International Conference, pp. 63-66 (2006).
Kvist, et al., "Recent Advances in Continuous Glucose Monitoring: Biocompatibility of Glucose Sensors for Implantation in Subcutis", Journal of Diabetes Science and Technology, 1(5):746-752 (2007).
Letter from Department of Health & Human Services re: FreeStyle Navigator Continuous Glucose Monitoring System, 7 pages (2008).
Letter to EPO re. Divisional Application of EP Application No. 13784079.9 in the name of Dexcom, Inc., 2 pages (2020).
Lodwig, et al., "Continuous Glucose Monitoring with Glucose Sensors: Calibration and Assessment Criteria", Diabetes Technology & Therapeutics, 5(4):573-587 (2003).
McMurry Jr., The Artificial Pancreas Today, Henry Ford Hospital Medical Journal, vol. 31, No. 2, Article 4, 8 pages (1983).
Ming Li, et al., "Implantable Electrochemical Sensors for Biomedical and Clinical Applications: Progress, Problems, and Future Possibilities", Current Medicinal Chemistry, 14:937-951 (2007).
Moatti-Sirat, et al., "Evaluating in vitro and in vivo the interference of ascorbate and acetaminophen on glucose detection by a needle-type glucose sensor", Biosensors and Bioelectronics, 7(5):345-352 (1992).
Morak, et al., "Design and Evaluation of a Telemonitoring Concept Based on NFC-Enabled Mobile Phones and Sensor Devices", IEEE Transactions on Information Technology in Biomedicine, 16(1):17-23 (2012).
Movassaghi, et al., "Wireless Technologies for Body Area Networks: Characteristics and Challenges", IEEE, International Symposium on Communications and Information Technologies (ISCIT), pp. 42-47 (2012).
Nishida, et al., "Development of a ferrocene-mediated needle-type glucose sensor covered with newly designed biocompatible membrane, 2-methacryloyloxyethyl phosphorylcholine-co-n-butyl methacrylate", Medical Progress through Technology, 21:91-103 (1995).
Onuki, et al., "A Review of the Biocompatibility of Implantable Devices: Current Challenges to Overcome Foreign Body Response", Journal of Diabetes Science and Technology, 2(6):1003-1015 (2008).
Palerm et al., "Hypoglycemia Detection and Prediction Using Continuous Glucose Monitoring—A Study on Hypoglycemic Clamp Data," Journal of Diabetes Science and Technology. vol. 1, Issue 5, 624-629 (2007).
Palerm, et al., "Hypoglycemia Prediction and Detection Using Optimal Estimation", Diabetes Technology & Therapeutics, 7(1):3-14 (2005).
Poitout, et al., "Calibration in dogs of a subcutaneous miniaturized glucose sensor using a glucose meter for blood glucose determination", Biosensors & Bioelectronics, 7:587-592 (1992).
Rebrin, et al., "Subcutaneous glucose predicts plasma glucose independent of insulin: implications for continuous monitoring", American Journal of Physiology-Endocrinology and Metabolism, 277(3):E561-E571 (1999).
Renard, "Implantable glucose sensors for diabetes monitoring", Min Invas Ther & Allied Technol, 13(2):78-86 (2004).

(56) References Cited

OTHER PUBLICATIONS

Rhodes, et al., "Prediction of Pocket-Portable and Implantable Glucose Enzyme Electrode Performance from Combined Species Permeability and Digital Simulation Analysis", Analytical Chemistry, 66(9):1520-1529 (1994).
Robert, "Continuous Monitoring of Blood Glucose", Horm Res 57(suppl 1):81-84 (2002).
Sandham et al., "Blood Glucose Prediction for Diabetes Therapy Using Recurrent Artificial Neural Network," 9th European Signal Processing Conference (EUSIPCO 1998), IEEE (1998).
Schlosser, et al., "Biocompatibility of Active Implantable Devices", Biosensors in the Body: Continuous in vivo Monitoring, pp. 139-170 (1997).
Schmidt, et al., "Calibration of a wearable glucose sensor", The International Journal of Artificial Organs, 15(1):55-61 (1992).
Schmidtke, et al., "Accuracy of the One-Point in Vivo Calibration of "Wired" Glucose Oxidase Electrodes Implanted in Jugular Veins of Rats in Periods of Rapid Rise and Decline of the Glucose Concentration", Anal. Chem., 70:2149-2155 (1998).
Sparacino et al., "Glucose Concentration can be Predicted Ahead in Time From Continuous Glucose Monitoring Sensor Time-Series," IEEE Transaction on Biomedical Engineering, vol. 54, No. 5, 931-937 (2007).
Specification of the Bluetooth System, Experience More, Specification vol. 0, Covered Core Package Version: 4.0, 2 302 pages (2010).
STS® Seven Continuous Glucose Monitoring System, User's Guide, 74 pages (2007).
Summary of Safety and Effectiveness Data for Continuous Glucose Monitor, 27 pages (2008).
Summary of Safety and Effectiveness Data for DexCom™ STS™ Continuous Glucose Monitoring System, 20 pages (2006).
Summary of Safety and Effectiveness Data for STS®-7 Continuous Glucose Monitoring System, 14 pages (2007).
Tierney, et al., "Effect of Acetaminophen on the Accuracy of Glucose Measurements Obtained with the GlucoWatch Biographer", Diabetes Technology & Therapeutics, 2(2):199-207 (2000).
Townsend, et al., "Getting Started with Bluetooth Low Energy [Book]", O'Reilly, retrieved from https://www.oreilly.com/library/view/getting-started-with/9781491900550/ch01.html on (May 5, 2020), 26 pages.
Velho, et al., "Strategies for Calibrating a Subcutaneous Glucose Sensor", Biomed. Biochim. Acta, vol. 48, pp. 957-964 (1989).
Voskerician, et al., "Sensor Biocompatibility and Biofouling in Real-Time Monitoring", Wiley Encyclopedia of Biomedical Engineering, (John Wiley & Sons, Inc.), pp. 1-19 (2006).
Ward, "A Review of the Foreign-body Response to Subcutaneously-implanted Devices: The Role of Macrophages and Cytokines in Biofouling and Fibrosis", Journal of Diabetes Science and Technology, 2(5):768-777 (2008).
Ward, et al., "A new amperometric glucose microsensor: in vitro and short-term in vivo evaluation", Biosensors & Bioelectronics, 17:181-189 (2002).
Wikipedia; "Blood glucose monitoring" retrieved from "https://web.archive.org/web/20111215063153/http://en.wikipedia.org/wiki/Blood_glucos e_monitoring" on Aug. 1, 2021, 6 pages.
Wikipedia , "Near field communication" retrieved from "http://en.wikipedia.org/w/index.php?title=Near_field_communication&oldid=543740757" on Jun. 27, 2014, 14 pages.
Yang, et al., "Glucose Biosensors Based on Oxygen Electrode with Sandwich-Type Membranes", Annals of Biomedical Engineering, 23:833-839 (1995).
Yang, et al., "Glucose Biosensors with Enzyme Entrapped in Polymer Coating", Biomedical Instrumentation & Technology, 29(2): 125-133 (1995).
Abbott Press Release—"Abbott Receives CE Mark for FreeStyle® Libre, A Revolutionary Glucose Monitoring System for People with Diabetes" retrieved from https://abbott.mediaroom.com/2014-09-03-Abbott-Receives-CE-Mark-for-FreeStyle-Libre-a-Revolutionary-Glucose-Monitoring-System-for-People-with-Diabetes/, Sep. 3, 2014, 3 pages.
Abbott Press Release—"Abbott Receives FDA Approval for the FreeStyle Libre Pro™ System, A Revolutionary Diabetes Sensing Technology for Healthcare Professionals to Use with their Patients" retrieved from https://abbott.mediaroom.com/2016-09-28-Abbott-Receives-FDA-Approval-for-the-FreeStyle-Libre-Pro-System-a-Revolutionary-Diabetes-Sensing-Technology-for-Healthcare-Professionals-to-use-with-their-Patients/, Sep. 28, 2016, 5 pages.
Abbott Press Release—"Abbott's FreeStyle® Libre 14 Day Flash Glucose Monitoring System Now Approved in U.S." retrieved from https://abbott.mediaroom.com/2018-07-27-Abbotts-FreeStyle-R-Libre-14-Day-Flash-Glucose-Monitoring-System-Now-Approved-in-U-S/, Jul. 27, 2018, 3 pages.
About the Congressional Record, Congress. Gov, 3 pages, Feb. 22, 2022.
Alcock, et al., "Continuous Analyte Monitoring to Aid Clinical Practice", IEEE Engineering in Medicine and Biology, vol. 13, No. 3, pp. 319-325 (1994).
Anzhsn, National Horizon Scanning Unit Horizon Scanning Report, "GlucoWatch® G2 Biographer for the non-invasive monitoring of glucose levels", 46 pages, May 2004.
Approved Judgment, In the High Court of Justice Business and Property Courts of England and Wales Intellectual Property List (ChD) Patents Court, Case No. HP-2021-000025 & HP-2021-000026, 137 pages, Jan. 15, 2024.
Breen, The iPhone Pocket Guide, Sixth Edition, Peachpit Press, 96 pages (2012).
Brown et al., "test drive—Dexcom's G4 Platinum CGM," diaTribe Learn Making Sense of Diabetes, 4 pages (2012).
Buckingham et al., "Prevention of Nocturnal Hypoglycemia Using Predictive Alarm Algorithms and Insulin Pump Suspension," Diabetes Care, vol. 33, No. 5, 1013-1017 (2010).
Cather, CGM Frustrations Survey dated Jun. 2020, 37 pages in *Abbott Diabetes Care Inc., et al.* v. *Dexcom, Inc.*, Case No. 1:21-cv-00977-KAJ (District of Delaware).
Clinical Trials, Competitor and Ecosystem Players dated Jun. 25, 2020, 29 pages in *Abbott Diabetes Care Inc., et al.* v. *Dexcom, Inc.*, Case No. 1:21-cv-00977-KAJ (District of Delaware).
Close "Test Driving Dexcom's Short-Term Sensor (STS): A Look at Continuous Glucose Monitoring," diaTribe Learn Making Sense of Diabetes, 2 pages (2006).
Dassau et al., Real-Time Hypoglycemia Prediction Suite Using Continuous Glucose Monitoring, A safety net for the artificial pancreas, Diabetes Care, vol. 33, No. 3, 1249-1254 (2010).
Declaration of Dr. Anthony Edward Cass in Support of Petition for Inter Partes Review of U.S. Pat. No. 11,020,031 in *Abbott Diabetes Care Inc.* v. *Dexcom, Inc.*, Case No. IPR2024-00890, In the United States Patent and Trademark Office, Before the Patent Trial and Appeal Board, May 10, 2024, 138 pages.
Declaration of Karl R. Leinsing, MSME, PE, in Support of Abbott's Motion for Summary Judgment dated May 19, 2023, 81 pages in *Abbott Diabetes Care Inc., et al.* v. *Dexcom, Inc.*, Case No. 1:21-cv-00977-KAJ (District of Delaware).
Declaration of Dr. Sayfe Kiael, Ph.D., Inter Partes Review of U.S. Pat. No. 10,375,222, 100 pages (2024).
Declaration of David Rodbard, M.D., Petition for Inter Partes Review of U.S. Pat. No. 9,119,528, IPR2024-00840, 109 pages, May 1, 2024.
Declaration of Lane Desborough, Petition for Inter Partes Review of U.S. Pat. No. 11,213,204, IPR2024-00853, 150 pages, May 3, 2024.
Declaration of Sylvia D. Hall-Ellis, Ph.D., IPR2024-00840 of U.S. Pat. No. 9,119,528, Parts 1-2 (400 pages) Apr. 24, 2024.
Department of Health & Human Services, FDA, P050012/S001, STS-7 Continuous Glucose Monitoring System, 7 pages, May 31, 2007.
DeSalvo et al., "Remote Glucose Monitoring in Camp Setting Reduces the Risk of Prolonged Nocturnal Hypoglycemia," Diabetes Technology & Therapeutics, vol. 16, No. 1, 10 pages, DOI: 10.1089/dia.2013.0139 (2014).

(56) References Cited

OTHER PUBLICATIONS

Dock, et al., "Multivariate data analysis of dynamic amperometric biosensor responses from binary analyte mixtures—application of sensitivity correction algorithms", Talanta, 65:298-305 (2005).
Effectiveness and Safety Study of the DexCom™ G4 Continuous Glucose Monitoring System, DexCom, Inc., U.S. National Library of Medicine, ClinicalTrials.gov Identifier: NCT01111370, 4 pages (2017).
E-mail Communication from Christopher M. Dougherty regarding Bi Monthly Global Commercial Insights Meeting dated Dec. 17, 2019, 69 pages in *Abbott Diabetes Care Inc., et al.* v. *Dexcom, Inc.*, Case No. 1:21-cv-00977-KAJ (District of Delaware).
FDA [Docket No. FDA-2011-D-0464], Draft Guidance for Industry and Food and Drug Administration Staff: The Content of Investigational Device Exemption and Premarket Approval Applications for Low Glucose Suspend Device Systems; Availability, Federal Register / vol. 76, No. 120 / Wednesday, Jun. 22, 2011 /Notices, 2 pages.
FDA PMA Final Decisions Rendered for May 2007—The Wayback Machine—https://web.archive.org/web/20070630150626/http:/www.fda.gov/cdrh/pma/pmamay07.html, 1 page, May 31, 2007.
FDA PMA Final Decisions Rendered for May 2007—The Wayback Machine—https://web.archive.org/web/20070630150626/http:/www.fda.gov/cdrh/pma/pmamay07.html, 21 pages, Jun. 13, 2007.
FDA STS-7, Glucose Monitoring System—P050012/S001, The Wayback Machine—https://web.archive.org/web/20070705190828/http:/www.fda.gov:80/cdrh/pdf5/p050012s001.html, 21 pages, 2007.
FDA FreeStyle Navigator Continuous Glucose Monitoring System, P050020, 7 pages, Mar. 12, 2008.
File History of U.S. Pat. No. 9,119,528 issued Sep. 1, 2015, Parts 1-8 (1,438 pages).
File History of U.S. Pat. No. 9,801,541 issued Oct. 31, 2017, 834 pages.
File History of U.S. Pat. No. 11,213,204 issued Jan. 1, 2022, 848 pages.
Design U.S. Appl. No. 29/101,218, filed Feb. 25, 1999, 11 pages.
U.S. Pat. No. 11,020,031 issued Jun. 1, 2021, 1058 pages.
FreeStyle Libre 2 HCP Pulse, Mar. 2021 Report, dated Mar. 1, 2021, 14 pages in *Abbott Diabetes Care Inc., et al.* v. *Dexcom, Inc.*, Case No. 1:21-cv-00977-KAJ (District of Delaware).
Godek, et al., Chapter 2, "The Macrophage in Wound Healing Surrounding Implanted Devices", In Vivo Glucose Sensing, 36 pages (2010).
Gross, et al., "Performance Evaluation of the MiniMed® Continuous Glucose Monitoring System During Patient Home Use", Diabetes Technology & Therapeutics, vol. 2, No. 1, pp. 49-56 (2000).
Heller, "Integrated Medical Feedback Systems for Drug Delivery", American Institute of Chemical Engineers Journal, vol. 51, No. 4, pp. 1054-1066 (2005).
Heller, et al., "Electrochemical Glucose Sensors and Their Applications in Diabetes Management", Chem. Rev., 108, Parts 1-3, pp. 2482-2505 (2008).
Henning, Chapter 5, "Commercially Available Continuous Glucose Monitoring Systems", In Vivo Glucose Sensing, 50 pages (2010).
Javanmardi et al., "G4 Platinum Continuous Glucose Monitor," US Pharm. 38(9), 64-68 (2013).
Keith-Hynes et al., "The Diabetes Assistant: A Smartphone-Based System for Real-Time Control of Blood Glucose," Electronics, 3, 609-623; doi:10.3390/electronics3040609 (2014).
Klonoff et al., "Innovations in Technology for the Treatment of Diabetes: Clinical Development of the Artificial Pancreas (an Autonomous System)," Journal of Diabetes Science and Technology, vol. 5, Issue 3, 804-826, May 2011.
Koudelka-Hep, "Electrochemical Sensors for in vivo Glucose Sensing", Biosensors in the Body: Continuous In Vivo Monitoring, 12 pages (1997).
Kovatchev et al., "Symmetrization of the Blood Glucose Measurement Scale and Its Applications," Diabetes Care, vol. 20, No. 11, 1655-1658 (1997).
Kowalski, "Can We Really Close the Loop and How Soon? Accelerating the Availability of an Artificial Pancreas: A Roadmap to Better Diabetes Outcomes," Diabetes Technology & Therapeutics, vol. 11, Suppl 1, DOI: 10.1089/dia.2009.0031, S-113-S-119, 10 pages (2009).
Lesperance, et al., "Calibration of the Continuous Glucose Monitoring System for Transient Glucose Monitoring", Diabetes Technology & Therapeutics, vol. 9, No. 2, pp. 183-190 (2007).
Ley, "Continuous Glucose Monitoring: A Movie is Worth a Thousand Pictures a Review of the Medtronic Guardian REAL-time system," https://nfb.org/images/nfb/publications/vod/vod_22_4/vodfal0702.htm, 3 pages (2021).
McDaniel et al., "Remote Management of Cardiac Patients, The Forefront of a New Standard," Modern Healthcare, 6 pages, Nov. 14, 2011.
Murphy et al., "Closed-Loop Insulin Delivery During Pregnancy complicated by Type 1 Diabetes," Emerging Treatments and Technologies, Diabetes Care, vol. 34, 406-411 (2011).
MySentry™ User Guide, Medronic Minimed, 80 pages (2010).
Padgette et al., "Guide to Bluetooth Security, Recommendations of the National Institute of Standards and Technology," NET Special Publication 800421 Revision National Institute of Standards and Technology, U.S. Department of Commerce, 48 pages (2012).
Pickup, "Semi-Closed-Loop Insulin Delivery Systems: Early Experience with Low-Glucose Insulin Suspend Pumps," Diabetes Technology & Therapeutics, vol. 13, No. 7, DOI: 10.1089/dia.2011.0103, 695-698 (2011).
Place et al., "DiAs Web Monitoring: A Real-Time Remote Monitoring System Designed for Artificial Pancreas Outpatient Trials," Journal of Diabetes Science and Technology vol. 7, Issue 6, 1427-1435 (2013).
Project Status Update, Glucose Sensor Applicator Dexcom (project #2554), Design Concepts, Inc., 6 pages (2014).
Scheduling Order, *Abbott Diabetes Care Inc* v. *Dexcom, Inc.*, C.A. No. 23-239 (KAJ), 14 pages, Sep. 19, 2023.
Schlosser, et al., "Biocompatibility of Active Implantable Devices", Biosensors in the Body: Continuous in vivo Monitoring, 34 pages (1997).
Seagrove Partners, International Diabetes Device, 2022 Blue Book dated 2022, 143 pages in *Abbott Diabetes Care Inc., et al.* v. *Dexcom, Inc.*, Case No. 1:21-cv-00977-KAJ (District of Delaware).
Steil et al., "Feasibility of Automating Insulin Delivery for the Treatment of Type 1 Diabetes," Diabetes, vol. 55, 3344-3350 (2006).
Weinstein et al., "Diabetes Care, ADA 2006: Spotlight on Continuous Glucose Monitoring," JP Morgan, North America Equity Research, 16 pages, Jun. 11, 2006.
Weinzimer et al., "Fully Automated Closed-Loop Insulin Delivery Versus Semiautomated Hybrid Control in Pediatric Patients with Type 1 Diabetes Using an Artificial Pancreas," Emerging Treatments and Technologies, Diabetes Care, vol. 31, No. 5, 934-939 (2008).
Wettlaufer, "merlin.net Automation of External Reports Verification Process," A Thesis Presented to the Faculty of California Polytechnic State University, San Luis Obispo, 53 pages, Jan. 2010.
Wilson et al., Chapter 1, "Introduction to the Glucose Sensing Problem," In Vivo Glucose Sensing, 32 pages (2010).
Wisniewski, et al., "Characterization of implantable biosensor membrane biofouling", Fresenius J Anal Chem, 366:611-621 (2000).
Zhang et al., "Bluetooth Low Energy for Wearable Sensor-based Healthcare Systems," 2014 Health Innovations and Point-of-Care Technologies Conference, 251-254 (2014).
Dock, E. et al., "Multivariate data analysis of dynamic amperometric biosensor responses from binary analyte mixtures—applications of sensitivity correction algorithms", Talanta, 65, 2005 pp. 298-305.
FreeStyle Navigator Continuous Glucose Monitoring System, Dept of Health & Human Services, Food and Drug Administration, Mar. 12, 2008, 8 pages.
Hoss, U. et al., "Continuous Glucose Monitoring in Subcutaneous Tissue Using Factory-Calibrated Sensors: A Pilot Study", 2010, vol. 12, No. 8, pp. 591-597.

(56) References Cited

OTHER PUBLICATIONS

Hoss, U. et al., "Factory-Calibrated Continuous Glucose Sensors: The Science Behind the Technology", Diabetes Technology & Therapeutics, 2017, vol. 19, Suppl. 2, pp. S44-S50.
Instruction for Use Dexcom™M STS™ Sensor, 51 pages (2006).
Schiavon, A method online for there prevention of the risk of glycerine shock in diabetic patients from data of monitoring continuous of the glucose [with English translation], 220 pages (2010).
Townsend, et al., Getting Started with Bluetooth Low Energy, Tools and Techniques for Low-Power Networking, O'Reilly, 180 pages (2014).
Wang, et al., NYIT School of Engineering and Computing Sciences, A Feasible IMD Communication Protocol: Security without Obscurity, 1 page (2015).
U.S. Appl. No. 60/687,199, filed Jun. 2, 2005, Ward, et al.
U.S. Appl. No. 61/155,889, filed Feb. 26, 2009, Hoss, et al.
Atanasov, et al., "Implantation of a refillable glucose monitoring-telemetry device", Biosensors & Bioelectronics, 12(7):669-680 (1997).
Bindra, "Development of potentially implantable glucose sensors", The University of Arizona, 227 pages (1990).
FreeStyle Navigator Continuous Glucose Monitoring System, User's Guide, Abbott Diabetes Care Inc., 38 pages (2008).
Guardian® REAL-Time, Continuous Glucose Monitoring System, User Guide, Medtronic MiniMed, Inc., 184 pages (2006).
Kerner, et al., The function of a hydrogen peroxide-detecting electroenzymatic glucose electrode is markedly impaired in human sub-cutaneous tissue and plasma, Biosensors & Bioelectronics, 8:473-482 (1993).
Koschinsky, et al., "Sensors for glucose monitoring: technical and clinical aspects", Diabetes/Metabolism Research and Reviews, 17:113-123 (2001).
Koschwanez, et al., "In vitro, in vivo and post explantation testing of glucose-detecting biosensors: Current methods and recommendations", Biomaterials, 28:3687-3703 (2007).
Moussy, et al. "Performance of Subcutaneously Implanted Needle-Type Glucose Sensors Employing a Novel Trilayer Coating", Anal. Chem., 65:2072-2077 (1993).
Pickup, et al., "In vivo glucose sensing for diabetes management: progress towards non-invasive monitoring", BMJ, 319, pp. 1-4 (1999).
Pickup, et al., "Responses and calibration of amperometric glucose sensors implanted in the subcutaneous tissue of man", Acta Diabetol, 30:143-148 (1993).
Ward, et al., "Rise in background current over time in a subcutaneous glucose sensor in the rabbit: relevance to calibration and accuracy", Biosensors & Bioelectronics, 15:53-61 (2000).
Wilson, et al., "Biosensors for real-time in vivo measurements", Biosensors and Bioelectronics, 20:2388-2403 (2005).
Wisniewski, et al., "Analyte flux through chronically implanted subcutaneous polyamide membranes differs in humans and rats", Am J Physiol Endocrinol Metab, 282:E1316-E1323 (2002).
Select pages from OneTouch Ultra Vue User Manual published on Oct. 1, 2009 (with English Translation), 4 pages.
File history of U.S. Appl. No. 61/551,773, filed Oct. 26, 2011.
Harvey, et al., Clinically Relevant Hypoglycemia Prediction Metrics for Event Mitigation, Diabetes Technology & Therapeutics. vol. 14, No. 8, pp. 719-727 (2012).
Hughes, et al., Hypoglycemia Prevention via Pump Attenuation and Red-Yellow-Green "Traffic" Lights Using Continuous Glucose Monitoring and Insulin Pump Data, Journal of Diabetes Science and Technology, vol. 4, Issue 5, pp. 1146-1155 (2010).
Premarket Approval Letter with Summary of Safety and Effectiveness Data for the Freestyle Navigator Continuous Glucose Monitor, Mar. 12, 2008 [34 pgs.].
Schiavon, An online method for prevention of the risk of glycemic shock in diabetic patients from continuous glucose monitoring data, 117 pages (2010) with English translation of summary attached.
User Guide for the Navigator Freestyle (Mar. 2008) [38 pgs.].
Certified U.S. Appl. No. 61/238,657, filed Aug. 31, 2009, 60 pages.
Declaration of Thomas Edward Foster of Taylor Wessing LLP, Hill House, 1 Little New St. London EC4A 3TR ("Taylor Wessing"), in Relation to STS-7 User's Guide, Jan. 30, 2024, 160 pages.
DexCom STS-7 Approval Order, Department of Health and Human Services, FDA, May 31, 2007, 7 pages.
FDA Premarket Approval PMA Order for the STS-7, 3 pages, May 31, 2007.
File History of U.S. Pat. No. 10,375,222, issued Aug. 6, 2019, 442 pages.
Hanson et al., "Comparison of Point Accuracy Between Two Widely Used Continuous Glucose Monitoring Systems", Journal of Diabetes Science and Technology, 2024, pp. 1-10.
NFC Forum, Bluetooth® Secure Simple Pairing Using NFC Application Document NFC ForumTM, NFCForum-AD-BTSSP_ 1_1, Jan. 9, 2014, 39 pages.
Omre, Bluetooth Low Energy: Wireless Connectivity for Medical Monitoring, Journal of Diabetes Science and Technology, vol. 4, Issue 2, 457-463 Mar. 2010.
Padgette et al., "Guide to Bluetooth Security, Recommendations of the National Institute of Standards and Technology," National Institute of Standards and Technology, U.S. Department of Commerce, Special Publication 800-121 Revision 1, 48 pages, May 2007.
Specification Bluetooth System Experience More, 134 pages, Jun. 2010.
Specification Bluetooth System Wireless connections, 92 pages, Nov. 2003.
Strömmer et al., "Application of Near Field Communication for Health Monitoring in Daily Life," Proceedings of the 28th IEEE FrC09.1 EMBS Annual International Conference New York City, USA, 3246-3249, Aug. 30-Sep. 3, 2006.
Wayback Machine internet archive of US FDA CDRH PMA Final Decisions Rendered, 21 pages, May 2007.
Wayback Machine internet archive of US FDA CDRH PMA for STS-7, May 31, 2007, 1 page.
Zhang et al., "Bluetooth Low Energy for Wearable Sensor-based Healthcare Systems," 2014 Health Innovations and Point-of-Care Technologies Conference Seattle, Washington USA, 251-254, Oct. 8-10, 2014.
Chen, et al., "A novel fault-tolerant sensor system for sensor drift compensation", Sensors and Actuators, A 147:623-632 (2008).
Gerritsen, et al., "Performance of subcutaneously implanted glucose sensors for continuous monitoring", The Netherlands Journal of Medicine, 54:167-179 (1999).
Kalivas, et al., "Compensation for Drift and Interferences in Multicomponent Analysis", Laboratory for Chemometrics, Department of Chemistry, University of Washington, 38 pages (1982).
Thévenot, et al., "Electrochemical Biosensors: Recommended Definitions and Classification (Technical Report)", Pure Appl. Chem. 71(12):2333-2348 (1999).
U.S. Appl. No. 12/842,013 Office Action mailed Aug. 26, 2015.
U.S. Appl. No. 12/842,013 Office Action mailed Mar. 23, 2016.
U.S. Appl. No. 12/842,013 Office Action mailed Nov. 6, 2014.
Walt, et al., "The chemistry of enzyme and protein immobilization with glutaraldehyde", Trends in Analytical Chemistry, 13(10):425-430 (1994).
Zhang, "Investigations of potentially implantable glucose sensors", University of Kansas, 24 pages (1991).
"DexCom's 7-Day STS Continuous Glucose Monitoring System", Jun. 1, 2007 https://newatlas.com/dexcoms-7-day-sts-continuous-glucose-monitoring-system/7376/ 1 page.
A Dictionary of Computer Science, Seventh Edition, Oxford University Press, "authentication", 3 pages (2016).
A Dictionary of Computing, Sixth Edition, Oxford University Press, "function" 3 pages (2008).
Ananthi, "A Text Book of Medical Instruments," New Age International (P) Limited, Publishers, 7 pages (2005).
"Biomedical Engineering Desk Reference," Elsevier, 5 pages (2009).
Burr et al., Electronic Authentication Guideline, NIST Special Publication 800-63-2, Nist U.S. Dept. of Commerce, Aug. 2013, 123 pages.
D'Imporzano, Dr., "Reaching More of the World," Johnson & Johnson Celebrating 125 Years, Annual Report 2010, 2 pages.

(56) References Cited

OTHER PUBLICATIONS

Dorland's Illustrated Medical 31st Edition Dictionary, definition of "fluid, interstitial", (2007), 3 pages.
Ericksen et al., "Orthospinology Procedures, An Evidence-Based Approach to Spinal Care," 6 pages (2007).
Forlenza, G.P., et al., "Factory-Calibrated Continuous Glucose Monitoring: How and Why It Works, and the Dangers of Reuse Beyond Approved Duration of Wear", Diabetes Technology & Therapeutics, vol. 21, No. 4, (2019) 13 pages.
"GlucoWatch® G2™ Biographer (GW2B) Alarm Reliability During Hypoglycemia in Children," Diabetes Technol Thee., 6(5): 559-566, 12 pages (Oct. 2004).
Hashimoto et al., "Examination of Usefulness of Color Indicator Function of OneTouch Ultra VueTM, Medicine and Pharmacy," D44-D43, Opposition EP 3 988 471 B1, Hoffmann Elite, 9 pages (with English Translation) (2010).
IEEE 100 The Authoritative Dictionary of IEEE Standards Terms, Seventh Ed., "authentication", 3 pages (2000).
Kamath et al., "Methods of Evaluating the Utility of Continuous Glucose Monitor Alerts," Journal of Diabetes Science and Technology, vol. 4, 1, 57-66, 10 pages (2010).
Medronic, Guardian REAL-Time, User Guide CGMS, 181 pages (2006).
Newton, Newton's Telecom Dictionary, 30th Upldated, Expanded, Aniversry Ed., "authenticate", 4 pages (2016).
OneTouch Handling Instructions, for self-examination glucose meter, 108 pages (2018).
OneTouch Handling Instructions, for self-examination glucose meter, English Abstract, 6 pages (2018).
OneTouch Ultra Vue™, 3 pages (2010).
Stephens Inc., Research Bulletin, "DexCom, Inc., A True Game Changer: The G6 Eliminates Fingersticks", (2018) 5 pages.
The American Heritage® Medical Dictionary, definition of "catheter" and "interstitial fluid", (2007), 4 pages.
Wiklund, "Medical Device and Equipment Design," 6 pages (1995).
"Abbott Receives CE Mark for Freestyle® Libre, A Revolutionary Glucose Monitoring System for People with Diabetes," 8 pages (2023).
ATTD Program, 4 pages (2009).
Boise, Interview with Dexcom CEO, Dexcom CEO Kevin Sayer Explains G6, 9 pages (2018).
Dexcom (DXCM) Company Profile, 2017 /Q4 Earnings call transcript, 12 pages (2017).
Dexcom G6 Continuous Glucose Monitoring System User Guide, 7 pages (2020).
Email communication from Sophie Hood, Jan. 24, 2023, 6 pages.
Hall, Interview with Kevin Sayer, President and CEO of Dexcom About the New Dexcom G6, College Diabetes Network, 6 pages (2021).
Hoss et al., "Continuous glucose monitoring in the tissue: Do we really need to calibrate in-vivo?," Diabetes Technology & Therapeutics, vol. 11, No. 2, (2009).
Omnipod image, Exhibit 182, 2 pages, Sep. 22, 2022.
Sayer, CGMS Changing Diabetes Management: Kevin Sayer, DIC Interview Transcript, Featuring Steve Freed, 11 pages (2019).
S&P Global Market Intelligence "DexCom, Inc. NasdaqGS:DXCM, Company Conference Presentation," 17 pages (2021).
S&P Global Market Intelligence "DexCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
Sonix, Dexcom CEO—Prime Position in Our Market—Mad Money—CNBC.mp4, 4 pages (2023).
U.S. Food & Drug Administration, "Deciding When to Submit a 510(k) for a Change to an Existing Device, Guidance for Industry and Food and Drug Administration Staff," 78 pages (2017).
U.S. Food & Drug Administration, "Deciding When to Submit a 510(k) for a Software Change to an Existing Device, Guidance for Industry and Food and Drug Administration Staff," 32 pages (2017).
Watkin, "An Introduction to Flash Glucose Monitoring," 16 pages (2013).

* cited by examiner

MODEL BASED VARIABLE RISK FALSE GLUCOSE THRESHOLD ALARM PREVENTION MECHANISM

PRIORITY

The present application is a continuation of U.S. patent application Ser. No. 15/916,258, filed Mar. 8, 2018, which is a continuation of U.S. patent application Ser. No. 15/487,365 filed Apr. 13, 2017, now U.S. Pat. No. 9,913,619, which is a continuation of U.S. patent application Ser. No. 14/128,583 filed Dec. 20, 2013, now U.S. Pat. No. 9,622,691, which is a national stage patent application under 35 U.S.C. § 371, which claims priority to PCT Application No. PCT/US2012/062541 filed Oct. 30, 2012, which claims priority to U.S. Provisional Application No. 61/553,931 filed Oct. 31, 2011, entitled "Model Based Variable Risk False Glucose Threshold Alarm Prevention Mechanism", the disclosure of which is incorporated herein by reference for all purposes.

BACKGROUND

The detection of the level of glucose or other analytes, such as lactate, oxygen or the like, in certain individuals is vitally important to their health. For example, the monitoring of glucose is particularly important to individuals with diabetes. Diabetics may need to monitor glucose levels to determine when insulin is needed to reduce glucose levels in their bodies or when additional glucose is needed to raise the level of glucose in their bodies.

Devices have been developed for continuous or automatic monitoring of analytes, such as glucose, in bodily fluid such as in the blood stream or in interstitial fluid. Some of these analyte measuring devices are configured so that at least a portion of the devices are positioned below a skin surface of a user, e.g., in a blood vessel or in the subcutaneous tissue of a user.

Ease of insertion and use, including minimal user intervention and on-body size and height (or thickness) of such transcutaneous or percutaneous medical devices that are worn on the body are important in usability, wearability, and comfort during the device usage. Moreover, for many of such medical devices that require a battery or a similar power source to perform the device specific operations, power management as well as shelf life is important.

SUMMARY

Embodiments include methods for determining when to activate an analyte alarm of a continuous analyte monitor. The methods may include receiving information from the continuous analyte monitor related to the user's analyte concentration, wherein the information is received at a data processing component. The methods may also include receiving information that is input by the user, and the information is related to the user's analyte concentration. The information that is input by the user can also be received at the data processing component. In addition, the methods may also include that the data processing component determines the best-estimate (BE) of the user's analyte concentration based upon the information from the continuous analyte monitor and information from the user. Further, the methods may include that at least one condition for activating the analyte alarm is determined by the data processing component. Furthermore, if the information related to the user's analyte concentration converges with the best-estimate of the user's analyte concentration then the data processing component can modify the at least one condition for activating the analyte alarm.

Embodiments further include an integrated analyte monitoring device assembly, that includes an analyte sensor for transcutaneous positioning through a skin layer and maintained in fluid contact with an interstitial fluid under the skin layer during a predetermined time period, the analyte sensor having a proximal portion and a distal portion, and sensor electronics coupled to the analyte sensor. The sensor electronics can include the sensor electronics comprising a circuit board having a conductive layer and a sensor antenna disposed on the conductive layer, one or more electrical contacts provided on the circuit board and coupled with the proximal portion of the analyte sensor to maintain continuous electrical communication, and a data processing component provided on the circuit board and in signal communication with the analyte sensor. The data processing component can be configured to execute one or more routines for processing signals received from the analyte sensor, control the transmission of data associated with the processed signals received from the analyte sensor to a remote location using the sensor antenna in response to a request signal received from the remote location. The data processing component may be further configured to receive information from the continuous analyte monitor related to the user's analyte concentration, receive data from the user related to the user's analyte concentration, determine a best-estimate of the user's analyte concentration based upon the data signal and user data received at the processor, determine at least one condition for activating an analyte alarm, modify the at least one condition for activating the analyte alarm if the information related to the user's analyte concentration converges with the best-estimate of the user's analyte concentration.

Additional embodiments include an integrated analyte monitoring device that can include a data processing component provided on the circuit board and in signal communication with an analyte sensor. The data processing component of the integrated analyte monitoring device may be configured to execute one or more routines for processing signals received from the analyte sensor, and control the transmission of data associated with the processed signals received from the analyte sensor to a remote location using the sensor antenna in response to a request signal received from the remote location. The data processing component may be additionally configured to receive information from the continuous analyte monitor related to the user's analyte concentration, as well as data from the user related to the user's analyte concentration. A determination of the best-estimate of the user's analyte concentration based upon the data signal and user data received at the processor, as well as at least one condition for activating an analyte, can also be accomplished using the data processing component. Still further, the data processing component can be configured to modify the at least one condition for activating the analyte alarm if the information related to the user's analyte concentration converges with the best-estimate of the user's analyte concentration.

These and other features, objects and advantages of the present disclosure will become apparent to those persons skilled in the art upon reading the details of the present disclosure as more fully described below.

INCORPORATION BY REFERENCE

Figure 1:
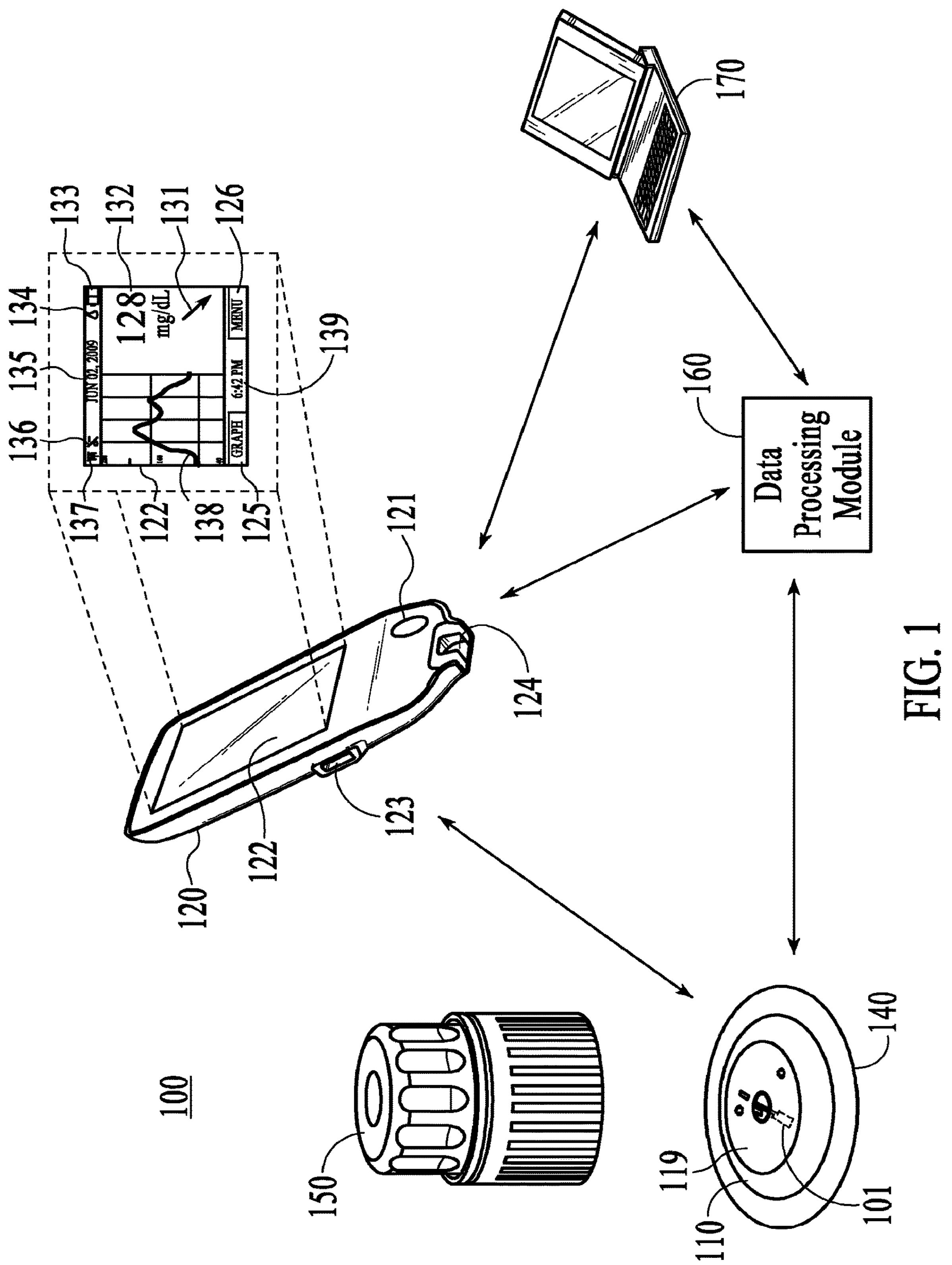
FIG. 1 shows a data monitoring and management system such as, for example, an analyte (e.g., glucose) monitoring system in accordance with certain embodiments of the present disclosure.

Patents, applications and/or publications described herein, including the following patents, applications and/or publications are incorporated herein by reference for all purposes: U.S. Pat. Nos. 4,545,382, 4,711,245, 5,262,035, 5,262,305, 5,264,104, 5,320,715, 5,356,786, 5,509,410, 5,543,326, 5,593,852, 5,601,435, 5,628,890, 5,820,551, 5,822,715, 5,899,855, 5,918,603, 6,071,391, 6,103,033, 6,120,676, 6,121,009, 6,134,461, 6,143,164, 6,144,837, 6,161,095, 6,175,752, 6,270,455, 6,284,478, 6,299,757, 6,338,790, 6,377,894, 6,461,496, 6,503,381, 6,514,460, 6,514,718, 6,540,891, 6,560,471, 6,579,690, 6,591,125, 6,592,745, 6,600,997, 6,605,200, 6,605,201, 6,616,819, 6,618,934, 6,650,471, 6,654,625, 6,676,816, 6,730,200, 6,736,957, 6,746,582, 6,749,740, 6,764,581, 6,773,671, 6,881,551, 6,893,545, 6,932,892, 6,932,894, 6,942,518, 7,041,468, 7,167,818, 7,299,082, and 7,866,026, and U.S. Patent Publication Nos. 2004/0186365, now U.S. Pat. No. 7,811,231, 2005/0182306, now U.S. Pat. No. 8,771,183, 2006/0025662, now U.S. Pat. No. 7,740,581, 2006/0091006, 2007/0056858, now U.S. Pat. No. 8,298,389, 2007/0068807, now U.S. Pat. No. 7,846,311, 2007/0095661, 2007/0108048, now U.S. Pat. No. 7,918,975, 2007/0199818, now U.S. Pat. No. 7,811,430, 2007/0227911, now U.S. Pat. No. 7,887,682, 2007/0233013, 2008/0066305, now U.S. Pat. No. 7,895,740, 2008/0081977, now U.S. Pat. No. 7,618,369, 2008/0102441, now U.S. Pat. No. 7,822,557, 2008/0148873, now U.S. Pat. No. 7,802,467, 2008/0161666, 2008/0267823, 2009/0054748, now U.S. Pat. No. 7,885,698, 2009/0294277, 2010/0213057, 2010/0081909, now U.S. Pat. No. 8,219,173, 2009/0247857, now U.S. Pat. No. 8,346,335, 2011/0106126, 2011/0082484, 2010/0326842, 2010/0198034, 2010/0324392, now U.S. Pat. No. 9,402,544, 2010/0230285, 2010/0313105, now U.S. Pat. No. 8,595,607, 2011/0213225, 2011/0021889, now U.S. Pat. No. 9,795,326, 2011/0193704, now U.S. Pat. No. 8,514,086, 2011/0190603, 2010/0317952, now U.S. Pat. No. 9,579,456, 2011/0191044, now U.S. Pat. No. 9,351,669, 2011/0257495, now U.S. Pat. No. 8,965,477, 2011/0288574, now U.S. Pat. No. 9,265,453, 2011/0319729, now U.S. Pat. No. 9,215,992, and 2012/0010642, now U.S. Pat. No. 9,186,098.

DETAILED DESCRIPTION

Within the scope of the present disclosure, there are provided devices, systems, kits and methods for providing compact, low profile, on-body physiological parameter monitoring device (physiological parameters such as for example, but not limited to analyte levels, temperature levels, heart rate, etc), configured for single or multiple use over a predetermined time period, which provide a low profile geometry, effective power management, improved shelf life, and ease and comfort of use including device positioning, and activation. Embodiments include an on-body assembly including a transcutaneously positioned analyte sensor and sensor electronics in a compact, low profile integrated assembly and coupled to an insertion device for deployment.

Before the present disclosure is described in additional detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

The figures shown herein are not necessarily drawn to scale, with some components and features being exaggerated for clarity.

Generally, embodiments of the present disclosure relate to methods and devices for detecting at least one analyte, such as glucose, in body fluid. In certain embodiments, the present disclosure relates to the continuous and/or automatic in vivo monitoring of the level of an analyte using an analyte sensor.

Accordingly, embodiments include analyte monitoring devices and systems that include an analyte sensor—at least a portion of which is positionable beneath the skin of the user—for the in vivo detection of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a transmitter, receiver, transceiver, processor, etc. The sensor may be, for example, subcutaneously positionable in a patient for the continuous or periodic monitoring of a level of an analyte in a patient's interstitial fluid.

For the purposes of this description, continuous monitoring and periodic monitoring will be used interchangeably, unless noted otherwise. Discrete monitoring as used herein includes the acquisition or reception of monitored analyte data where real time monitored analyte level information is received or acquired on demand or in response to a request to an analyte monitoring device including sensor and sensor electronics. That is, embodiments include analyte sensors and sensor electronics which sample and process analyte related information based on a programmed or programmable schedule such as every minute, every five minutes and so on. Such analyte monitoring routines may be reported or transmitted in real time to a receiver unit/reader device at the time of data sampling and processing. Alternatively, as discussed, the continuously sampled analyte data and processed analyte related signals may be stored and transmitted to a remote location such as the receiver unit, data processing module, the data processing terminal, the reader device or the remote terminal in response to a request for such information from the remote location. The analyte level may be correlated and/or converted to analyte levels in blood or other fluids. In certain embodiments, an analyte sensor may be positioned in contact with interstitial fluid to detect the level of glucose, and the detected glucose may be used to infer the glucose level in the patient's bloodstream. Analyte sensors may be insertable into a vein, artery, or other portion of the body containing fluid. Embodiments of the analyte sensors of the subject disclosure may be configured for monitoring the level of the analyte over a time period which may range from minutes, hours, days, weeks, or longer.

Of interest are analyte sensors, such as glucose sensors, that are capable of in vivo detection of an analyte for about one hour or more, e.g., about a few hours or more, e.g., about a few days of more, e.g., about three or more days, e.g., about five days or more, e.g., about seven days or more, e.g., about several weeks or at least one month. Future analyte levels may be predicted based on information obtained, e.g., the current analyte level at time $t_0$, the rate of change of the analyte, etc. Predictive alarms may notify the user of predicted analyte levels that may be of concern prior in advance of the analyte level reaching the future level. This enables the user an opportunity to take corrective action. Embodiments include transmission of the acquired real time analyte information on-demand from the user (using for example, the reader device/receiver unit positioned in close proximity to the low profile on-body patch device), storage of the acquired real time analyte information, and subsequent transmission based on retrieval from the storage device (such as a memory device).

FIG. 1 shows an exemplary in vivo-based analyte monitoring system 100 in accordance with embodiments of the present disclosure. As shown, in certain embodiments, analyte monitoring system 100 includes on body electronics 110 electrically coupled to in vivo analyte sensor 101 (a proximal portion of which is shown in FIG. 1) and attached to adhesive layer 140 for attachment on a skin surface on the body of a user. On body electronics 110 includes on body housing 119, that defines an interior compartment. Also shown in FIG. 1 is insertion device 150 that, when operated, transcutaneously positions a portion of analyte sensor 101 through a skin surface and in fluid contact with ISF, and positions on body electronics 110 and adhesive layer 140 on a skin surface. In certain embodiments, on body electronics 110, analyte sensor 101 and adhesive layer 140 are sealed within the housing of insertion device 150 before use, and in certain embodiments, adhesive layer 140 is also sealed within the housing or itself provides a terminal seal of the insertion device 150. Devices, systems and methods that may be used with embodiments herein are described, e.g., in U.S. patent application Ser. No. 12/698,129, now U.S. Pat. No. 9,402,544, Ser. No. 13/071,461, now U.S. Pat. No. 9,215,992, Ser. No. 13/071,487, now U.S. Pat. No. 9,265,453, and Ser. No. 13/071,497, now U.S. Pat. No. 9,186,098, the disclosures of each of which are incorporated herein by reference for all purposes.

Referring back to the FIG. 1, analyte monitoring system 100 includes display device 120 or receiver/reader unit, which includes a display 122 to output information to the user, an input component 121 such as a button, actuator, a touch sensitive switch, a capacitive switch, pressure sensitive switch, jog wheel or the like, to input data or command to display device 120 or otherwise control the operation of display device 120. It is noted that some embodiments may include display-less devices or devices without any user interface components. These devices may be functionalized to store data as a data logger and/or provide a conduit to transfer data from on body electronics and/or a display-less device to another device and/or location. Embodiments will be described herein as display devices for exemplary purposes which are in no way intended to limit the embodiments of the present disclosure. It will be apparent that display-less devices may also be used in certain embodiments.

In certain embodiments, on body electronics 110 may be configured to store some or all of the monitored analyte related data received from analyte sensor 101 in a memory during the monitoring time period, and maintain it in memory until the usage period ends. In such embodiments, stored data is retrieved from on body electronics 110 at the conclusion of the monitoring time period, for example, after removing analyte sensor 101 from the user by detaching on body electronics 110 from the skin surface where it was positioned during the monitoring time period. In such data logging configurations, real time monitored analyte level is not communicated to display device 120 during the monitoring period or otherwise transmitted from on body electronics 110, but rather, retrieved from on body electronics 110 after the monitoring time period.

In certain embodiments, input component 121 of display device 120 may include a microphone and display device 120 may include software configured to analyze audio input received from the microphone, such that functions and operation of the display device 120 may be controlled by voice commands. In certain embodiments, an output component of display device 120 includes a speaker for outputting information as audible signals. Similar voice responsive components such as a speaker, microphone and software routines to generate, process and store voice driven signals may be provided to on body electronics 110.

In certain embodiments, display 122 and input component 121 may be integrated into a single component, for example a display that can detect the presence and location of a physical contact touch upon the display such as a touch screen user interface. In such embodiments, the user may control the operation of display device 120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Display device 120 also includes data communication port 123 for wired data communication with external devices such as remote terminal (personal computer) 170, for example. Example embodiments of the data communication port 123 include USB port, mini USB port, RS-232 port, Ethernet port, FireWire (IEEE 1394) port, or other similar data communication ports configured to connect to the compatible data cables. Display device 120 may also include an integrated in vitro glucose meter, including in vitro test strip port 124 to receive an in vitro glucose test strip for performing in vitro blood glucose measurements.

Referring still to FIG. 1, display 122 in certain embodiments is configured to display a variety of information—some or all of which may be displayed at the same or different time on display 122. In certain embodiments the displayed information is user-selectable so that a user can customize the information shown on a given display screen. Display 122 may include but is not limited to graphical display 138, for example, providing a graphical output of glucose values over a monitored time period (which may show important markers such as meals, exercise, sleep, heart rate, blood pressure, etc), a numerical display 132, for example, providing monitored glucose values (acquired or received in response to the request for the information), and trend or directional arrow display 131 that indicates a rate of analyte change and/or a rate of the rate of analyte change, e.g., by moving locations on display 122. Additionally, display 122 may include an alarm display that annunciates.

As further shown in FIG. 1, display 122 may also include date display 135 providing for example, date information for the user, time of day information display 139 providing time of day information to the user, battery level indicator display 133 which graphically shows the condition of the battery (rechargeable or disposable) of the display device 120, sensor calibration status icon display 134 for example, in monitoring systems that require periodic, routine or a predetermined number of user calibration events, notifying the user that the analyte sensor calibration is necessary, audio/vibratory settings icon display 136 for displaying the status of the audio/vibratory output or alarm state, and wireless connectivity status icon display 137 that provides indication of wireless communication connection with other devices such as on body electronics, data processing module 160, and/or remote terminal 170. As additionally shown in FIG. 1, display 122 may further include simulated touch screen button 125, 126 for accessing menus, changing display graph output configurations or otherwise for controlling the operation of display device 120.

Referring back to FIG. 1, in certain embodiments, display 122 of display device 120 may be additionally, or instead of visual display, configured to output alarm notifications such as alarm and/or alert notifications, glucose values etc, which may be audible, tactile, or any combination thereof. In one aspect, the display device 120 may include other output components such as a speaker, vibratory output component and the like to provide audible and/or vibratory output indication to the user in addition to the visual output indication provided on display 122. Further details and other display embodiments can be found in, e.g., U.S. patent application Ser. No. 12/871,901, now U.S. Pat. No. 8,514,086, and U.S. Provisional Application Nos. 61/238,672, 61/247,541, 61/297,625, the disclosures of each of which are incorporated herein by reference for all purposes.

After the positioning of on body electronics 110 on the skin surface and analyte sensor 101 in vivo to establish fluid contact with ISF (or other appropriate body fluid), on body electronics 110 in certain embodiments is configured to wirelessly communicate analyte related data (such as, for example, data corresponding to monitored analyte level and/or monitored temperature data, and/or stored historical analyte related data) when on body electronics 110 receives a command or request signal from display device 120. In certain embodiments, on body electronics 110 may be configured to at least periodically broadcast real time data associated with a monitored analyte level received by display device 120, when display device 120 is within communication range of the data broadcast from on body electronics 110, i.e., it does not need a command or request from display device 120 to send information.

For example, when within a communication range, display device 120 may be configured to automatically transmit one or more commands to on body electronics 110 to initiate data transfer, and in response, on body electronics 110 may be configured to wirelessly transmit stored analyte related data collected during the monitoring time period to display device 120. In certain embodiments, the data transfer may be user initiated. Display device 120 may in turn be connected to a remote terminal 170, such as a personal computer, and functions as a data conduit to transfer the stored analyte level information from the on body electronics 110 to remote terminal 170. In certain embodiments, the received data from the on body electronics 110 may be stored (permanently or temporarily) in one or more memory of the display device 120. In certain other embodiments, display device 120 is configured as a data conduit to pass the data received from on body electronics 110 to remote terminal 170 that is connected to display device 120.

Referring still to FIG. 1, also shown in analyte monitoring system 100 are data processing module 160 and remote terminal 170. Remote terminal 170 may include a personal computer, a server terminal, a laptop computer or other suitable data processing devices including software for data management and analysis and communication with the components in the analyte monitoring system 100. For example, remote terminal 170 may be connected to a local area network (LAN), a wide area network (WAN), or other data network for uni-directional or bi-directional data communication between remote terminal 170 and display device 120 and/or data processing module 160.

Remote terminal 170 in certain embodiments may include one or more computer terminals located at a physician's office or a hospital. For example, remote terminal 170 may be located at a location other than the location of display device 120. Remote terminal 170 and display device 120 could be in different rooms or different buildings. Remote terminal 170 and display device 120 could be at least about one mile apart, e.g., at least about 10 miles apart, e.g., at least about 100 miles apart. For example, remote terminal 170 could be in the same city as display device 120, remote terminal 170 could be in a different city than display device 120, remote terminal 170 could be in the same state as display device 120, remote terminal 170 could be in a different state than display device 120, remote terminal 170 could be in the same country as display device 120, or remote terminal 170 could be in a different country than display device 120, for example.

In certain embodiments, a separate, optional data communication/processing device such as data processing module 160 may be provided in analyte monitoring system 100. Data processing module 160 may include components to communicate using one or more wireless communication protocols such as, for example, but not limited to, infrared (IR) protocol, Bluetooth® protocol, Zigbee® protocol, and 802.11 wireless LAN protocol. Additional description of communication protocols including those based on Bluetooth® protocol and/or Zigbee® protocol can be found in U.S. Patent Publication No. 2006/0193375 incorporated herein by reference for all purposes. Data processing module 160 may further include communication ports, drivers or connectors to establish wired communication with one or more of display device 120, on body electronics 110, or remote terminal 170 including, for example, but not limited to USB connector and/or USB port, Ethernet connector and/or port, FireWire (IEEE 1394) connector and/or port, or RS-232 port and/or connector.

In certain embodiments, data processing module 160 is programmed to transmit a polling or query signal to on body electronics 110 at a predetermined time interval (e.g., once every minute, once every five minutes, or the like), and in response, receive the monitored analyte level information from on body electronics 110. Data processing module 160 stores in its memory the received analyte level information, and/or relays or retransmits the received information to another device such as display device 120. More specifically in certain embodiments, data processing module 160 may be configured as a data relay device to retransmit or pass through the received analyte level data from on body electronics 110 to display device 120 or a remote terminal (for example, over a data network such as a cellular or WiFi data network) or both.

In certain embodiments, on body electronics 110 and data processing module 160 may be positioned on the skin surface of the user within a predetermined distance of each other (for example, about 1-12 inches, or about 1-10 inches, or about 1-7 inches, or about 1-5 inches) such that periodic communication between on body electronics 110 and data processing module 160 is maintained. Alternatively, data processing module 160 may be worn on a belt or clothing item of the user, such that the desired distance for communication between the on body electronics 110 and data processing module 160 for data communication is maintained. In a further aspect, the housing of data processing module 160 may be configured to couple to or engage with on body electronics 110 such that the two devices are combined or integrated as a single assembly and positioned on the skin surface. In further embodiments, data processing module 160 is detachably engaged or connected to on body electronics 110 providing additional modularity such that data processing module 160 may be optionally removed or reattached as desired.

Referring again to FIG. 1, in certain embodiments, data processing module 160 is programmed to transmit a command or signal to on body electronics 110 at a predetermined time interval such as once every minute, or once every 5 minutes or once every 30 minutes or any other suitable or desired programmable time interval to request analyte related data from on body electronics 110. When data processing module 160 receives the requested analyte related data, it stores the received data. In this manner, analyte monitoring system 100 may be configured to receive the continuously monitored analyte related information at the programmed or programmable time interval, which is stored and/or displayed to the user. The stored data in data processing module 160 may be subsequently provided or transmitted to display device 120, remote terminal 170 or the like for subsequent data analysis such as identifying frequency of periods of glycemic level excursions over the monitored time period, or the frequency of the alarm event occurrence during the monitored time period, for example, to improve therapy related decisions. Using this information, the doctor, healthcare provider or the user may adjust or recommend modification to the diet, daily habits and routines such as exercise, and the like.

In another embodiment, data processing module 160 transmits a command or signal to on body electronics 110 to receive the analyte related data in response to a user activation of a switch provided on data processing module 160 or a user initiated command received from display device 120. In further embodiments, data processing module 160 is configured to transmit a command or signal to on body electronics 110 in response to receiving a user initiated command only after a predetermined time interval has elapsed. For example, in certain embodiments, if the user does not initiate communication within a programmed time period, such as, for example about 5 hours from last communication (or 10 hours from the last communication, or 24 hours from the last communication), the data processing module 160 may be programmed to automatically transmit a request command or signal to on body electronics 110. Alternatively, data processing module 160 may be programmed to activate an alarm to notify the user that a predetermined time period of time has elapsed since the last communication between the data processing module 160 and on body electronics 110. In this manner, users or healthcare providers may program or configure data processing module 160 to provide certain compliance with analyte monitoring regimen, so that frequent determination of analyte levels is maintained or performed by the user.

In certain embodiments, when a programmed or programmable alarm condition is detected (for example, a detected glucose level monitored by analyte sensor 101 that is outside a predetermined acceptable range indicating a physiological condition which requires attention or intervention for medical treatment or analysis (for example, a hypoglycemic condition, a hyperglycemic condition, an impending hyperglycemic condition or an impending hypoglycemic condition)), the one or more output indications may be generated by the control logic or processor of the on body electronics 110 and output to the user on a user interface of on body electronics 110 so that corrective action may be timely taken. In addition to or alternatively, if display device 120 is within communication range, the output indications or alarm data may be communicated to display device 120 whose processor, upon detection of the alarm data reception, controls the display 122 to output one or more notification.

In certain embodiments, control logic or microprocessors of on body electronics 110 include software programs to determine future or anticipated analyte levels based on information obtained from analyte sensor 101, e.g., the current analyte level, the rate of change of the analyte level, the acceleration of the analyte level change, and/or analyte trend information determined based on stored monitored analyte data providing a historical trend or direction of analyte level fluctuation as function time during monitored time period. Predictive alarm parameters may be programmed or programmable in display device 120, or the on body electronics 110, or both, and output to the user in advance of anticipating the user's analyte level reaching the future level. This provides the user an opportunity to take timely corrective action.

Information, such as variation or fluctuation of the monitored analyte level as a function of time over the monitored time period providing analyte trend information, for example, may be determined by one or more control logic or microprocessors of display device 120, data processing module 160, and/or remote terminal 170, and/or on body electronics 110. Such information may be displayed as, for example, a graph (such as a line graph) to indicate to the user the current and/or historical and/or and predicted future analyte levels as measured and predicted by the analyte monitoring system 100. Such information may also be displayed as directional arrows (for example, see trend or directional arrow display 131) or other icon(s), e.g., the position of which on the screen relative to a reference point indicated whether the analyte level is increasing or decreasing as well as the acceleration or deceleration of the increase or decrease in analyte level. This information may be utilized by the user to determine any necessary corrective actions to ensure the analyte level remains within an acceptable and/or clinically safe range. Other visual indicators, including colors, flashing, fading, etc., as well as audio indicators including a change in pitch, volume, or tone of an audio output and/or vibratory or other tactile indicators may also be incorporated into the display of trend data as means of notifying the user of the current level and/or direction and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, the system 100 may include an algorithm stored on computer readable medium to determine the time it will take to reach a clinically significant level and will output notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring again back to FIG. 1, in certain embodiments, software algorithm(s) for execution by data processing module 160 may be stored in an external memory device such as an SD card, microSD card, compact flash card, XD card, Memory Stick card, Memory Stick Duo card, or USB memory stick/device including executable programs stored in such devices for execution upon connection to the respective one or more of the on body electronics 110, remote terminal 170 or display device 120. In a further aspect, software algorithms for execution by data processing module 160 may be provided to a communication device such as a mobile telephone including, for example, WiFi or Internet enabled smart phones or personal digital assistants (PDAs) as a downloadable application for execution by the downloading communication device.

Examples of smart phones include Windows®, Android™, iPhone® operating system, Palm® WebOS™, Blackberry® operating system, or Symbian® operating system based mobile telephones with data network connectivity functionality for data communication over an internet connection and/or a local area network (LAN). PDAs as described above include, for example, portable electronic devices including one or more microprocessors and data communication capability with a user interface (e.g., display/output unit and/or input unit, and configured for performing data processing, data upload/download over the internet, for example. In such embodiments, remote terminal 170 may be configured to provide the executable application software to the one or more of the communication devices described above when communication between the remote terminal 170 and the devices are established.

In still further embodiments, executable software applications may be provided over-the-air (OTA) as an OTA download such that wired connection to remote terminal 170 is not necessary. For example, executable applications may be automatically downloaded as software download to the communication device, and depending upon the configuration of the communication device, installed on the device for use automatically, or based on user confirmation or acknowledgement on the communication device to execute the installation of the application. The OTA download and installation of software may include software applications and/or routines that are updates or upgrades to the existing functions or features of data processing module 160 and/or display device 120.

Referring back to remote terminal 170 of FIG. 1, in certain embodiments, new software and/or software updates such as software patches or fixes, firmware updates or software driver upgrades, among others, for display device 120 and/or on body electronics 110 and/or data processing module 160 may be provided by remote terminal 170 when communication between the remote terminal 170 and display device 120 and/or data processing module 160 is established. For example, software upgrades, executable programming changes or modification for on body electronics 110 may be received from remote terminal 170 by one or more of display device 120 or data processing module 160, and thereafter, provided to on body electronics 110 to update its software or programmable functions. For example, in certain embodiments, software received and installed in on body electronics 110 may include software bug fixes, modification to the previously installed software parameters (modification to analyte related data storage time interval, resetting or adjusting time base or information of on body electronics 110, modification to the transmitted data type, data transmission sequence, or data storage time period, among others). Additional details describing field upgradability of software of portable electronic devices, and data processing are provided in U.S. application Ser. Nos. 12/698,124, 12/794,721, now U.S. Pat. No. 8,595,607, Ser. Nos. 12/699,653, and 12/699,844, now U.S. Pat. No. 8,930,203, and U.S. Provisional Application Nos. 61/359,265, and 61/325,155 the disclosure of which is incorporated by reference herein for all purposes.

Generally, the concentration of glucose in a person changes as a result of one or more external influences such as meals and exercise, and also changes resulting from various physiological mechanisms such as stress, illness, menstrual cycle and the like. In a person with diabetes, such changes can necessitate monitoring the person's glucose level and administering insulin or other glucose level altering drugs, such as, e.g., a glucose lowering or raising drug, as needed to maintain the person's glucose level with a desired range. In any of the above examples, the system 100 is thus configured to determine, based on some amount of patient-specific information, an appropriate amount, type and/or timing of insulin or other glucose level altering drug to administer in order to maintain normal glucose levels without causing hypoglycemia or hyperglycemia. In some embodiments, the system 100 is configured to control one or more external insulin pumps, such as, e.g., subcutaneous, transcutaneous or transdermal pumps, and/or implanted insulin pumps to automatically infuse or otherwise supply the appropriate amount and type of insulin to the user's body in the form of one or more insulin boluses.

In another embodiment, the system 100 is configured to display or otherwise notify the user of the appropriate amount, type, and/or timing of the insulin in the form of an insulin delivery or administration recommendation or instruction. In such embodiments, the hardware and/or software forming system 100 allows the user to accept the recommended insulin amount, type, and/or timing, or to reject it. If the recommendation is accepted by the user, the system 100, in one embodiment, automatically infuses or otherwise provides the appropriate amount and type of insulin to the user's body in the form of one or more insulin boluses. If, on the other hand, the user rejects the insulin recommendation, the hardware and/or software forming system 100 allows the user to override the system 100 and manually enter values for insulin bolus quantity, type, and/or timing in the system 100. The system 100 is thus configured by the user to automatically infuse or otherwise provide the user specified amount, type, and/or timing of the insulin to the user's body in the form of one or more insulin boluses.

Alternatively, the appropriate amount and type of insulin corresponding to the insulin recommendation displayed by the system 100 may be manually injected into, or otherwise administered to, the user's body. It will be understood, however, that the system 100 may alternatively or additionally be configured in like manner to determine, recommend, and/or deliver other types of medication to a patient.

The system 100 is operable, as just described, to determine and either recommend or administer an appropriate amount of insulin or other glucose level lowering drug to the patient in the form of one or more insulin boluses. In order to determine appropriate amounts of insulin to be delivered or administered to the user to bring the user's glucose level within an acceptable range, the system 100 requires at least some information relating to one or more external influences and/or various physiological mechanisms associated with the user. For example, the system 100 may receive information if the user is about to ingest, is ingesting, or has recently ingested, a meal or snack, to determine an appropriate amount, type and/or timing of one or more meal compensation boluses of insulin. When a person ingests food in the form of a meal or snack, the person's body reacts by absorbing glucose from the meal or snack over time. For purposes of this document, any ingesting of food may be referred hereinafter as a "meal," and the term "meal" therefore encompasses traditional meals, such as, e.g., breakfast, lunch, and dinner, as well as intermediate snacks, drinks, and the like.

Figure 2:
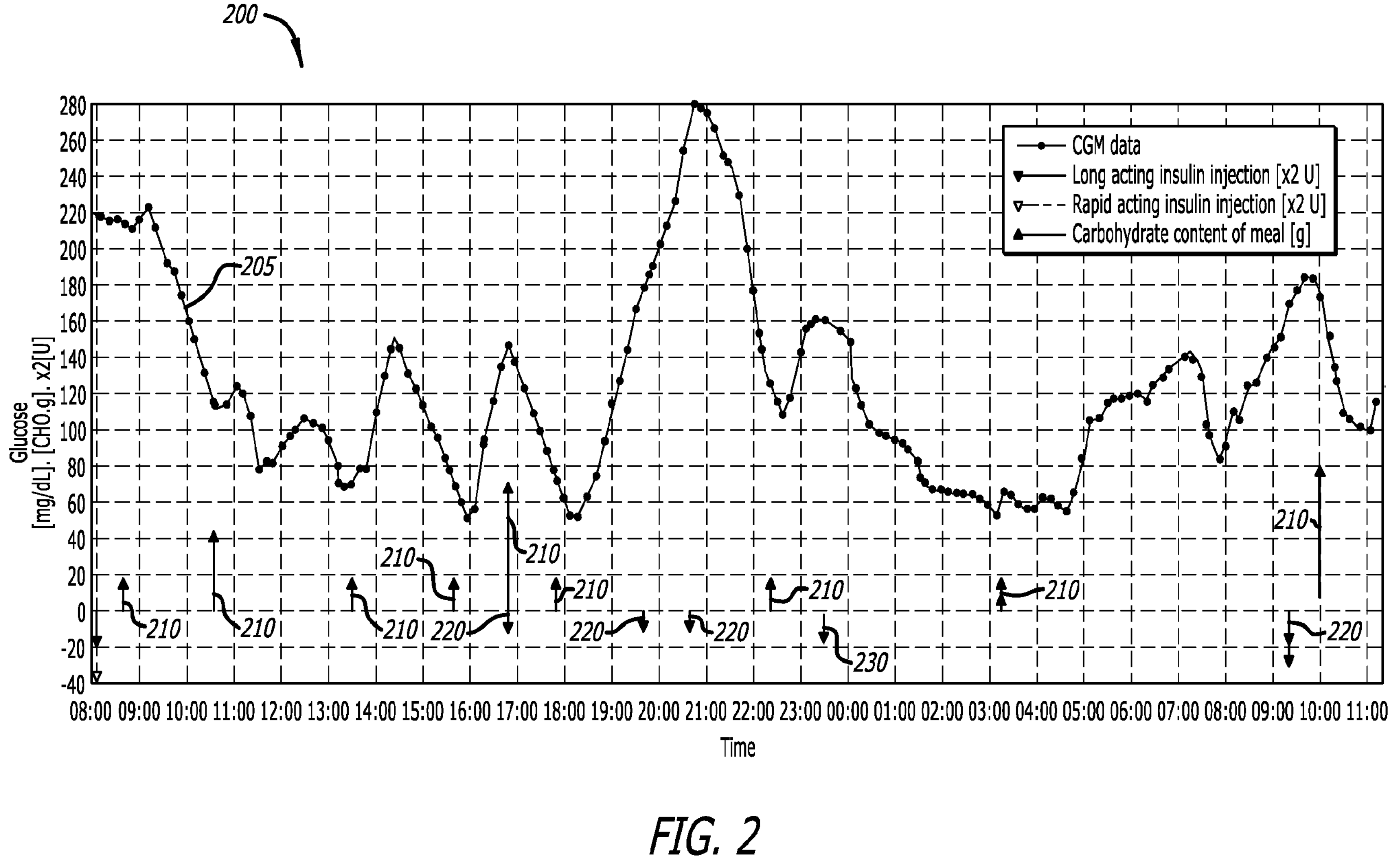
FIG. 2 is a graphical representation of a glucose profile showing a user's glucose level measured using a CGM sensor as a function of time, and also depicting the variation of the glucose level as a function of carbohydrate intake and insulin administration.

FIG. 2 depicts a typical glucose profile 200 for a user determined using a CGM sensor, such as sensor 101 with on body electronics 110. The graph 205 plots the measured glucose level as a function of time. This profile shows the effect on glucose level from various actions, such as meal/carbohydrate intake 210, and the delivery of rapid acting insulin 220 and long acting insulin 230.

The general shape of a glucose profile for any person rises following ingestion of a meal, peaks at some measureable time following the meal, and then decreases thereafter. The speed, e.g., the rate from beginning to completion, of any one glucose absorption profile typically varies for a person by meal composition, meal type or time (e.g., breakfast, lunch, dinner, or snack), and/or according to one or more other factors, and may also vary from day-to-day under otherwise identical meal circumstances. Generally, the information relating to such meal intake information supplied by the user to the system 100 should contain, either explicitly or implicitly, an estimate of the carbohydrate content of the meal or snack, corresponding to the amount of carbohydrates that the user is about to ingest, is ingesting, or has recently ingested, as well as an estimate of the speed of overall glucose absorption from the meal by the user.

The estimate of the amount of carbohydrates that the patient is about to ingest, is ingesting, or has recently ingested, may be provided by the user in any of the various forms. Examples include, but are not limited to, a direct estimate or carbohydrate weight (e.g., in units of grams or other convenient weight measure), an amount of carbohydrates relative to a reference amount (e.g., a dimensionless amount), an estimate of meal or snack size (e.g., a dimensionless amount or units of serving), and an estimate of meal or snack size relative to a reference snack size (e.g., a dimensionless amount). Other forms of providing for user input of carbohydrate content of a meal or snack will occur to those skilled in the art, and any such other forms are contemplated by this disclosure.

The estimate of the speed of overall glucose absorption from the meal by the user may likewise be provided by the user in any of various forms. For example, for a specified value of the expected speed of overall glucose absorption, the glucose absorption profile captures the speed of absorption of the meal taken by the user. As another example, the speed of overall glucose absorption from the meal by the user also includes time duration between ingesting of the meal by a user and the peak glucose absorption of the meal by that user, which captures the duration of the meal taken by the user. The speed of overall glucose absorption may thus be expressed in the form of meal speed or duration. Examples of the expected speed of overall glucose absorption parameter in this case may include, but are not limited to, a compound parameter corresponding to an estimate of the meal speed or duration (e.g., units of time), a compound parameter corresponding to meal speed or duration relative to a reference meal speed or duration (e.g., dimensionless), or the like.

As another example of providing the estimate of the expected speed of overall glucose absorption parameter, the shape and duration of the glucose absorption profile may be mapped to the composition of the meal. Examples of the expected speed of overall glucose absorption parameter in this case may include, but are not limited to, an estimate of fat amount, protein amount, and carbohydrate amount (e.g., in units of grams) in conjunction with a carbohydrate content estimate in the form of meal size or relative meal size, an estimate of fat amount and carbohydrate amount relative to reference fat, protein, and carbohydrate amounts in conjunction with a carbohydrate content estimate in the form of meal size or relative meal size, and an estimate of total glycemic index of the meal or snack (e.g., dimensionless), wherein the term "total glycemic index" is defined for purposes of this disclosure as a parameter that ranks meals and snacks by the speed at which the meals or snacks cause the user's glucose level to rise. Thus, for example, a meal or snack having a low glycemic index produces a gradual rise in glucose level whereas a meal or snack having a high glycemic index produces a fast rise in glucose level. One exemplary measure of total glycemic index may be, but is not limited to, the ratio of carbohydrates absorbed from the meal and a reference value, such as derived from pure sugar or white bread, over a specified time period (e.g., 2 hours). Other forms of providing for user input of the expected overall speed of glucose absorption from the meal by the patient, and/or for providing for user input of the expected shape and duration of the glucose absorption profile generally will occur to those skilled in the art, and any such other forms are contemplated by this disclosure.

Generally, the concentration of glucose in a person with diabetes changes as a result of one or more external influences such as meals and/or exercise, and may also change resulting from various physiological mechanisms such as stress, menstrual cycle and/or illness. In any of the above examples, the system 100 responds to the measured glucose by determining the appropriate amount of insulin to administer in order to maintain normal glucose levels without causing hypoglycemia. In some embodiments, the system 100 is implemented as a discreet system with an appropriate sampling rate, which may be periodic, aperiodic, or triggered, although other continuous systems or hybrid systems may alternatively be implemented as described above.

As one example of a conventional diabetes control system, one or more software algorithms may include a collection of rule sets which use (1) glucose information, (2) insulin delivery information, and/or (3) user inputs such as mean intake, exercise, stress, illness and/or other physiological properties to provide therapy, and the like, to manage the user's glucose level. The rule sets are generally based on observations and clinical practices as well as mathematical models derived through or based on analysis of physiological mechanisms obtained from clinical studies. In the exemplary system, models of insulin pharmacokinetics, pharmacodynamics, glucose dynamics, meal absorption and exercise responses of individual patients are used to determine the timing and the amount of insulin to be delivered. A learning module may be provided to allow adjustment of the model parameters when the patient's overall performance metric degrades such as, for example, adaptive algorithms, using Bayesian estimates, may be implemented. An analysis model may also be incorporated which oversees the learning to accept or reject learning. Adjustments are achieved utilizing heuristics, rules, formulae, minimization of cost function(s) or tables (such as, for example, gain scheduling).

Model-based methods, such as a Kalman filter, can be programmed into the processor(s) of the system using appropriate embedded or inputted software to predict the outcome of adding a controlled amount of insulin or other drug to a user in terms of the expected glucose value. The structures and parameters of the models define the anticipated behavior.

Any of a variety of conventional controller design methodologies, such as PID (Proportional-Integral-Derivative) systems, full state feedback systems with state estimators, output feedback systems, LQG (Linear-Quadratic-Guassian) controllers, LQR (Linear-Quadratic-Regulator) controllers, eigenvalue/eigenstructure controller systems, and the like, could be used to design algorithms to perform physiological control. They typically function by using information derived from physiological measurements and/or user inputs to determine the appropriate control action to use. While the simpler forms of fixed controllers use fixed parameters (and therefore rules) for computing the magnitude of control action, the parameters in more sophisticated forms of such controllers may use one of more dynamic parameters. The one or more dynamic parameters could, for example, take the form of one or more continuously or discretely adjustable gain values. Specific rules for adjusting such gains could, for example, be defined either on an individual basis or on the basis of a user population, and in either case will typically be derived according to one or more mathematical models. Such gains are typically scheduled according to one or more rule sets designed to cover the expected operating ranges in which operation is typically nonlinear and variable, thereby reducing sources of error.

Model based control systems, such as those utilizing model predictive control algorithms, can be constructed as a black box wherein equations and parameters have no strict analogs in physiology. Rather, such models may instead be representations that are adequate for the purpose of physiological control. The parameters are typically determined from measurements of physiological parameters such as glucose level, insulin concentration, and the like, and from physiological inputs such as food intake, alcohol intake, insulin dose, and the like, and also from physiological states such as stress level, exercise intensity and duration, menstrual cycle phase, and the like. These models are used to estimate current glucose level or to predict future glucose levels. Such models may also take into account unused insulin remaining in the user after a bolus of insulin is given, for example, in anticipation of a meal. Such unused insulin will be variously described as unused, remaining, or "insulin on board."

A model based control system can perform a prediction of a user's blood glucose concentration in terms of a "best-estimate" as well as upper and/or lower bounds of the estimate for the present time and up to a finite time in the future. A Kalman filter can be implemented by the model based control system to estimate, predict, and model the best-estimate and the variance (i.e., upper and/or lower bounds) of a user's blood analyte concentration. A Kalman filter produces estimates of the true values of measurements of the user's blood glucose concentration by predicting a value, estimating the uncertainty of the predicted value, and computing a weighted average of the predicted value and the measured value. The most weight is given to the value with the least uncertainty. The estimates produced by the Kalman filter tend to be closer to the true values than the original measurements because the weighted average has a better estimated uncertainty than either of the values that went into the weighted average. The Kalman filter model assumes the true state at time k is evolved from the state at (k−1) according to $x_k = F_k x_{k-1} + B_k u_k + w_k$, where:

- $F_k$ is the state transition model which is applied to the previous state $x_{k-1}$;
- $B_k$ is the control-input model which is applied to the control vector $u_k$;
- $w_k$ is the process which is assumed to be drawn from a zero mean multivariate normal distribution with covariance $Q_k$.

The Kalman filter is a recursive estimator, which means that only the estimated state from the previous time step and the current measurement are needed to compute the estimate for the current state. In contrast to batch estimation techniques, no history of observations and/or estimates is required. In what follows, the notation $\hat{x}_{n|m}$ represents the estimate of x at time n given observations up to, and including time m. The state of the filter is represented by two variables:

1. $\hat{x}_{k|k}$, the a posteriori state estimate at time k given observations up to and including time k; and
2. $P_{k|k}$, the a posteriori error covariance matrix (e.g., a measure of the estimated accuracy of the state estimate.

The Kalman filter can be written as a single equation; however it is most often conceptualized as two distinct phases: "predict" and "update." The predict phase uses the state estimate from the previous timestep to produce an estimate of the state at the current timestep. The predicted state estimate is also known as the a priori state estimate because, although it is an estimate of the state at the current timestep, it does not include observation information from the current timestep. In the update phase, the current a priori prediction is combined with current observation information to refine the state estimate. The improved estimate is termed the a posteriori state estimate. Typically, the two phases alternate, with the prediction advancing the state until the next scheduled observation, and the update incorporating the observation. However, this is not necessary. If an observation is unavailable for some reason, the update may be skipped and multiple prediction steps performed. Likewise, if multiple independent observations are available at the same time, multiple update steps may be performed. The formula for the updated estimate and covariance of the Kalman filter can be seen below.

Predicted (i.e., a priori) state estimate: $\hat{x}_{k|k-1}=F_k\hat{x}_{k-1|k-1}+B_k u_k$ Predicted (i.e., a priori) estimate covariance:

$$P_{k|k-1} = F_k P_{k=-1|k-1} F_k^T + Q_k$$

Measurement residual: $\hat{y}=z_k-H_k\hat{x}_{k|k-1}$

Residual covariance:

$$S_k = H_k P_{k|k-1} H_k^T + R_k$$

Optimal Kalman Gain:

$$K_k = P_{k|k-1} H_k^T S_k^{-1}$$

Updated (i.e., a posteriori) state estimate: $\hat{x}_{k|k}=\hat{x}_{k|k-1}+K_k\hat{y}_k$; and Updated (i.e., a posteriori) estimate covariance: $P_{k|k}=(I-K_k H_k)P_{k|k-1}$.

More specifically, the Kalman filter of the model based control system can use the known user inputs described above and the user's blood analyte readings taken from the on-body sensor to determine a best-estimate of the user's actual blood analyte readings.

Insulin therapy is derived by the system based on the model's ability to predict glucose levels for various inputs. Other conventional modeling techniques may be additionally or alternatively used to predict glucose levels, including for example, but not limited to, building models from first principles.

In a system as described above, the controller is typically programmed to provide a "basal rate" of insulin deliver or administration. Such a basal rate is the rate of continuous supply of insulin by an insulin delivery device such as a pump that is used to maintain a desired glucose level in the user. Periodically, due to various events that affect the metabolism of a user, such as eating a meal or engaging in exercise, a "bolus" delivery of insulin is required. A "bolus" is defined as a specific amount of insulin that is required to raise the blood concentration of insulin to an effective level to counteract the effects of the ingestion of carbohydrates during a meal and also takes into account the effects of exercise on the glucose level of the user.

As described above, an analyte monitor may be used to continuously monitor the glucose level of a user. The controller is programmed with appropriate software and uses models as described above to predict the effect of carbohydrate ingestion and exercise, among other factors, on the predicted level of glucose of the user at a selected time. Such a model must also take into account the amount of insulin remaining in the blood stream from a previous bolus or basal rate infusion of insulin when determining whether or not to provide a bolus of insulin to the user.

Continuous glucose monitoring (CGM) systems occasionally exhibit non-zero-mean signal artifacts commonly called "dropout," where the sensor signal output is momentarily lower than it should be given an interstitial glucose value. From a closed-loop control perspective, this measurement error poses an annoyance in that the falsely lower signal could trigger a momentary reduction or cessation of insulin delivery commands due to the perceived hypoglycemic event. This can result in a false alarm based either on a perceived current glucose level or a computed future glucose level.

In certain embodiments of the present disclosure, techniques including computer implemented algorithms for reducing false hypoglycemic alarms due to a combination of a user's glucose range being mostly euglycemic (normal) and CGM system signal artifacts such as dropouts which tend to negatively bias the glucose display is provided. In such embodiments, the threshold for detecting a hypoglycemic threshold is modified by introducing a conditional time delay such that most dropouts are shorter in duration than the time delay so that the dropouts do not trigger an alarm. Additionally, the threshold is modified appropriately so that detection of true hypoglycemic events is not delayed beyond what has been determined to be clinically safe.

It is possible, using clinical data and insulin delivery information, to trust a CGM system to provide a balance between hypoglycemic detection sensitivity and reasonable specificity that minimizes false alarms under a wide range of glucose profiles. With good glycemic control, the proportion of true-hypoglycemia may be reduced significantly enough that signal artifacts of the CGM system become an important factor in causing false alarm rates.

In one embodiment of the present system, a combination of glucose level measurements, known as CGM signal artifact characteristics, and the best-estimate of relevant physiological states, such as, for example, plasma glucose, interstitial glucose, insulin on board, and effective insulin, are used to delay the enunciation of a CGM based hypoglycemic alarm and determine whether or not the alarm should persist. In this embodiment, instead of using an artifact detector which relies on a mechanism that is sensitive to the artifacts in the signal, the alarm instead is tuned to be insensitive to the artifacts, yet at the same time maintain a safe level of sensitivity to hypoglycemic events.

The CGM based hypoglycemic alarm of the one embodiment of the disclosure comprises several hypoglycemic thresholds. For each threshold, there exists a timer that may potentially annunciate a hypoglycemic alarm. The lower the threshold, the shorter the amount of delay between the time the CGM measurement value is obtained and when the alarm is sounded. The amount of delay depends primarily on the level of risk associated with the delayed response to a true hypoglycemic event at a given glucose level as well as the probability of the duration of false alarms due to the presence of CGM signal artifacts at a given glucose level.

The CGM based hypoglycemic alarm may result in the system recommending that a finger stick glucose level measurement request. If the glucose level measurement resulting from the finger stick indicates that the CGM measure hypoglycemia does not exist, the system can turn off the alarm. Alternatively, if the finger stick glucose level measurement confirms the presence of hypoglycemia, then the controller may indicate to the user that certain actions, such as taking rescue carbohydrates and/or checking glucose level frequently thereafter until the condition has been resolved, may be required.

A user with a well-controlled glucose level, using either a fully automatic closed loop system, a partial closed loop system or intensive open loop treatment, may have a glucose profile and distribution that is altered enough that the amount of false hypoglycemic alarms from the system is significantly larger than found in the general population of clinical data used to tune and confirm the hypoglycemic alarm response. The primary reason for this is that in the lower glucose range, the effect of signal artifacts from the CGM device become more dominant.

The CGM signal artifacts that reduce the effectiveness of the CGM based hypoglycemic alarm have been found to have an a priori distribution of severity, duration, and trajectory profile. Given a user's history of glucose levels, insulin delivery, and other relevant physiological information, a particular level of hypoglycemia carries a particular level of risk in terms of the maximum delay allowed before treatment should begin to avoid the effects of sever hypoglycemia. Delaying a hypoglycemic alarm to the extent that it is still clinically safe and yet as long as possible can reduce the false alarms due to the CGM signal artifacts.

Given a glucose level confirmation and possibly a corrective action such as administering rescue carbohydrates, glucose can be estimated with sufficient confidence such that for a finite horizon in the future, there is no need to activate the CGM based hypoglycemic alarm. This further decreases the likelihood of false alarms.

In one embodiment of the disclosure, the controller is programmed using appropriate software so as to set up two separate subsystems for decision making. While these subsystems will be described in terms of one or more state machines, those skilled in the art of control theory and engineering will understand that other embodiments may be contemplated. Thus, skilled artisans will understand how to program the processor to implement such a state machine.

Figure 3:
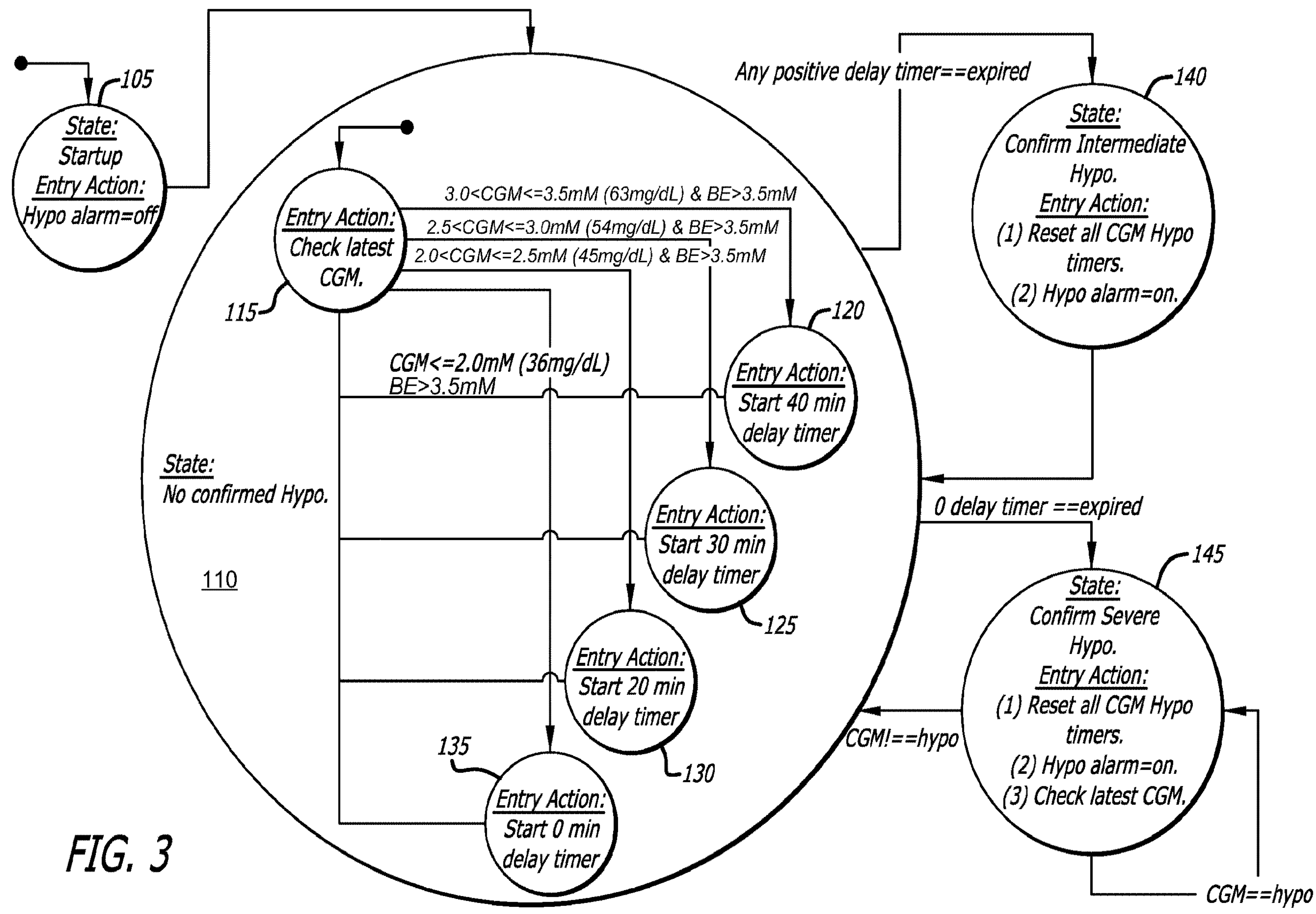
FIG. 3 is a schematic diagram of a continuous glucose monitor based subsystem, illustrated in terms of a state machine.

FIG. 3 illustrates a state machine which governs the behavior of the assertion of the CGM based hypoglycemic detector. FIG. 3 also depicts a state machine which governs how and when confirmatory glucose level measurements, such as by a finger stick, should be taken, how and when rescue carbohydrates should be administered, and when to de-assert the CGM based hypoglycemic detector.

Referring now to FIG. 3, in certain embodiments the CGM state machine is configured to determine when a hypoglycemic alarm should be asserted relative to a CGM threshold reading and a best-estimate of the user's BG concentration that is determined by the system. The CGM state machine begins at 105. When the CGM measurements become available, the state machine enters the "no hypoglycemia confirmed" state 110. Within this state, the controller obtains a current CGM value and also obtains a best-estimate of the user's blood glucose value, and dependent on the value of the measurements, controls the analysis along one of several paths. For example, if the latest CGM value (i.e., the CGM 115) is less than or equal to 3.5 mMol/L (63 mg/dL) but greater than 3.0 mMol/L (54 mg/dL), but the best-estimate determines that the BG concentration is above 3.5 mMol/L a delay timer of 40 minutes is implemented at state 120. If the detected CGM value is greater than 2.5 mMol/L (45 mg/dL) but less than or equal to 3.0 mMol/L (54 mg/dL), but the best-estimate determines that the BG concentration is above 3.5 mMol/L a delay of 30 minutes is implemented at state 125. Similarly, if the detected CGM value is greater than 2.0 mMol/L (36 mg/dL) but less than or equal to 2.5 mMol/L (45 mg/dL), but the best-estimate determines that the BG concentration is above 3.5 mMol/L a delay of 20 minutes is implemented at state 130.

When any of the timer set at states 120, 125, or 130 expire, and the latest CGM value is still no higher than the corresponding upper limits for the delayed timer module states 120, 125, or 130, the state changes to "confirm intermediate hypoglycemia" at state 140. In this state, the controller resets all the timers of states 120, 125, and 130, and sets the hypoglycemia alarm to on. This state prevents the alarm from sounding unnecessarily when a user's glucose level is still within a range where the annoyance of an alarm outweighs the risk that the user is actually in a hypoglycemic condition that requires immediate attention. Once the alarm is sounded, the CGM state machine returns to the "no confirmed hypoglycemia" state 110.

Where the detected CGM value is less than or equal to 2.0 mMol/L (36 mg/dL), which is indicative of severe hypoglycemia, no delay is implemented at state 135, and the machine exits from the "no confirmed hypoglycemia" state 110 to state 145. In this state, all of the timers of states 120, 125, and 130 are reset, the hypoglycemia alarm is set to on, thus sounding an alarm, and the controller continues to check the current CGM value and the best-estimate value. In this state the system cannot return to the "no confirmed hypoglycemia" state 110 until the latest CGM value rises above 3.5 mMol/L (63 mg/dL). The hypoglycemia alarm, which was already activated, is related to the glucose level subsystem. When the latest CGM value rises above 3.5 mMol/L, the CGM subsystem state machine returns to "no confirmed hypoglycemia" state 110, whether or not the latest alarm has been confirmed by a separate glucose level reading.

Figure 4:
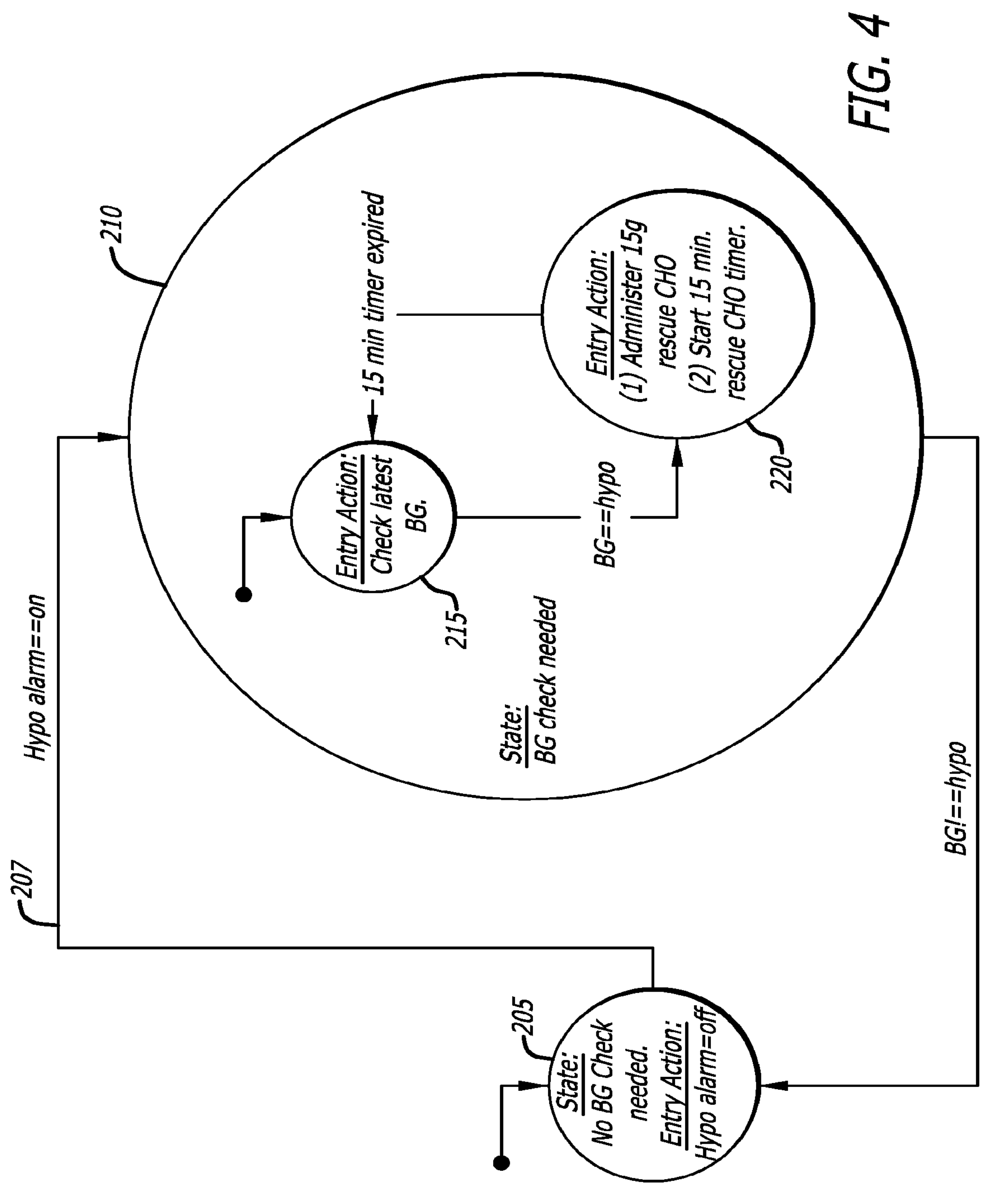
FIG. 4 is a schematic diagram of a glucose level based subsystem illustrated in terms of a state machine coupled to the continuous glucose monitor subsystem FIG. 3.

Referring now to FIG. 4, the controller is programmed to set up a separate blood glucose (BG) level subsystem, which will be described in terms of a state machine. This state machine de-asserts the hypoglycemic alarm upon non-hypoglycemic confirmation using a glucose level at a fixed threshold and/or a best-estimate of the glucose level, such as when the glucose level is equal and/or estimated to 3.5 mMol/L (63 mg/dL). When the system starts, the BG state machine initializes into state 205. In this state, no glucose level check is needed, and the hypoglycemia alarm is set to off.

When the CGM state machine asserts the hypoglycemic alarm at states 140 or 145, the BG state machine performs a transition 207, where the BG state machine enters a "BG check needed" state 210. In this state, the system requests and waits for a finger stick glucose level measurement at 215, and if a "BG equals hypoglycemia" confirmation results from the finger stick, the controller alerts the user at state 220. The hypoglycemia confirmation based on the BG finger stick may be set at the uppermost limit of the CGM state machine's limits, which may be equal to 3.5 mMol/L (63 mg/dL) as depicted in FIG. 2, or any other suitable value. The user may then address the low glucose level measurement by taking rescue carbohydrates at state 220. This action may be recommended by the controller. The controller also requests another glucose level be measured in 15 minutes. This process continues until the latest glucose level indicates that the user is no longer in a hypoglycemic state.

The previous embodiments illustrated in FIGS. 3 and 4 may be generalized further by removing the actions "confirm intermediate hypoglycemia" (FIG. 3, reference number

140) and "confirm severe hypoglycemia" (FIG. 3, reference number 145) from the CGM state machine. In this embodiment, no CGM hypoglycemia timers are reset until the timers expire and the hypoglycemia alarm is annunciated. This allows for several alarm mechanisms to occur simultaneously.

In certain embodiments, if the current CGM glucose value rises above 3.5 mMol/L at any time while the CGM state machine is in the "no confirmed hypoglycemia" state 110, the alarm may be reset and the controller returns to processing incoming CGM data as before. In this case, no alarm will be sounded.

Figure 5A:
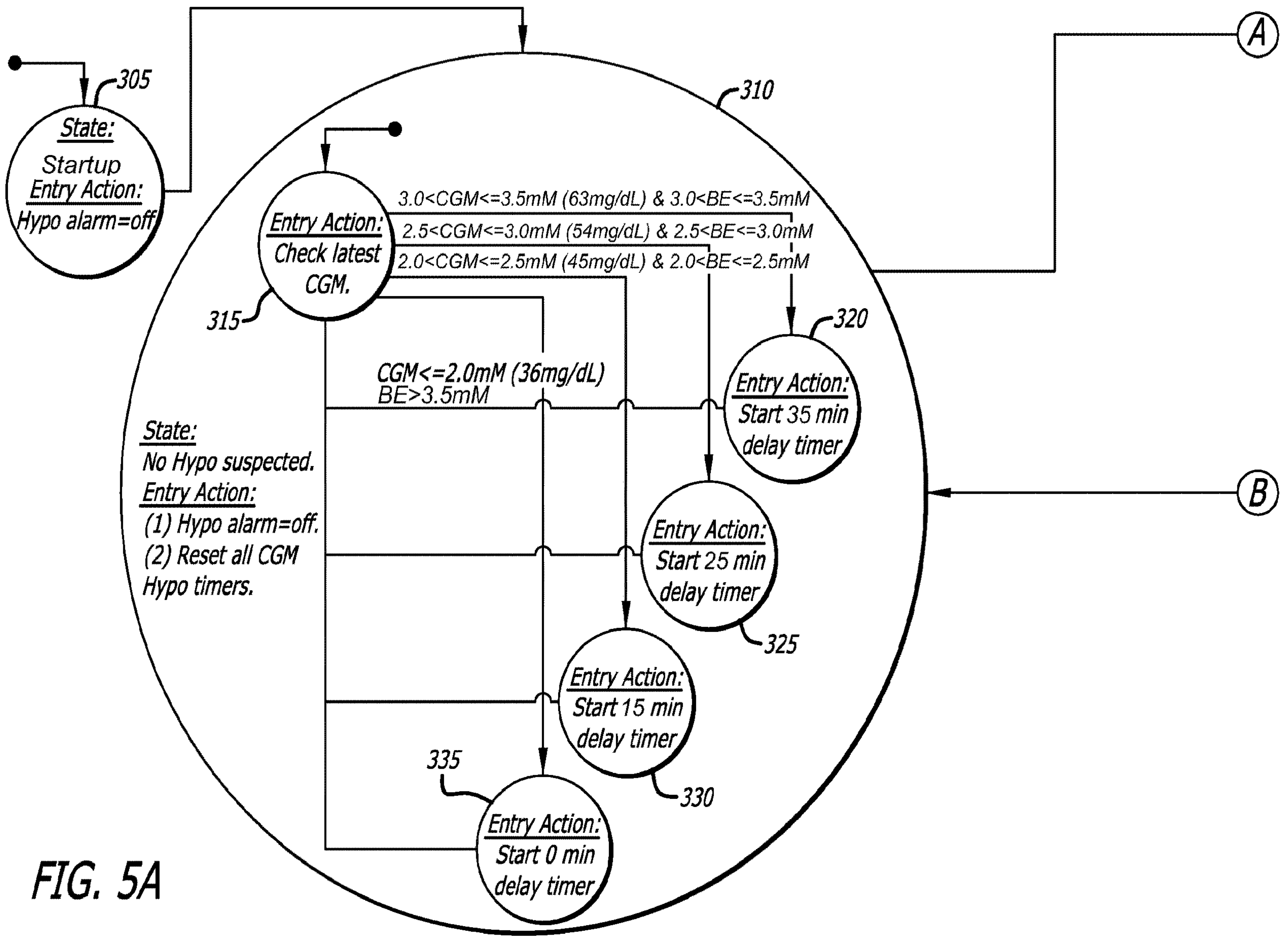
FIGS. 5A and 5B are schematic diagrams of an embodiment of the disclosure wherein the continuous glucose monitor and glucose level state machines are coupled to a stronger degree than the embodiments shown in FIGS. 3 and 4, and also showing an additional delay timer asserted after glucose level confirmation.
Figure 5B:
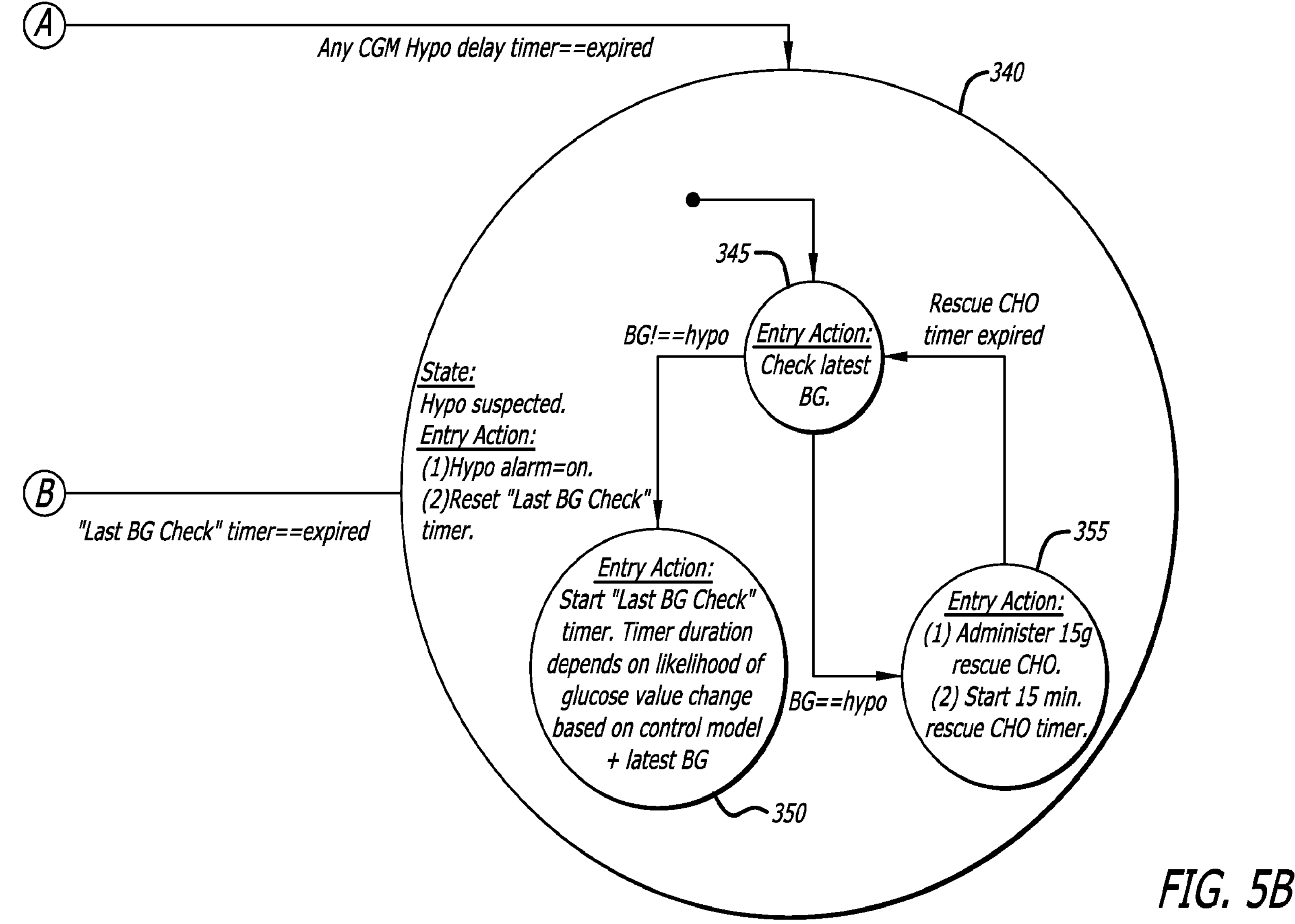

Referring now to FIG. 5A and FIG. 5B, another embodiment utilizes prior knowledge of various factors such as glucose level, CGM value, insulin on board, and the like, to further minimize false alarms by modifying the length of the delay timer if there is a convergence in the information gathered from the CGM sensor and the best-estimate of the user's BG level. As in the embodiment depicted in FIG. 3, the CGM state machine asserts the hypoglycemic alarm, and the BG state machine de-asserts the alarm. The CGM state machine begins at 305. However, the two state machines are coupled even further with the assumption that while the system is set at a "hypoglycemia suspected" state 340, no CGM based hypoglycemic threshold shall matter. In addition, depending on the control model and the value from the latest finger stick glucose level check, a variable time can be added to delay the return into the periodic CGM based hypoglycemic detection "no hypoglycemia suspected" state 310.

For example, if the latest finger stick BG value is 4.0 mMol/L (72 mg/dL), and the control model predicts a rapidly rising glucose level, then a relatively short delay timer might be activated before the system transitions from "hypoglycemia suspected" state 340 to the "no hypoglycemia suspected" state 310. On the other hand, if the latest finger stick BG check indicates a glucose level value of 4.0 mMol/L (72 mg/dL) and the control model programmed into the controller predicts a rapidly dropping glucose level profile, then the system immediately transitions from the "hypoglycemia suspected" state 340 to "no hypoglycemia suspected" state 310, but the CGM based hypoglycemia detector will be given the fastest opportunity to trigger. Using the control model and relative value of the latest finger stick BG check allows the system to apply a state transition rule that is decoupled from which CGM based hypoglycemic detector triggered the state transition, thus preventing false hypoglycemia alarms.

Referring to FIG. 5A, in state 310, if the latest CGM value (i.e., the CGM 315) is less than or equal to 3.5 mMol/L (63 mg/dL) but greater than 3.0 mMol/L (54 mg/dL), but the best-estimate determines that the BG concentration is less than or equal to 3.5 mMol/L but greater than 3.0 mMol/L a delay timer of 35 minutes is implemented at state 320. If the detected CGM value is greater than 2.5 mMol/L (45 mg/dL) but less than or equal to 3.0 mMol/L (54 mg/dL), but the best-estimate determines that the BG concentration is less than or equal to 3.0 mMol/L but greater than 2.5 mMol/L a delay of 25 minutes is implemented at state 325. Similarly, if the detected CGM value is greater than 2.0 mMol/L (36 mg/dL) but less than or equal to 2.5 mMol/L (45 mg/dL), but the best-estimate determines that the BG concentration is less than or equal to 2.5 mMol/L but greater than 2.0 mMol/L a delay of 15 minutes is implemented at state 330. Where the detected CGM value is less than or equal to 2.0 mMol/L (36 mg/dL), which is indicative of severe hypoglycemia, no delay is implemented at state 335.

Referring to FIG. 5B, when the "hypoglycemia suspected" state 340 is entered, a finger stick BG value is requested at state 345. Depending on the glucose level profile of the user, that is, the profile due to prior insulin deliveries, insulin sensitivity, exercise and the like, the controller may enter either state 355, where rescue carbohydrates are administered and the finger stick BG is again measured after fifteen minutes, or state 350, where a timer indicating when the next finger stick BG confirmation is to be performed is started. The duration of this timer is dependent upon a determination of the likelihood of glucose value changes based on the future glucose level profile determined by the control model being used by the controller and the latest finger stick glucose level value.

In this embodiment, the system checks the CGM value at every sample time, instead of using four or more distinct hypoglycemia thresholds with specific time delay amounts, and continues to count-down the timer until it is larger than a latest-glucose-dependent timer.

In certain embodiments, a table of delay values as a function of glucose level is used by the processor to modify the timer delay, where crossing a lower glucose value results in a shorter alarm delay. An alarm will be annunciated whenever any timer expires (e.g., the glucose value remains below that threshold value for the duration of the timer delay). Table 1 below depicts a table that can be used by the processor to modify the timer delay.

TABLE 1

Table implemented by the processor to determine the timer delay based upon a user's glucose concentration.

| Glucose Concentration (mg/dL) | Time (minutes) |
|---|---|
| 60 | 30 |
| 50 | 15 |
| 45 | 0 |

For example, if the CGM sensor detects a drop in the user's blood glucose concentration to a hypoglycemic level, but the best-estimate predicts that the user's blood glucose is at a euglycemic level, then the likelihood of an actual hypoglycemic event is low. Various reasons could cause such a divergence, such as a CGM calibration error or CGM signal distortion errors such as night-time drop outs. When the user's glucose level falls below 60 mg/dL, but is above 50 mg/dL, the alarm will be delayed for 30 minutes. When the CGM sensor detects a glucose level between 50 mg/dL and 45 mg/dL, the alarm is delayed 15 minutes prior to annunciating. If the user's glucose level falls below 45 mg/dL, then the alarm annunciates immediately.

However if there is agreement between the user's blood glucose concentration determined by the CGM sensor and the best-estimate prediction that a hypoglycemic event is likely, then the system can modify the alarm mechanism to thereby decrease the likelihood of imposing unnecessary risk to the user. As the likelihood of a hypoglycemic event increases to a higher risk, the mechanism described above with respect to Table 1 can be implemented with a 50% shortening of the alarm delay, as seen below in Table 2. In this embodiment, the alarm delay is shortened to 15 minutes when the detected CGM value crosses the 60 mg/dL threshold. The alarm delay is shortened to 7.5 minutes when the detected CGM value crosses the 50 mg/dL threshold. However, the alarm is still annunciated immediately when the detected CGM value crosses the 45 mg/dL threshold.

TABLE 2

| Table implemented by the processor with a shortened alarm delay based upon an increased risk of a hypoglycemic event. | |
|---|---|
| Glucose Concentration (mg/dL) | Time (minutes) |
| 60 | 15 |
| 50 | 7.5 |
| 45 | 0 |

In certain embodiments, as the likelihood of a hypoglycemic event increases, the same delay times as seen in Table 1 are retained, but the threshold values for blood analyte concentration are increased. For example, Table 3 illustrates that the alarm delay is set for 30 minutes when the detected CGM value crosses the 65 mg/dL threshold, that the alarm delay is set for 15 minutes when the detected CGM value crosses the 55 mg/dL threshold, and the alarm is annunciated immediately when the detected CGM value crosses the 50 mg/dL threshold.

TABLE 3

| Table implemented by the processor with an increased blood glucose concentration based upon an increased risk of a hypoglycemic event. | |
|---|---|
| Glucose Concentration (mg/dL) | Time (minutes) |
| 65 | 30 |
| 55 | 15 |
| 50 | 0 |

In certain embodiments, a hybrid between the two previously described embodiments is implemented, wherein both threshold values and time delays are adjusted if the best-estimate glucose range determined by the model determines a heightened risk of a hypoglycemic event. As seen in Table 4 below, both the glucose threshold and the time delay are modified to avoid imposing unnecessary risk to the user.

TABLE 4

| Table implemented by the processor with an increased blood glucose concentration and shortened alarm delay based upon an increased risk of a hypoglycemic event. | |
|---|---|
| Glucose Concentration (mg/dL) | Time (minutes) |
| 65 | 15 |
| 55 | 7.5 |
| 50 | 0 |

In further embodiments, the same principles of the previous three embodiments can be applied to hyperglycemia detection, such that the tiered thresholds increase in the order of the threshold values. For example, if the information received from the analyte sensor and the best-estimate of the user's analyte concentration are in divergence with one another the system waits 30 minutes when the detected CGM value reaches a 180 mg/dL threshold and remains at that threshold before triggering the alarm, the system waits 15 minutes when the detected CGM value crosses a 200 mg/dL threshold and remains at that threshold before triggering the alarm, and the system waits 7.5 minutes once the detected CGM value reaches a 220 mg/dL threshold and remains at that threshold before triggering the alarm. However, as illustrated below in Table 5, if there is convergence between the data received from the detected CGM value and the best-estimate of the user's blood glucose concentration, then the system can modify one or both of the glucose concentration threshold and the length of time the system waits before asserting the hyperglycemia alarm.

TABLE 5

| Table implanted by the processor with a decrease in the hyperglycemic alarm delay based upon an increased risk of a hyperglycemic event. | |
|---|---|
| Glucose Concentration (mg/dL) | Time (minutes) |
| 180 | 15 |
| 200 | 7.5 |
| 220 | 3.75 |

The embodiments described above are particularly useful in reducing or eliminating unnecessary risk to a user by implementing hypoglycemic/hyperglycemic alarms in a timely manner. While several specific embodiments have been illustrated and described, it will be apparent that various modifications can be made without departing from the spirit and scope of the disclosure. Accordingly, it is not intended that the disclosure be limited, except as by the appended claims.

In certain embodiments, a computer-implemented method for determining when to activate an alarm of a continuous analyte monitor may comprise receiving, at a data processing component, information from the continuous analyte monitor related to the user's analyte concentration, determining, at the data processing component, the user's analyte concentration using the information received from the continuous analyte monitor, receiving, at a data processing component, information from the user related to the user's analyte concentration, determining, at a data processing component, a best-estimate of the user's analyte concentration based upon the information from the continuous analyte monitor and information from the user, determining, at a data processing component, at least one condition for activating the alarm, and modifying, at a data processing component, the at least one condition for activating the alarm based on a comparison between the determination of the user's analyte concentration and the best-estimate of the user's analyte concentration.

Certain aspects may include that a best-estimate of the user's analyte concentration includes a range of variance.

Certain aspects may include activating, at the processor, the analyte alarm if at least one of the data signal related to the user's analyte concentration satisfies the at least one determined condition.

Certain aspects may include that the best-estimate of the user's analyte concentration is at least partially determined using at least one of a Kalman filter and other state observers.

Certain aspects may include that the at least one condition for activating the analyte alarm includes receiving a data signal that indicates that the user's analyte concentration has reached a threshold value.

Certain aspects may include that the at least one condition includes that the user's analyte concentration crosses a threshold value for a predetermined length of time.

Certain aspects may include that when the comparison between the determination of the user's analyte concentration and the best-estimate of the user's analyte concentration are in high agreement with each other, this suggests an increased likelihood of true physiological events such as a hypoglycemic event.

Certain aspects may include that when the comparison between the determination of the user's analyte concentration and the best-estimate of the user's analyte concentration are in high agreement with each other, this suggests an increased likelihood of a true physiological events such as a hyperglycemic event.

Certain aspects may include that the modification includes increasing or decreasing the threshold value of the user's analyte concentration.

Certain aspects may include that when the comparison between the determination of the user's analyte concentration and the best-estimate of the user's analyte concentration suggests an increased likelihood of a hypoglycemic event, the threshold value is increased, and wherein when the comparison between the determination of the user's analyte concentration and the best-estimate of the user's analyte concentration suggests a low likelihood of a hypoglycemic event, the threshold value is decreased.

Certain aspects may include that the modification includes increasing or decreasing the predetermined duration that the user's analyte concentration may cross the threshold value.

Certain aspects may include that the modification includes increasing or decreasing the threshold value for the user's analyte concentration, and includes increasing or decreasing the predetermined duration that the user's analyte concentration may cross the threshold value.

Certain aspects may include that the information from the continuous analyte monitor includes at least one data signal.

In certain embodiments, an integrated analyte monitoring device assembly may comprise an analyte sensor for transcutaneous positioning through a skin layer and maintained in fluid contact with an interstitial fluid under the skin layer during a predetermined time period, the analyte sensor having a proximal portion and a distal portion, and sensor electronics coupled to the analyte sensor that may comprise a circuit board having a conductive layer and a sensor antenna disposed on the conductive layer, one or more electrical contacts provided on the circuit board and coupled with the proximal portion of the analyte sensor to maintain continuous electrical communication, and a data processing component provided on the circuit board and in signal communication with the analyte sensor, the data processing component configured to execute one or more routines for processing signals received from the analyte sensor, the data processing component configured to control the transmission of data associated with the processed signals received from the analyte sensor to a remote location using the sensor antenna in response to a request signal received from the remote location, the data processing component configured to receive information from the continuous analyte monitor related to the user's analyte concentration, the data processing unit configured to determine the user's analyte concentration using the information received from the continuous analyte monitor, the data processing component configured to receive data from the user related to the user's analyte concentration, the data processing component configured to determine a best-estimate of the user's analyte concentration based upon the information received from the continuous analyte monitor and the data received from the user at the processor, the data processing component configured to determine at least one condition for activating an alarm, the data processing component configured to modify the at least one condition for activating the alarm based on a comparison between the determination of the user's analyte concentration and the best-estimate of the user's analyte concentration.

Certain aspects may include that the best-estimate of the user's analyte concentration includes a range of variance.

Certain aspects may include that the data processing component is further configured to activate the alarm if at least one of the data signals related to the user's analyte concentration and the best-estimate of the user's analyte concentration satisfies the at least one determined condition.

Certain aspects may include that the best-estimate of the user's analyte concentration is at least partially determined using at least one of a Kalman filter and other state observers.

Certain aspects may include that the at least one condition for activating the alarm includes receiving a data signal that indicates that the user's glucose concentration has reached a threshold value.

Certain aspects may include that the at least one condition includes that the user's analyte concentration crosses a threshold value for a predetermined length of time.

Certain aspects may include that when the comparison between the determination of the user's analyte concentration and the best-estimate of the user's analyte concentration are in high agreement with each other, this suggests an increased likelihood of a hypoglycemic event.

Certain aspects may include that when the comparison between the determination of the user's analyte concentration and the best-estimate of the user's analyte concentration are in high agreement with each other, this suggests an increased likelihood of true physiological events such as a hyperglycemic event.

Certain aspects may include that the modification includes increasing or decreasing the threshold value of the user's glucose concentration.

Certain aspects may include that when the comparison between the determination of the user's analyte concentration and the best-estimate of the user's analyte concentration suggests an increased likelihood of a hypoglycemic event, the threshold value is increased, and wherein when the comparison between the determination of the user's analyte concentration and the best-estimate of the user's analyte concentration suggests a low likelihood of a hypoglycemic event, the threshold value is decreased.

Certain aspects may include that the modification includes increasing or decreasing the predetermined duration that the user's analyte concentration may cross the threshold value.

Certain aspects may include that the modification includes increasing or decreasing the threshold value for the user's analyte concentration, and includes increasing or decreasing the predetermined length of time that the user's analyte concentration may cross the threshold value.

Certain aspects may include that the information from the continuous analyte monitor includes at least one data signal.

In some embodiments, an integrated analyte monitoring device may comprise a data processing component provided on a circuit board and in signal communication with a continuous analyte monitor that may be configured to execute one or more routines for processing signals received from the continuous analyte monitor, control the transmission of data associated with the processed signals received from the continuous analyte monitor to a remote location using an antenna in response to a request signal received from the remote location, receive information from the continuous analyte monitor related to the user's analyte concentration, determine the user's analyte concentration using the information received from the continuous analyte monitor, receive data from the user related to the user's analyte concentration, determine a best-estimate of the user's analyte concentration based upon the information received from the continuous analyte monitor and the data received from the user at the processor, determine at least one condition for activating an alarm, and modify the at least one condition for activating the alarm based on the comparison between the determination of the user's analyte concentration and the best-estimate of the user's analyte concentration.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. A method for monitoring a glucose concentration of a user, said method comprising:

receiving, from a glucose sensor, first measurement data related to the glucose concentration of the user, wherein at least a portion of the glucose sensor is transcutaneously positioned in contact with a bodily fluid of the user;

determining a value of the glucose concentration of the user based on the first measurement data received from the glucose sensor;

determining a best-estimate of the glucose concentration of the user based on the first measurement data received from the glucose sensor;

gathering additional glucose measurement data from the glucose sensor, resulting in a set of measurement data being obtained from the glucose sensor over time, the set of measurement data including the first measurement data;

determining that there is a convergence between the set of measurement data, which is gathered over time, and the best-estimate; and modifying at least one condition for activating an alarm based on the convergence between the best-estimate and the set of measurement data.

2. The method of claim 1, wherein determining the best-estimate of the glucose concentration of the user uses insulin administration information of the user, and wherein the insulin administration information includes an insulin administration history of the user.

3. The method of claim 1, wherein determining the best-estimate of the glucose concentration of the user uses insulin administration information of the user, and wherein the insulin administration information includes an insulin sensitivity profile of the user.

4. The method of claim 1, wherein the at least one condition for activating the alarm includes an alarm delay timer.

5. The method of claim 4, wherein a modified value of the alarm delay timer is based on the set of measurement data received from the glucose sensor.

6. The method of claim 1, wherein the at least one condition for activating the alarm includes a threshold value associated with activating the alarm.

7. The method of claim 1, further comprising determining whether the best-estimate and the set of measurement data both exceed a threshold value.

8. The method of claim 1, further comprising determining whether the best-estimate exceeds a first threshold value and the set of measurement data exceeds a second threshold value.

9. The method of claim 1, further comprising determining a best-estimate of the glucose concentration of the user by:

predicting an estimate of a true value of a blood glucose concentration of the user;

estimating an uncertainty of the predicted true value; and computing a weighted average of the predicted true value and the value of the glucose concentration of the user based on the set of measurement data received from the glucose sensor, wherein weights of the weighted average are based on the estimated uncertainty.

10. The method of claim 9, wherein the weighted average is based on an estimate of the true value of the blood glucose concentration of the user at a previous time.

11. The method of claim 1, wherein the bodily fluid is interstitial fluid.

12. The method of claim 1, wherein the at least one condition for activating the alarm is associated with a hyperglycemic state.

13. The method of claim 1, wherein the at least one condition for activating the alarm is associated with a hypoglycemic state.

14. The method of claim 1, wherein the best-estimate includes a range of values, including an upper bound and a lower bound, and wherein determining that there is a convergence between the best-estimate and the set of measurement data comprises determining that the upper bound of the best-estimate equals an upper bound of the set of measurement data, and that the lower bound of the best-estimate equals a lower bound of the set of measurement data.

15. A glucose monitoring system comprising:

a glucose sensor configured to be transcutaneously positioned in contact with a bodily fluid of a user to monitor a glucose concentration;

on-body electronics electrically and communicatively coupled with the glucose sensor; and a display device comprising one or more processors and a memory communicatively coupled with the one or more processors and in wireless communication with the on-body electronics, wherein the memory comprises instructions which, when executed by the one or more processors, cause the display device to:

receive, from the on-body electronics, first measurement data related to the glucose concentration of the user;

determine a value of the glucose concentration of the user based on the first measurement data;

determine a best-estimate of the glucose concentration of the user based on the first measurement data received from the glucose sensor;

gather additional glucose measurement data from the glucose sensor, resulting in a set of measurement data being obtained from the glucose sensor over time, the set of measurement data including the first measurement data;

modify at least one condition for activating an alarm when the set of measurement data converges with the best-estimate; and activate the alarm based on determining that the at least one condition is satisfied.

16. The glucose monitoring system of claim 15, wherein determining the best-estimate of the glucose concentration of the user uses insulin administration information of the user, and wherein the insulin administration information includes an insulin administration history of the user.

17. The glucose monitoring system of claim 15, wherein determining the best-estimate of the glucose concentration of the user uses insulin administration information of the user, and wherein the insulin administration information includes an insulin sensitivity profile of the user.

18. The glucose monitoring system of claim 15, wherein the at least one condition for activating the alarm includes an alarm delay timer.

19. The glucose monitoring system of claim 18, wherein a modified value of the alarm delay timer is based on the set of measurement data received from the glucose sensor.

20. The glucose monitoring system of claim 15, wherein the best-estimate includes a range of values, including an upper bound and a lower bound, and wherein determining that there is a convergence between the best-estimate and the set of measurement data comprises determining that the upper bound of the best-estimate equals an upper bound of the set of measurement data, and that the lower bound of the best-estimate equals a lower bound of the set of measurement data.

* * * * *